(12) United States Patent
Srivastava et al.

(10) Patent No.: US 11,340,219 B2
(45) Date of Patent: May 24, 2022

(54) ANTI-PY1235-MET IMMUNOLOGICAL BINDING REAGENT

(71) Applicant: THE UNITED STATES OF AMERICA AS REPRESENTED BY THE SECRETARY OF THE DEPARTMENT OF HEALTH AND HUMAN SERVICES, Rockville, MD (US)

(72) Inventors: Apurva K. Srivastava, Rockville, MD (US); Thomas D. Pfister, Rockville, MD (US); Tony Navas, Rockville, MD (US); Ralph E. Parchment, Rockville, MD (US); James E. Doroshow, Rockville, MD (US)

(73) Assignee: The United States Of America, As Represented by the Secretary, Department Of Health And Human Services, Bethesda, MD (US)

( * ) Notice: Subject to any disclaimer, the term of this patent is extended or adjusted under 35 U.S.C. 154(b) by 627 days.

(21) Appl. No.: 16/085,999

(22) PCT Filed: Mar. 16, 2017

(86) PCT No.: PCT/US2017/022783
§ 371 (c)(1),
(2) Date: Sep. 17, 2018

(87) PCT Pub. No.: WO2017/161169
PCT Pub. Date: Sep. 21, 2017

(65) Prior Publication Data
US 2020/0292537 A1 Sep. 17, 2020

Related U.S. Application Data

(60) Provisional application No. 62/309,920, filed on Mar. 17, 2016.

(51) Int. Cl.
*G01N 33/543* (2006.01)
*C07K 16/44* (2006.01)
*C12N 15/63* (2006.01)

(52) U.S. Cl.
CPC ....... *G01N 33/54306* (2013.01); *C07K 16/44* (2013.01); *C12N 15/63* (2013.01); *C07K 2317/565* (2013.01); *G01N 2333/705* (2013.01); *G01N 2800/52* (2013.01)

(58) Field of Classification Search
CPC ....... G01N 33/54306; G01N 2333/705; G01N 2800/52; C12N 15/63; C07K 2317/565
See application file for complete search history.

(56) References Cited

U.S. PATENT DOCUMENTS

| | | | |
|---|---|---|---|
| 5,747,654 | A | 5/1998 | Pastan et al. |
| 5,770,380 | A | 6/1998 | Hamilton et al. |
| 5,888,773 | A | 3/1999 | Jost et al. |
| 6,558,672 | B1 | 5/2003 | Pastan et al. |
| 6,818,418 | B1 | 11/2004 | Lipovsek et al. |
| 7,115,396 | B2 | 10/2006 | Lipovsek et al. |
| 2009/0047211 | A1 | 2/2009 | Pastan et al. |

FOREIGN PATENT DOCUMENTS

| | | |
|---|---|---|
| EP | 0404097 | 12/1990 |
| WO | 9311161 | 6/1993 |
| WO | 2017161169 | 9/2017 |

OTHER PUBLICATIONS

Nava et al. 2014 AACR Meeting, Abstract and Poster #1049, Meeting Date: Apr. 5-9, 2014 (Year: 2014).*
Chiara Federica, et al., "Mutations in the Met Oncogene Unveil a "Dual Switch" Mechanism Controlling Tyrosine Kinase Activity", Journal of Biological Chemistry, vol. 278, No. 31, May 12, 2003, 7 pages.
Navas, Tony, et al., Vimentin: E-Cadherin (Log) "Quantitative Immunofluorencence Assessment of MET and Epithelial-To-Mesenchymal Transition (EMT) Biomarker Modulation by Antiagiogenic Inhibitors in Xengraft Tumor Tissues", retrieved from URL:https://dctd.cancer.gov/researchResources/posters/2014_AACR_MET_EMT, May 29, 2017, 1 page.
International Search Report and Written Opinion from related PCT Application PCT/US2017/022783 dated Jun. 12, 2017, 14 pages.
Baker, Stability of Phosphoprotein Stability of Phosphoprotein as a Biological Marker of Tumor Signaling, Clinical Cancer Research, vol. 11, No. 12, Jun. 15, 2005, pp. 4338-4340.
Basilico et al., Tivantinib (ARQ197) Displays Cytotoxic Activity That is Independent of Its Ability to Bind MET, Clinical Cancer Research, vol. 19, No. 9, 2013, pp. 2381-2392.
Blumenschein Jr. et al., Targeting the Hepatocyte Growth Factor-cMET Axis in Cancer Therapy, Journal of Clinical Oncology, vol. 30, No. 26, Sep. 10, 2012, pp. 3287-3296.
Cepero et al., MET and KRAS Gene Amplification Mediates Acquired Resistance to MET Tyrosine Kinase Inhibitors, Cancer Research, vol. 70, No. 19, Oct. 1, 2010, pp. 7580-7590.

(Continued)

*Primary Examiner* — Peter J Reddig
*Assistant Examiner* — Cheng Lu
(74) *Attorney, Agent, or Firm* — Polsinelli PC; Ron Galant

(57) ABSTRACT

Methods and compositions are described herein for assaying the presence or absence of pY1235-MET or a fragment thereof.

12 Claims, 26 Drawing Sheets

Specification includes a Sequence Listing.

(56) References Cited

OTHER PUBLICATIONS

Christensen et al., A Selective Small Molecule Inhibitor of c-MET Kinase Inhibits c-MET-dependent Phenotypes in Vitro and Exhibits Cytoreductive Antitumor Activity in Vivo, Cancer Research, vol. 63, No. 21, Nov. 1, 2003, pp. 7345-7355.
Christensen et al., c-MET as a Target for Human Cancer and Characterization of Inhibitors for Therapeutic Intervention, Cancer Letters, vol. 225, Issue 1, Jul. 8, 2005, 26 pages.
Cristiani et al., Regulation of the Wild-type and Y1235d Mutant Met Kinase Activation, Biochemistry, vol. 44, No. 43, 2005, 10 pages.
Eathiraj et al., Discovery of a Novel Mode of Protein Kinase Inhibition Characterized by the Mechanism of Inhibition of Human Mesenchymal-epithelial Transition Factor (c-MET) Protein Autophosphorylation by Arq 197, Journal of Biological Chemistry, vol. 286, No. 23, Jun. 10, 2011, pp. 20666-20676.
Eder, Novel Therapeutic Inhibitors of the c-MET Signaling Pathway in Cancer, Clinical Cancer Research, vol. 15, No. 7, Apr. 1, 2009, pp. 2207-2214.
Engelman et al., MET Amplification Leads to Gefitinib Resistance in Lung Cancer by Activating ERBB3 Signaling, Science, vol. 316, Issue No. 5827, May 18, 2007, pp. 1039-1043.
European Application No. 17714118.1, Office Action dated Oct. 25, 2019, 3 pages.
Furlan et al., Thirty Years of Research on Met Receptor to Move a Biomarker from Bench to Bedside, Cancer Research, vol. 74, No. 23, Nov. 19, 2014, pp. 6737-6744.
Guo et al., Signaling Networks Assembled by Oncogenic EGFR and c-MET, Proceedings of the National Academy of Sciences, vol. 105, No. 2, Jan. 15, 2008, pp. 692-697.
Lefebvre et al., MeET Degradation: More Than One Stone to Shoot a Receptor Down, The FASEB Journal, vol. 26, No. 4, Apr. 2012, pp. 1387-1399.
Longati et al., Tyrosines1234-1235 Are Critical for Activation of the Tyrosine Kinase Encoded by the MET Proto-oncogene (HGF Receptor), Oncogene, vol. 9, No. 1, Jan. 1994, 10 pages.
International Application No. PCT/US2017/022783, International Preliminary Report on Patentability dated Sep. 27, 2018, 7 pages.
Rege-Cambrin, Karyotypic Analysis of Gastric Carcinoma Cell Lines Carrying an Amplified c-MET Oncogene, Cancer Genetics and Cytogenetics, vol. 64, No. 2, Dec. 1992, 4 pages.
Tsuta et al., c-MET/phospho-met Protein Expression and Met Gene Copy Number in Non-small Cell Lung Carcinomas, Journal of Thoracic Oncology, vol. 7, No. 2, Feb. 2012, pp. 331-339.
International Application No. PCT/US2017/022783, International Search Report dated Jun. 12, 2017, 9 pages.
Navas et al., Vimentin: E-cadherin (Log) Quantitative immunofluorescence assessment of MET and epithelial-to-mesenchymal transition (EMT) biomarker modulation by antiangiogenic inhibitors in xenograft tumor tissues, https://dctd.cancer.gov/ResearchResources/posters/2014 AACR_MET_EMT.pdf, XPO55376433, Jun. 13, 2014, 1 page.

\* cited by examiner

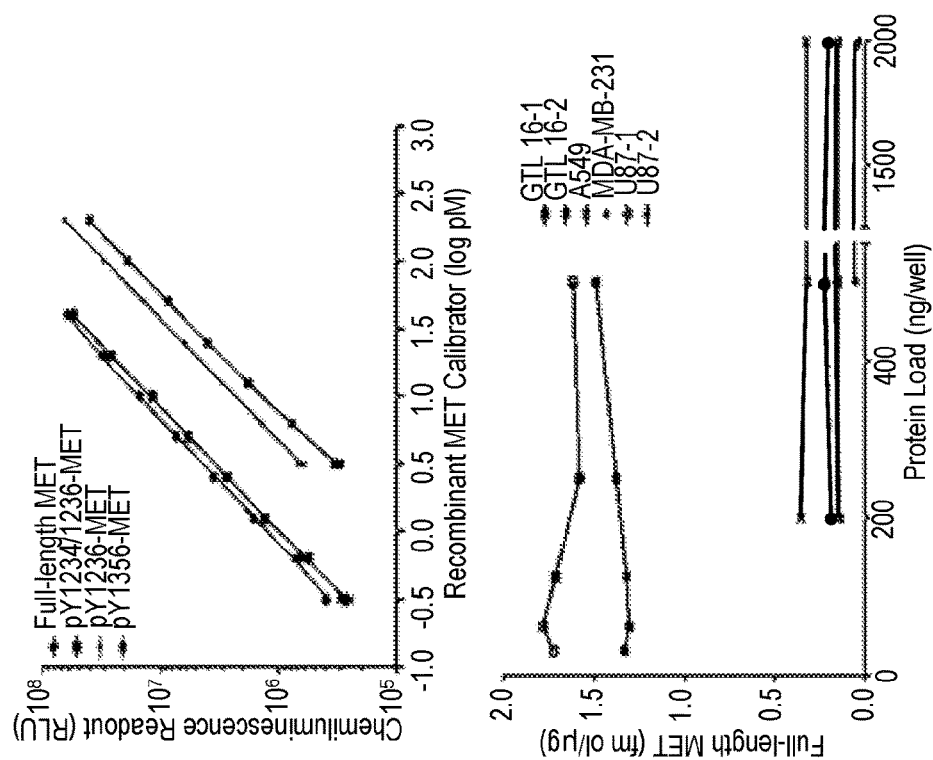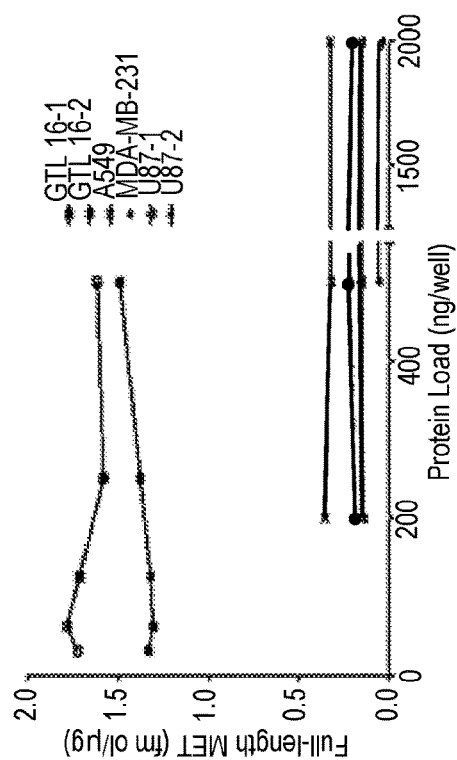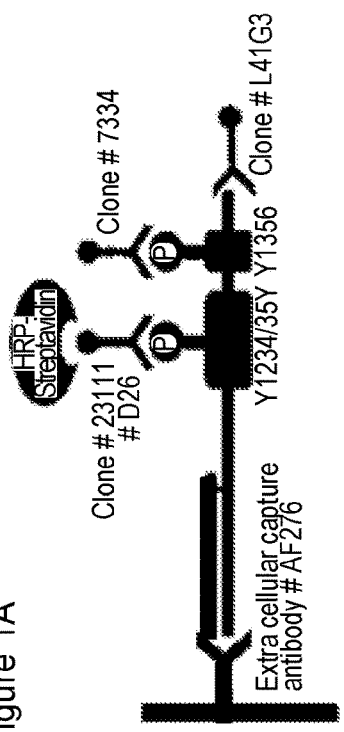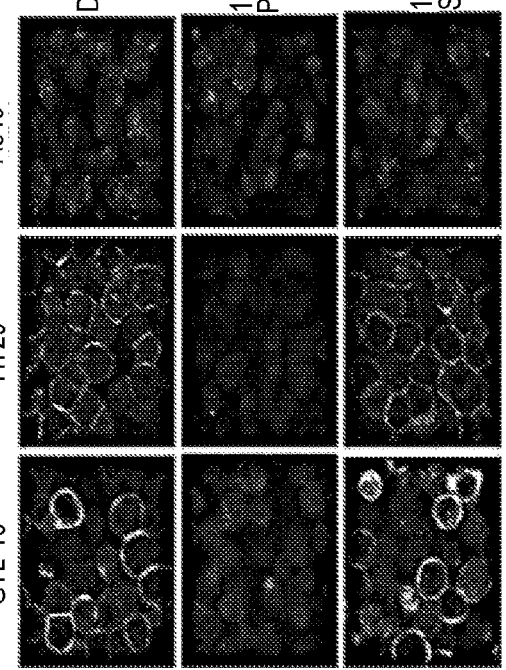
Figure 1A
Figure 1B
Figure 1C
Figure 1D

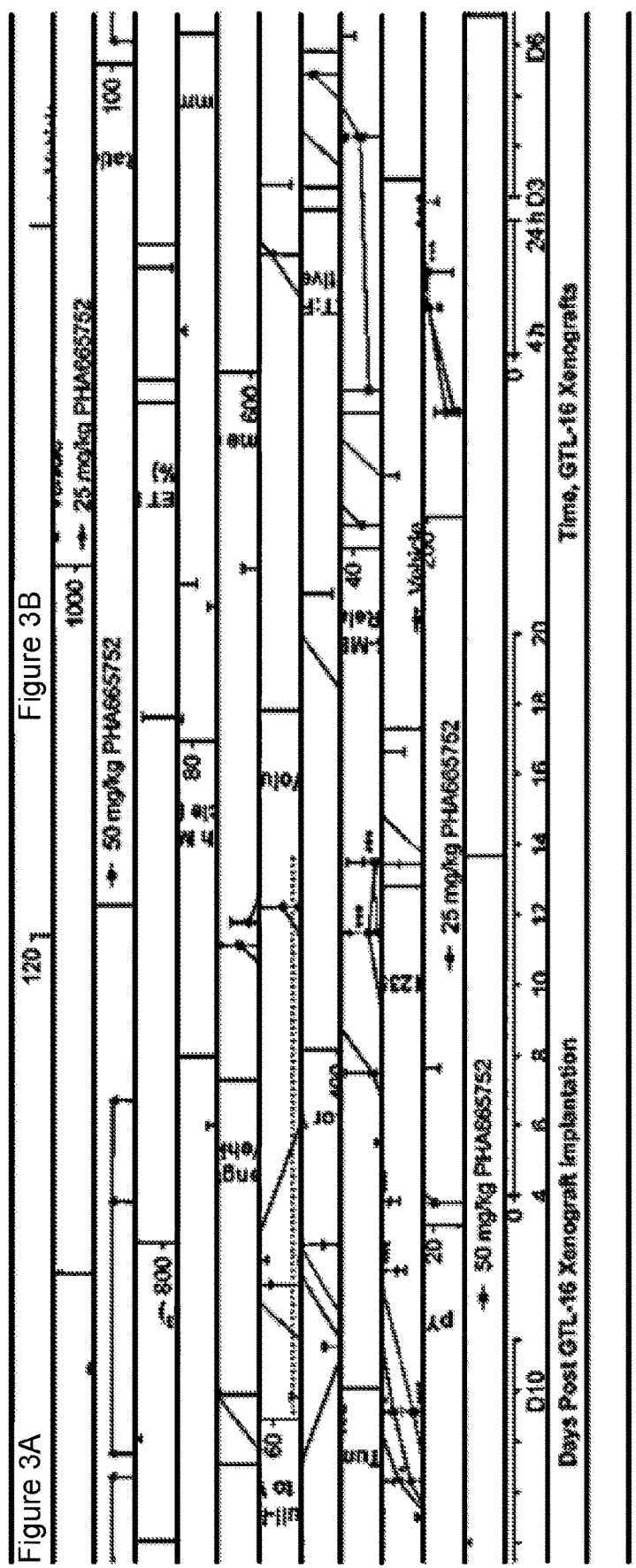

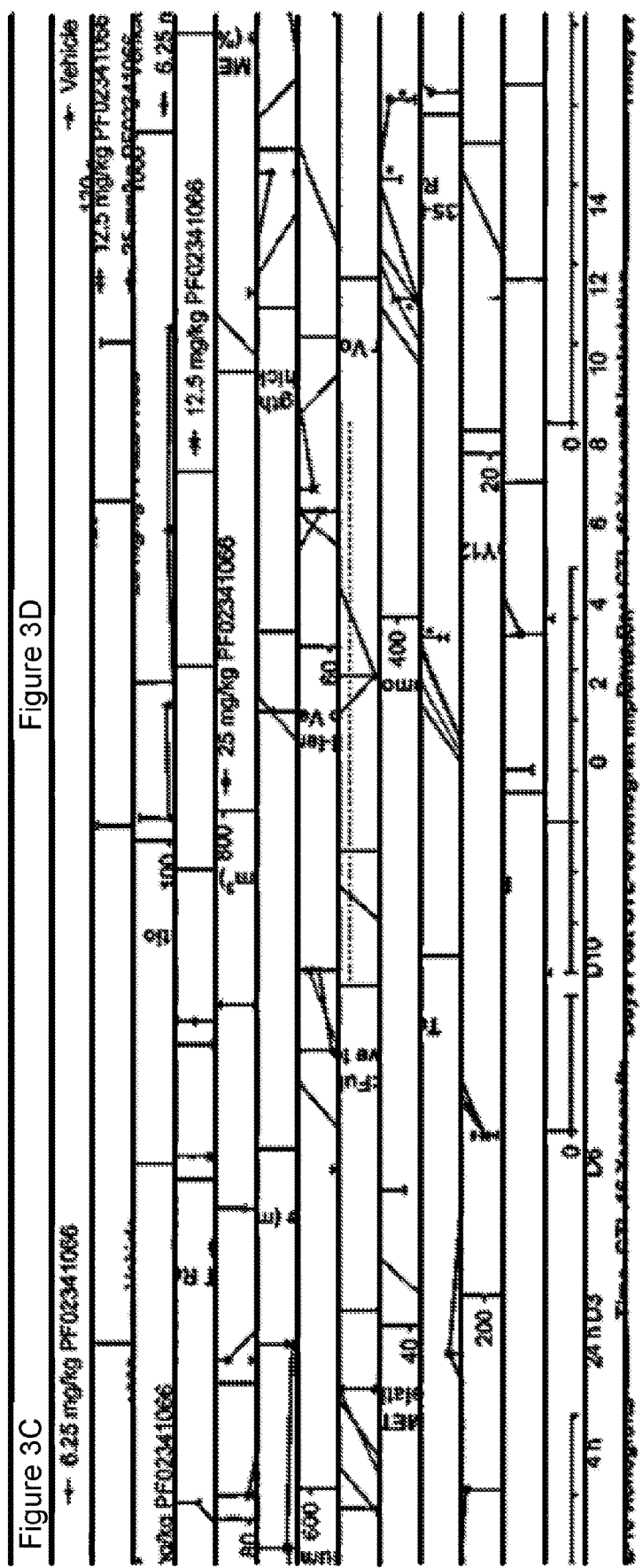

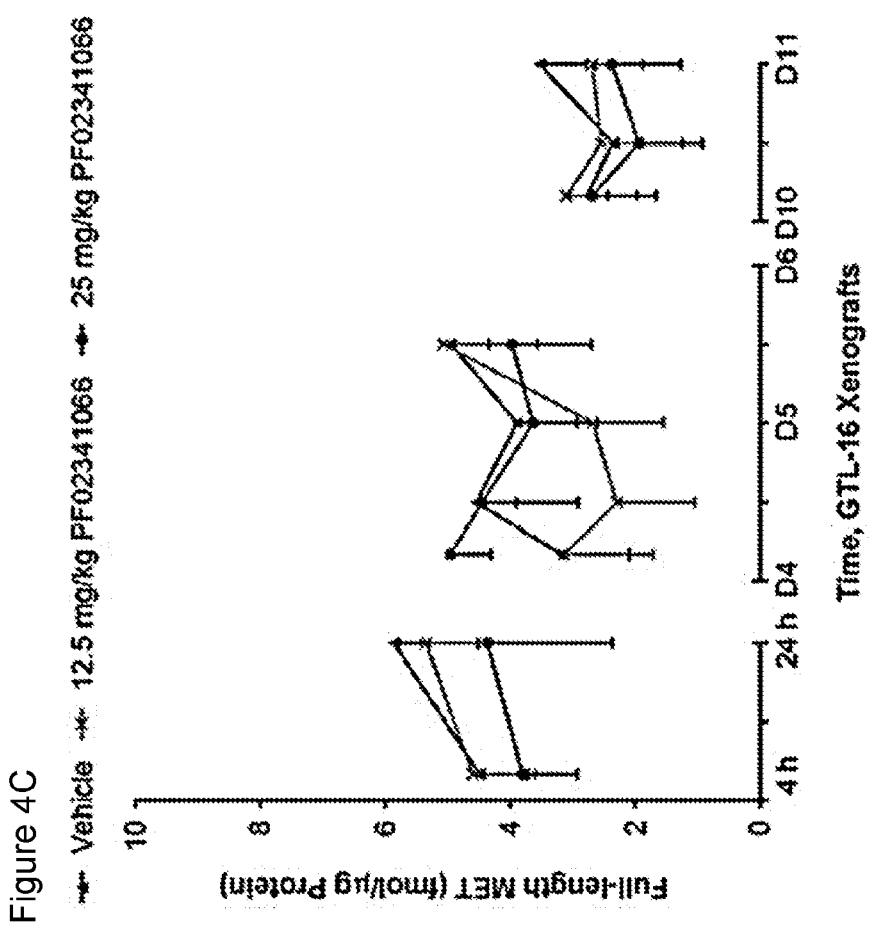

Figure 12D

```
   1  MKAPAVLAPG  ILVLLFTLVQ  RSNGECKEAL  AKSEMNVNMK  YQLPNFTAET  PIQNVILHEH
  61  HIFLGATNYI  YVLNEEDLQK  VAEYKTGPVL  EHPDCFPCQD  CSSKANLSGG  VWKDNINMAL
 121  VVDIYIDDQL  ISCGSVNRGT  CQRHVFPHNH  TADIQSEVHC  IFSPQIEEPS  QCPDCVVSAL
 181  GAKVLSSVKD  RFINFFVGNT  INSSYFPDHP  LHSISVRRLK  ETKDGFMFLT  DQSYIDVLPE
 241  FRDSYPIKIV  HAFESNNFIY  FLTVQRETLD  AQTFHTRIIR  FCSINSGLHS  YMEMPLECIL
 301  TEKRKKRSTK  KEVFNILQAA  YVSKPGAQLA  RQIGASLNDD  ILFGVFAQSK  PDSAEPMDRS
 361  AMCAFFIKYV  NDFFNKIVNK  MNVRCLQHFY  GPNHEHCFNR  TLLRNSSGCE  ARRDEYRIEF  M2
 421  TIALQRVDLF  MGQFSEVLLI  SISTFIKGDL  TIANLGTSEG  RFMQVVVSRS  GPSTPHVNFL
 481  LDSHPVSPEV  IVEHTLNQNG  YTLVITGKKI  TKIPLNGLGC  RHFQSCSQCL  SAPPFVQCGH
 541  CHDKCVRSEE  CLSGWTQQI   CLPAIYKVFP  NSAPLEGGTR  LTICGWDFGF  RRWNKFDLKK  M3
 601  TRVLLGNESC  TLTLSESTMN  TLKCTVGPAM  NKHFNMSIII  SNGHGTTQYS  TFSYVDPVIT
 661  SISPKYGPMA  GGTLLTLTGN  YLNSGNSRHI  SIGGKTCTLK  SVSNSILECY  TPAQTISTEF
 721  AVKLKIDLAN  RETSIFSYRE  DPIVYEIHPT  KSFISGGSTI  TGVGKNLNSV  SVPRMVINVH
 781  EAGRNFTVAC  QHRSNSEIIC  CTTPSLQQLN  LQLPLKTKAF  FMLDGILSKY  FDLIYVHNPV
 841  FKPFEKPVMI  SMGNEMVLEI  KGNDIDPEAV  KGEVLKVGNK  SCENIHLHSE  AVLCTVPNDL
 901  LKINSELNIE  MKQAISSTVL  GKVIVQPDQN  FTGLIAGVVS  ISTALLLLLG  FELWLKKRKQ
 961  IKDLGSELVR  YDARVHTPHL  DRLVSARSVS  PTTEMVSNES  VDYRATFPED  QFPNSSQNGS
1021  CRQVQYPLTD  MSPILTSGDS  DISSPLLQNT  VHIDLSALNP  ELVQAVQHVV  IGPSSLIVHE
1081  NEVIGRGHFG  CVYHGTLLDN  DGKKIHCAVK  SLNRITDIGE  VSQFLTEGII  MKDFSHPNVL
1141  SLLGICLRSE  GSPLVVLPYM  KHGDLRNFIR  NETHNPTVKD  LIGFGLQVAK  GMKYLASKKF
1201  VHRDLAARNC  MLDEKFTVKV  ADEGLARDMY  DKEYYSVHNK  TGAKLPVKWM  ALESLQTQKF  M1
1261  TTKSDVWSFG  VLLWELMTRG  APPYPDVNTF  DITVLLQGR   RLLQPEYCPD  PLYEVMLKCW
1321  HPKAEMRPSF  SELVSRISAI  FSTFIGEHYV  HVNATYVNVK  CVAPYPSLLS  SEDNADDEVD
1381  TRPASFWETS
```

Figure 14D

```
Human 1141  SLLGICLRSEGSPLVVLPYMKHGDLRNFIRNETHNPTVKDLIGFGLQVAKGMKYLASKKF  1200
Mouse 1139  SLLGICLRSEGSPLVVLPYMKHGDLRNFIRNETHNPTVKDLIGFGLQVAKGMKYLASKKF  1198
            SLLGICLRSEGSPLVVLPYMKHGDLRNFIRNETHNPTVKDLIGFGLQVAKGMKYLASKKF
                                                   Y1234/Y1235
                                                      **

Human 1201  VHRDLAARNCMLDEKFTVKVADFGLARDMYDKEYYSVHNKTGAKLPVKWMALESLQTQKF  1260
Mouse 1199  VHRDLAARNCMLDEKFTVKVADFGLARDMYDKEYYSVHNKTGAKLPVKWMALESLQTQKF  1258
            VHRDLAARNCMLDEKFTVKVADFGLARDMYDKEYYSVHNKTGAKLPVKWMALESLQTQKF Human 1261  TTKSDVWSFGVLLWELMTRGAPPYPDVNTFDITVYLLQGRLLQPEYCPDPLYEVMLKCW  1320
Mouse 1259  TTKSDVWSFGVLLWELMTRGAPPYPDVNTEDIT+YLLQGRLLQPEYCPD LYEVMLKCW  1318
            TTKSDVWSFGVLLWELMTRGAPPYPDVNTFDITIYLLQGRLLQPEYCPDALYEVMLKCW
                                       Y1356
                                         *

Human 1321  HPKAEMRPSFSELVSRISAIFSTFIGEHYVHVNATYVNVKCVAPYPSLLSSEDNADDEVD  1380
Mouse 1319  HPKAEMRPSFSELVSRISSIFSTFIGEHYVHVNATYVNVKCVAPYPSLL S+DN D E +  1378
            HPKAEMRPSFSELVSRIS+IFSTFIGEHYVHVNATYVNVKCVAPYPSLLPSQDNIDGEGN
```

ANTI-PY1235-MET IMMUNOLOGICAL BINDING REAGENT

CROSS-REFERENCE TO RELATED APPLICATIONS

This application is the U.S. national phase of International Application No. PCT/US2017/022783 filed on Mar. 17, 2017, and published on Sep. 21, 2017 as International Publication No. WO 2017/161169 A1, which application claims priority to and the benefit of U.S. Provisional Application No. 62/309,920 filed Mar. 17, 2016, the contents of all of which are incorporated herein by reference in their entireties.

STATEMENT AS TO RIGHTS TO INVENTIONS MADE UNDER FEDERALLY SPONSORED RESEARCH AND DEVELOPMENT

This invention was made with government support under Contract No. HHSN261200800001E, awarded by the National Cancer Institute, National Institutes of Health. The government has certain rights in the invention.

REFERENCE TO THE SEQUENCE LISTING

Applicant hereby makes reference to the Sequence Listing that is contained in the file "077867-1040168-627100PC_SequenceListing.TXT" (32 kB; created on Sep. 17, 2018), the contents of which are incorporated herein by reference.

BACKGROUND OF THE INVENTION

The receptor tyrosine kinase MET is an important drug target for treatment of various diseases including diseases mediated by dysregulated cell proliferation (e.g., cancer). A key event involved in MET activation and/or signaling is phosphorylation at the Y1235 position. However, MET activation and/or signaling is difficult to assess due to the lack of specific binding reagents that detect phosphorylation at Y1235 of MET without cross-reacting with one or more other phosphorylation sites. The present invention addresses this and other needs.

BRIEF SUMMARY OF THE INVENTION

In a first aspect, the present invention provides an antibody that specifically binds to pY1235-MET, or a fragment thereof that contains pY1235, wherein the antibody comprises a heavy chain variable region and a light chain variable region, wherein the heavy chain variable region and the light chain variable region each comprise the following three complementary determining regions (CDRs): CDR1, CDR2 and CDR3; wherein: i) the CDR1 of the heavy chain variable region comprises the amino acid sequence of SEQ ID NO:3; ii) the CDR2 of the heavy chain variable region comprises the amino acid sequence of SEQ ID NO:4; iii) the CDR3 of the heavy chain variable region comprises an amino acid sequence of SEQ ID NO:5; iv) the CDR1 of the light chain variable region comprises the amino acid sequence of SEQ ID NO:6; v) the CDR2 of the light chain variable region comprises the amino acid sequence of SEQ ID NO:7; vi) the CDR3 of the light chain variable region comprises the amino acid sequence of SEQ ID NO:8.

In a second aspect, the present invention provides a polynucleotide encoding an antibody that specifically binds to pY1235-MET, or a fragment thereof that contains pY1235. In a third aspect, the present invention provides an expression cassette comprising the foregoing polynucleotide of claim operably linked to a promoter. In a fourth aspect, the present invention provides a host cell comprising the foregoing expression cassette. In a fifth aspect, the present invention provides a method of making an antibody that specifically binds to pY1235-MET, or a fragment thereof that contains pY1235, comprising culturing the foregoing host cell and purifying the antibody from spent culture media or cultured host cell lysate. In a sixth aspect, the present invention provides a method of specifically detecting a target antigen, wherein the target antigen comprises pY1235-MET, or a fragment thereof that contains pY1235, in a sample comprising: contacting the sample with the foregoing antibody, thereby forming an antibody:target antigen immunoconjugate, if present; and detecting the presence or absence of the immunoconjugate.

In a seventh aspect, the present invention provides a method for identifying a test compound as an inhibitor of MET, the method comprising: contacting a cell or extract thereof with the test compound; specifically detecting pY1235-MET, or a fragment thereof containing pY1235, in the cell or extract using the foregoing method; and identifying the test compound as an inhibitor of MET if: −pY1235-MET, or the fragment thereof containing pY1235, or—a ratio of pY1235-MET, or the fragment thereof, to total MET, is reduced relative to a control cell or extract that has not been contacted with the teat compound.

In an eighth aspect, the present invention provides a method of identifying a subject as indicated for treatment with a MET inhibitor, the method comprising: providing one or more samples from the subject; specifically detecting pY1235-MET, or a fragment thereof, in one of the sample(s) or a portion thereof using an anti-pY1235-MET immunological binding reagent; and identifying the subject as indicated for treatment with the MET inhibitor if: pY1235 or a ratio of pY1235 to total MET is high relative to a control sample or reference value; pY1356 or a ratio of pY1356 to total MET is high relative to a control sample or reference value; pY1234/1235 or a ratio of pY1234/1235 to total MET is high relative to a control sample or reference value; and/or full length MET or a ratio of full length MET to total MET is high relative to a control sample or reference value.

In a ninth aspect, the present invention provides a method of monitoring a MET inhibitor treatment of a subject in need thereof, the method comprising: administering a first dose of the MET inhibitor treatment to the subject providing a first sample from the subject; specifically detecting pY1235-MET, or fragments thereof containing pY1235, in the first sample or a portion thereof using an anti-pY1235-MET immunological binding reagent; administering a second dose of the MET inhibitor treatment to the subject; providing a second sample from the subject; and specifically detecting pY1235-MET, or fragments thereof containing pY1235, in the second sample or a portion thereof using an anti-pY1235-MET immunological binding reagent.

Definitions

"MET" refers to the receptor tyrosine kinase alternatively known as the hepatocyte growth factor receptor (HGFR). The nucleic acid and amino acid sequences of human MET are recorded, e.g., as GenBank Accession Nos. NM_000245.2 and NP_000236.2, respectively.

"Antibodies" exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to VH-CH by a disulfide bond. The F(ab)'$_2$ may be reduced under mild conditions to break the disulfide linkage in the hinge region thereby converting the (Fab')$_2$ dimer into a Fab' monomer. The Fab' monomer is essentially a Fab with part of the hinge region (see, W. E. Paul, ed., Fundamental Immunology, Raven Press, N.Y. (1993), for a more detailed description of these and other antibody fragments). While various antibody fragments are defined in terms of the digestion of an intact antibody, one of skill will appreciate that such Fab' fragments may be synthesized de novo either chemically or by utilizing recombinant DNA methodology.

For convenience of reference, as used herein, the term "antibody" includes whole (sometimes referred to herein as "intact") antibodies, antibody fragments that retain antigen recognition and binding capability, whether produced by the modification of whole antibodies or synthesized de novo using recombinant DNA methodologies, monoclonal antibodies, polyclonal antibodies, and antibody mimetics, unless otherwise required by context. The antibody may be an IgM, IgG (e.g. IgG$_1$, IgG$_2$, IgG$_3$ or IgG$_4$), IgD, IgA or IgE). In some embodiments, the antibody is a rabbit IgG.

The term "antibody fragments" means molecules that comprise a portion of an intact antibody, generally the antigen binding or variable region of the intact antibody. Examples of antibody fragments include Fab, Fab', F(ab')2, and Fv fragments; helix-stabilized antibodies (see, e.g., Arndt et al., J Mol Biol 312:221-228 (2001); diabodies (see below); single-chain antibody molecules ("scFvs," see, e.g., U.S. Pat. No. 5,888,773); disulfide stabilized antibodies ("dsFvs", see, e.g., U.S. Pat. Nos. 5,747,654 and 6,558,672), and domain antibodies ("dAbs," see, e.g., Holt et al., Trends Biotech 21(11):484-490 (2003), Ghahroudi et al., FEBS Lett. 414:521-526 (1997), Lauwereys et al., EMBO J 17:3512-3520 (1998), Reiter et al., J. Mol. Biol. 290:685-698 (1999), Davies and Riechmann, Biotechnology, 13:475-479 (2001)).

As used herein, the term "anti-pY1235-MET" in reference to an immunological binding reagent such as an antibody, includes reference to an immunological binding reagent that is generated against and/or specifically binds to pY1235-MET, which refers to the phosphorylated form of the tyrosine residue at amino acid position 1235 of human MET. The immunological binding reagents can be cross-reactive with MET proteins from different mammalian species, e.g., human, mouse, non-human primate. In some embodiments, the anti-pY1235-MET immunological binding reagent specifically binds to both full-length and one or more fragments of pY1235-MET, wherein the fragments contain pY1235. In some embodiments, the fragment is a truncated form of pY1235-MET, including but not limited to, those having a molecular weight of about 140 kDa, 130 kDa, 85 kDa, 75 kDa, or 50 kDa (see, e.g., Prat et al., Mol Cell Biol. 1991 December; 11(12):5954-62). In some cases, the truncation is a C-terminal truncation. In some cases, the truncation is an N-terminal truncation. In some cases, the truncation is a C-terminal truncation and an N-terminal truncation. Additionally, or alternatively, the immunological binding reagent can specifically bind to a single chain of the MET heterodimer containing pY1235. In some cases, the single chain is further N-, C-, or N- and C-terminally truncated. The fragment can be a polypeptide (e.g., chemically synthesized polypeptide) that contains about or contains at least about 6, preferably about or at least about 8, more preferably about or at least about 10, or more preferably about or at least about 12 contiguous amino acids of pY1235-MET including pY1235. In some cases, the fragment is from 8-12, from 10-12, from 6 to 40, or from 10 to 40 contiguous amino acids of pY1235-Met, including pY1235. As such, anti-pY1235-MET can be used to detect a total level of pY1235, whether present as full-length pY1235-MET or fragments thereof, in a sample.

Similarly, anti-pY1234/1235-MET refers to an immunological binding reagent that specifically binds to pY1234-MET and pY1235-MET. In some cases, anti-pY1234/1235-MET also binds to fragments of MET that contain one or both of pY1234 and pY1235. As such, anti-pY1234/1235-MET can be used to detect a total level of MET that is phosphorylated at either Y1234 or Y1235 or both. In some embodiments, anti-pY1234/1235-MET can also be used to detect a total level of pY1234/1235, whether present as full-length pY1234/1235-MET or fragments thereof that are phosphorylated at either Y1234 or Y1235 or both in a sample. The fragments that phosphorylated at either Y1234 or Y1235 or both can be N- or C-terminal truncations of MET, single chains of the MET heterodimer, or a combination thereof. Or, the fragments can be peptides (e.g., chemically synthesized polypeptide) that contains about or contains at least about 6, preferably about or at least about 8, more preferably about or at least about 10, or more preferably about or at least about 12 contiguous amino acids of pY1234/1235-MET including pY1234 and/or pY1235.

Similarly, anti-pY1356-MET refers to an immunological binding reagent that specifically binds to pY1356-MET. In some cases, anti-pY1356-MET also binds to fragments of MET that contain pY1356. As such, anti-pY1356-MET can be used to detect a total level of MET that is phosphorylated at Y1356. In some embodiments, anti-pY1356-MET can also be used to detect a total level of pY1356-MET and fragments thereof that are phosphorylated at pY1356. Thus, in some embodiments, anti-pY1356-MET can be used to detect a total level of pY1356, whether present as full-length pY1356-MET or fragments thereof, in a sample. The fragments that phosphorylated at Y1356 can be N- or C-terminal truncations of MET, single chains of the MET heterodimer, or a combination thereof. Or, the fragments can be peptides (e.g., chemically synthesized polypeptide) that contains about or contains at least about 6, preferably about or at least about 8, more preferably about or at least about 10, or more preferably about or at least about 12 contiguous amino acids of MET including pY1356.

The term "diabodies" refers to small antibody fragments with two antigen-binding sites, which fragments comprise a variable heavy domain ("V$_H$" or "VH") connected to a variable light domain ("V$_L$" or "VL") in the same polypeptide chain (V$_H$-V$_L$). By using a linker that is too short to allow pairing between the two domains on the same chain, the domains are forced to pair with the complementary domains of another chain and create two antigen-binding sites. Diabodies and their production are described more fully in, for example, EP 404,097; WO 93/11161; and Holliger et al., Proc. Natl. Acad. Sci. USA, 90: 6444-6448 (1993).

Typically, an immunoglobulin has a heavy and light chain. Each heavy and light chain contains a constant region and a variable region, (the regions are also known as "domains"). Light and heavy chain variable regions contain a "framework" region interrupted by three hypervariable regions, also called "complementarity-determining regions" or "CDRs". The extent of the framework region and CDRs have been defined. (see, Kabat, E., et al., SEQUENCES OF PROTEINS OF IMMUNOLOGICAL INTEREST, U.S. Department of Health and Human Services, (1987), which is hereby incorporated by reference). The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a VH CDR3 is located in the variable domain of the heavy chain of the antibody in which it is found, whereas a VL CDR1 is the CDR1 from the variable domain of the light chain of the antibody in which it is found.

The term "immunological binding reagent" refers to a molecule that binds to a target antigen, wherein the binding is mediated by one or more antibody CDRs. The term "immunological binding reagent" includes antibodies, antibody mimetics, and antibody like binding peptidomimetics. Certain of these "antibody mimetics" use non-immunoglobulin protein scaffolds as alternative protein frameworks for the variable regions and/or CDRs of antibodies. For example, Ku et al. (*Proc. Natl. Acad. Sci. USA.* 92 (14): 6552-6556 (1995)) discloses an alternative to antibodies based on cytochrome b562 in which two of the loops of cytochrome b562 were randomized and selected for binding against bovine serum albumin. The individual mutants were found to bind selectively with BSA similarly with anti-BSA antibodies.

U.S. Pat. Nos. 6,818,418 and 7,115,396 disclose an antibody mimetic featuring a fibronectin or fibronectin-like protein scaffold and at least one variable loop. Known as Adnectins, these fibronectin-based antibody mimetics exhibit many of the same characteristics of natural or engineered antibodies, including high affinity and specificity for any targeted ligand. The structure of these fibronectin-based antibody mimetics is similar to the structure of the variable region of the IgG heavy chain. Therefore, these mimetics display antigen binding properties similar in nature and affinity to those of native antibodies. Further, these fibronectin-based antibody mimetics exhibit certain benefits over antibodies and antibody fragments. For example, these antibody mimetics do not rely on disulfide bonds for native fold stability, and are, therefore, stable under conditions which would normally break down antibodies. In addition, since the structure of these fibronectin-based antibody mimetics is similar to that of the IgG heavy chain, the process for loop randomization and shuffling may be employed in vitro that is similar to the process of affinity maturation of antibodies in vivo.

Beste et al, (*Proc. Natl. Acad. Sci. U.S.A.* 96 (5):1898-1903 (1999)) disclose an antibody mimetic based on a lipocalin scaffold (Anticalin®). Lipocalins are composed of a β-barrel with four hypervariable loops at the terminus of the protein. The loops were subjected to random mutagenesis and selected for binding with, for example, fluorescein. Three variants exhibited specific binding with fluorescein, with one variant showing binding similar to that of an anti-fluorescein antibody. Further analysis revealed that all of the randomized positions are variable, indicating that Anticalin® would be suitable to be used as an alternative to antibodies. Thus, Anticalins® are small, single chain peptides, typically between 160 and 180 residues, which provides several advantages over antibodies, including decreased cost of production, increased stability in storage and decreased immunological reaction.

U.S. Pat. No. 5,770,380 discloses a synthetic antibody mimetic using the rigid, non-peptide organic scaffold of calixarene, attached with multiple variable peptide loops used as binding sites. The peptide loops all project from the same side geometrically from the calixarene, with respect to each other. Because of this geometric confirmation, all of the loops are available for binding, increasing the binding affinity to a ligand. However, in comparison to other antibody mimetics, the calixarene-based antibody mimetic does not consist exclusively of a peptide, and therefore it is less vulnerable to attack by protease enzymes. Neither does the scaffold consist purely of a peptide, DNA or RNA, meaning this antibody mimetic is relatively stable in extreme environmental conditions and has a long life span. Further, since the calixarene-based antibody mimetic is relatively small, it is less likely to produce an immunogenic response.

Murali et al. (*Cell Mol Biol* 49 (2):209-216 (2003)) describe a methodology for reducing antibodies into smaller peptidomimetics, they term "antibody like binding peptidomimetics" (ABiP) which may also be useful as an alternative to antibodies.

References to "VH" or a "$V_H$" refer to the variable region of an immunoglobulin heavy chain, including an Fv, scFv, dAb, dsFv or Fab. References to "VL" or a "$V_L$" refer to the variable region of an immunoglobulin light chain, including of an Fv, scFv dsFv, dAb, or Fab.

The term "Fv" refers to the variable domains of the heavy chain and of the light chain of an antibody. The phrase "single chain Fv" or "scFv" refers to an antibody in which the variable domains of the heavy chain and of the light chain of a traditional two chain antibody have been joined to form one chain. Optionally, a linker (usually a peptide) is inserted between the two chains to allow for proper folding and creation of an active binding site. If a linker is present, it is excluded for purposes of comparing the percentage of sequence identity between a given VH or VL chain and a different VH or VL chain.

Antibodies of the invention include multispecific antibodies. Multispecific antibodies have more than one binding specificity. In the present invention, at least one binding site of such multispecific antibodies has the binding specificity, i.e., binds to the same epitope, as the anti-pY1235-MET antibody. In some embodiments, at least one binding site of a multi-specific antibody has the heavy chain CDRs and/or light chain CDRs of the anti-pY1235-MET antibody. The term "bispecific" antibody as used herein refers to an antibody that has at two binding sites each of which bind to different epitopes of the same antigen or a different antigen.

The term "valent" as used herein refers to a specified number of binding sites in an antibody molecule. A "multivalent" antibody has two or more binding sites. Thus, the terms "bivalent", "trivalent", and "tetravalent" refers to the presence of two binding sites, three binding sites, and four binding sites, respectively. A bispecific antibody according to the invention is at least bivalent and may be trivalent, tetravalent, or otherwise multivalent. Multispecific antibodies of the invention, e.g., bispecific antibodies, include, for example, multivalent single chain antibodies, diabodies and triabodies, as well as antibodies having a constant domain structure such as that of full length antibodies, to which further antigen-binding sites (e.g., single chain Fv, a $V_H$ domain and/or a $V_L$ domain, Fab, or (Fab)$_2$) are linked, typically via one or more peptide linkers.

An antibody immunologically reactive with a particular antigen can be generated by recombinant methods such as selection of libraries of recombinant antibodies in phage or similar vectors, see, e.g., Huse, et al., *Science* 246:1275-1281 (1989); Ward, et al., *Nature* 341:544-546 (1989); and Vaughan, et al., *Nature Biotech.* 14:309-314 (1996), or by immunizing an animal with the antigen or with DNA encoding the antigen.

The extent of the framework region and CDRs have been defined. The sequences of the framework regions of different light or heavy chains are relatively conserved within a species. The framework region of an antibody, that is the combined framework regions of the constituent light and heavy chains, serves to position and align the CDRs in three dimensional space.

The antibodies of the present invention can be encoded by nucleic acid sequences that correspond to a human germline sequence. The term "corresponding human germline sequence" refers to the nucleic acid sequence encoding a human variable region amino acid sequence or subsequence that shares the highest determined amino acid sequence identity with a reference variable region amino acid sequence or subsequence in comparison to all other evaluated variable region amino acid sequences encoded by human germline immunoglobulin variable region sequences. The corresponding human germline sequence can also refer to the human variable region amino acid sequence or subsequence with the highest amino acid sequence identity with a reference variable region amino acid sequence or subsequence in comparison to all other evaluated variable region amino acid sequences. The corresponding human germline sequence can be framework regions only, complementary determining regions only, framework and complementary determining regions, a variable segment, or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 92%, 94%, 96%, 98%, 99% sequence identity with the reference variable region nucleic acid or amino acid sequence. Corresponding human germline sequences can be determined, for example, through the publicly available international ImMunoGeneTics database (IMGT) (on the worldwide web at imgt.cines.fr/) and V-base (on the worldwide web at vbase.mrc-cpe.cam.ac.uk).

The term "linker peptide" includes reference to a peptide within an immunological binding reagent such as an antibody binding fragment (e.g., Fv fragment) which serves to indirectly bond the variable domain of the heavy chain to the variable domain of the light chain.

A "targeting moiety" is the portion of an immunoconjugate intended to target the immunoconjugate to a cell of interest. Typically, the targeting moiety is an immunological binding reagent such as an antibody, a scFv, a dsFv, an Fab, or an F(ab')$_2$.

A "detectable label" means, with respect to an immunoconjugate, a portion of the immunoconjugate which has a property rendering its presence detectable. For example, the immunoconjugate may be labeled with a fluorophore (e.g., fluorescent dye), a chromophore (e.g., a fluorescent or non-fluorescent dye), a luminescent agent, an enzyme (e.g., a peroxidase or phosphatase), a ligand (e.g., a biotin or avidin or streptavidin), or radioactive isotope which permits cells, tissues, or samples therefrom in which the immunoconjugate is present to be detected in immunohistochemical assays.

The term "conjugated to," in relation to an immunological binding reagent or detectable label, means that the immunological binding reagent is fused to (e.g., by recombinant expression) or conjugated to (e.g., chemically attached to) the therapeutic moiety or detectable label, directly or through a linker. A detectable label conjugated to an immunological binding reagent is heterologous with respect to the immunological binding reagent.

An "expression cassette" comprises a nucleotide sequence encoding a molecule of interest, which is operably linked to a promoter.

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups in Table A each contain amino acids that are conservative substitutions for one another:

TABLE A

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, Proteins: Structures and Molecular Properties, W. H. Freeman and Company, New York (2nd Ed., 1992).

The terms "substantially similar" in the context of a peptide indicates that a peptide comprises a sequence with at least 90%, for example at least 95%, sequence identity to the reference sequence over a comparison window of 7-20 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The phrase "disulfide bond" or "cysteine-cysteine disulfide bond" refers to a covalent interaction between two cysteines in which the sulfur atoms of the cysteines are oxidized to form a disulfide bond. The average bond energy of a disulfide bond is about 60 kcal/mol compared to 1-2 kcal/mol for a hydrogen bond. In the context of this invention, the cysteines which form the disulfide bond are within the framework regions of the single chain antibody and serve to stabilize the conformation of the antibody.

The terms "conjugating," "joining," "bonding" or "linking" refer to making two polypeptides into one contiguous polypeptide molecule. In the context of the present invention, the terms include reference to joining an antibody moiety to an effector molecule (EM). The linkage can be either by chemical or recombinant means. Chemical means refers to a reaction between the antibody moiety and the effector molecule such that there is a covalent bond formed between the two molecules to form one molecule.

As used herein, "recombinant" includes reference to a protein produced using cells that do not have, in their native state, an endogenous copy of the DNA able to express the protein. The cells produce the recombinant protein because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, underexpressed or not expressed at all.

As used herein, "nucleic acid" or "nucleic acid sequence" includes reference to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof as well as conservative variants, i.e., nucleic acids present in wobble positions of codons and variants that, when translated into a protein, result in a conservative substitution of an amino acid.

As used herein, "encoding" with respect to a specified nucleic acid, includes reference to nucleic acids which comprise the information for translation into the specified protein. The information is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (*Proc. Nat'l. Acad. Sci. USA* 82:2306-2309 (1985), or the ciliate Macronucleus, may be used when the nucleic acid is expressed in using the translational machinery of these organisms.

The phrase "fusing in frame" refers to joining two or more nucleic acid sequences which encode polypeptides so that the joined nucleic acid sequence translates into a single chain protein which comprises the original polypeptide chains.

As used herein, "expressed" includes reference to translation of a nucleic acid into a protein. Proteins may be expressed and remain intracellular, become a component of the cell surface membrane or be secreted into the extracellular matrix or medium.

By "host cell" is meant a cell which can support the replication or expression of the expression vector. Host cells may be prokaryotic cells such as *E. coli*, or eukaryotic cells such as yeast, insect, amphibian, or mammalian cells.

The phrase "phage display library" refers to a population of bacteriophage, each of which contains a foreign cDNA recombinantly fused in frame to a surface protein. The phage display the foreign protein encoded by the cDNA on its surface. After replication in a bacterial host, typically *E. coli*, the phage which contain the foreign cDNA of interest are selected by the expression of the foreign protein on the phage surface.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, for example at least 80%, or at least 90-95% nucleotide or amino acid residue identity, when compared and aligned for maximum correspondence, as measured using one of the following sequence comparison algorithms or by visual inspection. The substantial identity can exist over a region of the sequences that is at least about 50 residues in length, for example, over a region of at least about 100 residues, or over at least about 150 residues. In one embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math*, 2:482 (1981), by the homology alignment algorithm of Needleman & Wunsch, *J. Mol. Biol.* 48:443 (1970), by the search for similarity method of Pearson & Lipman, *Proc. Nat'l, Acad. Sci, USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information (on the internet by entering "www." followed by "ncbi.nlm.nih.gov/"). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci, USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence (e.g., SEQ ID NOS:1-12) if the smallest sum probability in a comparison of the test nucleic acid to the reference nucleic acid is less than about 0.1, for example less than about 0.01, or less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The term "in vivo" includes reference to inside the body of the organism from which the cell was obtained. "Ex vivo" and "in vitro" means outside the body of the organism from which the cell was obtained.

The term "selectively reactive" or "specifically binds" refers, with respect to an antigen, the preferential association of an immunological binding reagent (e.g., antibody), in whole or part, with a cell or tissue bearing that antigen and not to cells or tissues lacking that antigen. It is, of course, recognized that a certain degree of non-specific interaction may occur between a molecule and a non-target cell or tissue. Nevertheless, selective reactivity, may be distinguished as mediated through specific recognition of the antigen. Although selectively reactive immunological binding reagents bind antigen, they may do so with low affinity. On the other hand, specific binding results in a much stronger association between the immunological binding reagent and cells bearing the antigen than between the bound immunological binding reagent and cells lacking the antigen. Specific binding typically results in greater than 2-fold, for example greater than 5-fold, or greater than 10-fold and can result in greater than 100-fold or 1000-fold increase in amount of bound immunological binding reagent (per unit time) to a cell or tissue bearing pY1235-MET as compared to a cell or tissue lacking pY1235-MET. Specific binding to a protein or a specific epitope of a protein under such conditions requires an immunological binding reagent that is selected for its specificity for a particular protein. A variety of immunoassay formats are appropriate for selecting immunological binding reagents specifically immunoreactive with a particular protein or a specific epitope of a protein. For example, solid-phase ELISA immunoassays are routinely used to select monoclonal antibodies specifically immunoreactive with a protein or a specific epitope of a protein (e.g., pY1235-MET). See Harlow & Lane, ANTIBODIES, A LABORATORY MANUAL, Cold Spring Harbor Publications, New York (1988), for a description of immunoassay formats and conditions that can be used to determine specific immunoreactivity.

The term "immunologically reactive conditions" includes reference to conditions which allow an immunological binding reagent (e.g., antibody) that specifically binds a particular epitope to bind to that epitope to a detectably greater degree than, and/or to the substantial exclusion of, binding to substantially all other epitopes. Immunologically reactive conditions are dependent upon the format of the binding reaction and typically are those utilized in immunoassay protocols or those conditions encountered in vivo. See Harlow & Lane, supra, for a description of immunoassay formats and conditions. The immunologically reactive conditions employed in the methods of the present invention are generally "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

BRIEF DESCRIPTION OF THE DRAWINGS

FIG. 1. Development of immunoassays for full-length MET and its key phosphorylated species. (A) Schematic of an exemplary MET immunoassay: a capture antibody (catalog number AF276) specific to the extracellular domain of MET binds and traps MET from tissue lysates, then four different reporter monoclonal antibodies (e.g., clone D26 to pY1234/1235, clone 23111 to pY1235, clone 7334 to pY1356 and clone L41G3 to the C-terminus) can be used to detect phosphorylated and full-length MET. (B) Specificity of anti-pY1235-MET (clone 23111; developed in this study) is shown by immunofluorescence staining of formalin-fixed, paraffin-embedded GTL-16, HT29, and A549 cancer cells treated in vitro with 100 nM PF02341066 or 100 mM sorafenib for 4 h. (C) Representative calibration curves from the full-length MET (0.3-40 pM), pY1234/1235-MET (0.3-40 pM), pY1235-MET (1.5-200 pM), and pY1356-MET immunoassays (3.25-200 pM). The same rMET protein can be used as a calibrator in all four immunoassays and levels have been converted to log pM. (D) MET levels in four different human cancer cell lines routinely used in MET preclinical xenograft studies; two separate GTL-16 and U87 xenograft samples were used. Cell lysates were diluted to 31.25-2000 ng/well in a 100 µL volume; MET levels were back-calculated to fmol/µg total loaded protein.

FIG. 3. Reduction of GTL-16 tumor growth and MET phosphorylation by MET RTK inhibitors. (A) Tumor volume of GIL-16 tumor xenografts in mice treated with PHA665752 at daily doses of 0, 25 and 50 mg/kg IP starting 10 days after implantation; n=5-28 per dose per time point. (B) The intratumoral pY1235-MET:MET ratio during 10 days of daily treatment with PHA665752; n=5-6 per dose per time point. Tumor samples were analyzed at 4 and 24 h after dose 1, and 4 h after dose 3 (D3), 8 (D8) and 10 (D10). (C) Tumor volume of GTL-16 xenografts in mice treated with PF02341066 at daily doses of 0, 6.25, 12.5, and 25 mg/kg PO starting at 4 days after implantation. Error bars are mean±SD, groups n=4-30 per dose per time point. (D) The pY1235-MET:MET ratio during 10 days of daily treatment with PF02341066. Tumor samples were analyzed at 4 and 24 h after dose 1 and 4 h after dose 3 (D3), 6 (D6) and 10 (D10). Mean±SD, groups n=2-6 per dose per time point. For (A) and (C), single asterisk (*) p<0.05 and triple asterisk (***) p<0.001 compared to vehicle group by unpaired Student's t-test. For (B) and (D), the dotted line indicates the Least Significant Change (LSC) in pMET:MET ratio from the vehicle-treated group of 45%; changes larger than this are attributed to drug effect.

DETAILED DESCRIPTION OF THE INVENTION

1. Introduction

Figure 2A:
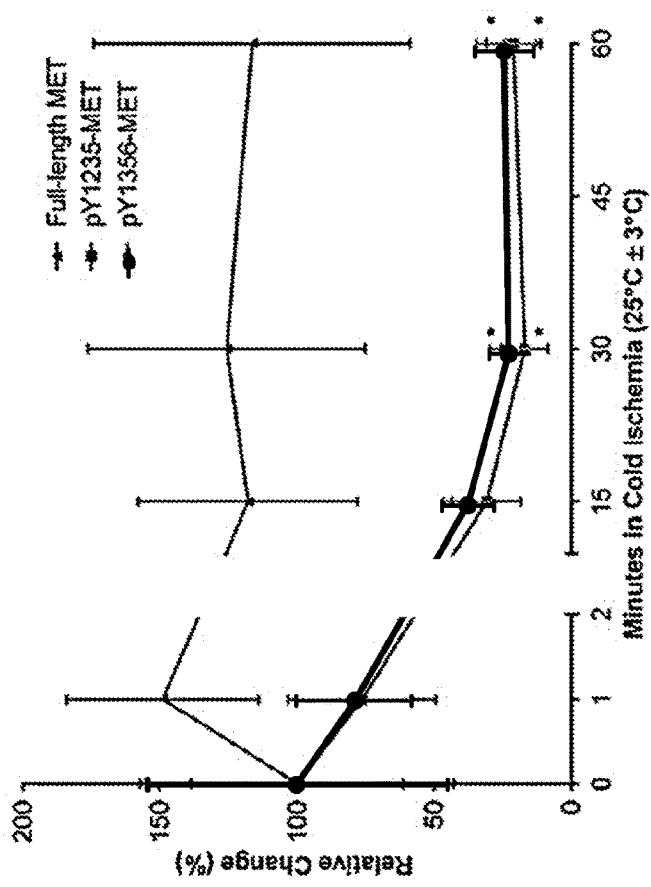
FIG. 2. Stability of full-length MET and pMET in core needle biopsies of xenografted SNU5 tumors. Core needle biopsies were incubated in saline solution for 0 (baseline, 100%), 1, 15, 30, or 60 min of (A) cold ischemia or (B) warm ischemia. (C) Follow-up study of stability of full-length and pY1234/1235-MET in core biopsies during 0, 1, 2, 3, 4, 5, and 8 min of cold ischemia. For all graphs, error bars are mean±SD, n=4-6; a single asterisk (*) denotes P<0.05 from baseline by Student's t test. (D) Western blot of extracts of core biopsies after 0, 1, 15, 30 or 60 min of cold ischemia probed with the indicated antibodies.

The receptor tyrosine kinase (RTK) MET (MET proto-oncogene, receptor tyrosine kinase; hepatocyte growth factor receptor [HGFR]) is an important drug target because of its roles in cancer progression, metastasis, and acquired resistance to epidermal growth factor receptor (EGFR) inhibitors (1, 2). Aberrant MET signaling can occur through ligand-dependent as well as ligand-independent mechanisms (3). Consistent with multiple mechanisms of MET dysregulation, there are multiple therapeutic strategies to target MET, including HGF or MET neutralizing antibodies, decoy receptors, small-molecule tyrosine kinase inhibitors (TKIs), and allosteric inhibitors of MET activation (4-7). Drugs from each mechanistic class are currently under clinical investigation, both as single agents and in combination with other treatments (8-11). Many of these clinical trials require patient selection based on immunohistochemical and/or gene copy number assessment of MET (11, 12). However, these diagnostic assays cannot provide quantitative pharmacodynamic (PD) information (i.e., magnitude and duration of target modulation) to guide clinical development, nor can they distinguish between phosphorylated epitopes of full-length MET and its degradation products (13).

MET receptor activity is regulated by phosphorylation of a number of sites including Y1234 and Y1235 in the activation loop, which are crucial for regulation of kinase activity; the carboxy-terminal Y1349 and Y1356 in the multifunctional docking site required to recruit cytoplasmic signal transducers and adaptors; and S975 and Y1003 in the juxta-membrane region, phosphorylation of which causes MET ubiquitylation and degradation (5, 8, 14, 15). Based on this understanding of MET signaling, MET immunoassays were designed as described herein to measure full-length, transmembrane MET protein and three key phosphospecies involved in its signal transduction: pY1234/1235-MET, pY1235-MET, and pY1356-MET. These assays were designed for measurement of wild-type MET, because mutations account for only 10%-30% of all cancer subtypes where MET acts as a driver (compilation at www.vai.org/Met/Index.aspx) (16). After validating the immunoassays and specimen collection and processing methods in preclinical models, the clinical suitability of the immunoassays for studying MET in diseases without gene amplification was illustrated herein in a case of MET-driven hereditary papillary renal cell carcinoma (HPRC).

The present invention demonstrates the successful isolation from an immunized rabbit of a monoclonal antibody (i.e., antibody #23111) that specifically binds a phosphorylated tyrosine at position 1235 of human MET and/or fragments of human MET that contain pY1235. In some embodiments, the antibody specifically binds to pY1235-MET, and/or fragments of human MET that contain pY1235, but is independent of phosphorylated or un-phosphorylated Y1230 or Y1234, or any combination thereof, or all thereof. In some embodiments, the antibody specifically binds to pY1235-MET, and/or fragments of human MET that contain pY1235, and does not cross-react with un-phosphorylated Y1235-MET, a Y1235D mutant version of MET, or any contiguous number of amino acids of MET sequence that is devoid of a phosphorylated Y1235 residue. In some embodiments, the antibody specifically binds to pY1235-MET, and/or fragments of human MET that contain pY1235, which binding is independent of the phosphorylation state of Y1230 and/or Y1234, and which antibody does not cross-react with any contiguous number of amino acids of MET sequence that is devoid of a phosphorylated Y1235 residue.

Since the CDRs of the variable regions of the rabbit monoclonal anti-pY1235 MET antibody determine antibody specificity, the CDRs of the anti-pY1235 MET antibody described herein can be grafted or engineered into an antibody or other immunological binding reagent of choice to confer specificity for pY1235-MET and pY1235-containing fragments thereof, upon that immunological binding reagent. In some embodiments, immunological binding reagents are described herein that contain 1, 2, 3, 4, 5, or all of the CDRs of such an antibody. The anti-pY1235 MET immunological binding reagents (e.g., antibodies) described herein bind strongly and to pY1235-MET expressed in target cells and tissues, e.g., cancer cells. The anti-pY1235 MET immunological binding reagents (e.g., antibodies) described herein find use in, e.g., various immunoassays for identifying, assessing, or validating inhibitors of MET activation and/or phosphorylation; selecting subjects for treatment with inhibitors of MET phosphorylation; monitoring MET activation during treatment; and the like.

2. Anti-pY1235-MET Immunological Binding Reagents (e.g., Antibodies)

In some embodiments, the invention provides anti-pY1235 MET immunological binding reagents which have one, two, or all CDRs 1, 2, and 3 of the $V_H$ chain of antibody #23111 corresponding to SEQ NO:1 or 11 and one, two, or all CDRs 1, 2, and 3 of the $V_L$, chain antibody #23111 corresponding to SEQ ID NO:2 or 12. For example, the invention provides anti-pY1235 MET immunological binding reagents that have CDRHs 1, 2, and 3 corresponding to SEQ ID NOs:3, 4, and 5 respectively. Additionally, or alternatively, the invention provides anti-pY1235 MET immunological binding reagents that have CDRLs 1, 2, and 3 corresponding to SEQ ID NOs:6, 7, and 8 respectively. In some forms, the anti-pY1235 MET immunological binding reagents are Fab. In some forms, the VH and VL chains will be linked by a peptide linker, to form a scFv, or may have one or more cysteine residues engineered into the framework region to permit formation of a disulfide bond linking the two chains together.

It is contemplated that the anti-pY1235 MET immunological binding reagents (e.g., antibodies) can be modified in various ways without losing antigen recognition capability. The consensus sequences provided herein identify residues that will tolerate substitution. Thus, the invention provides immunological binding reagents that specifically bind pY1235-MET and that have $V_H$ chains with at least 90%, 93%, 95%, 97% or 99% amino acid sequence identity to the sequence of the $V_H$ chain of antibody #23111 (e.g., SEQ ID NO:1 or 11) and/or $V_L$ chains with at least 90%, 93%, 95%, 97% or 99% amino acid sequence identity to the sequence of the $V_L$ chain of antibody #23111 (e.g., SEQ ID NO:2 or 12). In some embodiments, the invention provides immunological binding reagents that specifically bind pY1235-MET and that have $V_H$ chains with 100% sequence identity to the sequence of the $V_H$ chain of antibody #23111 (e.g., SEQ NO:1 or 11) and/or $V_L$ chains with 100% sequence identity to the sequence of the $V_L$ chain of antibody #23111 (e.g., SEQ ID NO:2 or 12). In some embodiments, the invention provides immunological binding reagents that specifically bind pY1235-MET and that have $V_H$ chains with 1, 2, 3, 4, 5, 6, 7, 8, 9, 10, 11, 12, 13, 14, or 15 substitutions in comparison to the sequence of the $V_H$ chain of the antibody #23111 (e.g., SEQ ID NO:1 or 11) and/or $V_L$ chains with 1, 2, 3, 4, 5, 6, 7, 8, 9, 10, 11, 12, 13, 14, or 15 substitutions in comparison to the sequence of the $V_L$ chain of antibody #23111 (e.g., SEQ ID NO:2 or 12).

In some embodiments, the invention provides immunological binding reagents that specifically bind pY1235-MET and that have one, two, or all heavy chain CDRs with at least 90%, 93%, 95%, 97%, 99%, or 100% amino acid sequence identity to the respective CDRs of the $V_H$ chain of antibody #23111 (SEQ ID NOs:3, 4, and 5) and/or one, two, or all light chain CDRs with at least 90%, 93%, 95%, 97%, 99%, or 100% amino acid sequence identity to the CDRs of the $V_L$ chain of antibody #23111 (SEQ ID NO:6, 7, and 8). In some embodiments, the invention provides immunological binding reagents that specifically bind pY1235-MET and that have one, two, or three heavy chain CDRs independently with 0, 1, 2, 3, 4, 5, 6, 7, 8, 9, 10, 11, 12, 13, 14, or 15 substitutions in comparison to the respective CDRs of the $V_H$ chain of antibody #23111 (SEQ ID NOs:3, 4, and 5) and/or one, two, or three light chain CDRs independently with 0, 1, 2, 3, 4, 5, 6, 7, 8, 9, 10, 11, 12, 13, 14, or 15 substitutions in comparison to the respective CDRs of the $V_L$ chain of antibody #23111 (SEQ ID NOs:6, 7, and 8).

Preferably, the immunological binding reagents have a binding constant ($K_d$) to the target antigen (e.g., pY1235-MET) that is about 100 nM or less, for example in the range of about 1-100 nM, for example, about 100 nM, 75 nM, 50 nM, 25 nM, 10 nM, 5 nM, 3 nM, 2 nM, 1 nM, or less. Affinity can be measured using any method known in the art. Applicable assays are described herein, e.g., BIAcore analysis. Another applicable assay is provided in U.S. Patent Publication 2009/0047211. Whether or not a modified immunological binding reagent retains this utility can be readily determined by, for example, conducting one of these tests with the modified immunological binding reagents and comparing the results to the results of a like test conducted using antibody #23111.

3. Polynucleotides, Vectors and Host Cells for Producing Anti-pY1235-MET Immunological Binding Reagents The invention provides polynucleotides (DNA or RNA) which encode polypeptides comprising segments or domains of the anti-pY1235-MET immunological binding reagents (e.g., antibodies) described above. In some embodiments, the polynucleotides are substantially purified or isolated. Some of the polynucleotides of the invention comprise a polynucleotide sequence encoding a heavy chain variable region such as the heavy chain variable region encoded in SEQ ID NO:9, and a polynucleotide sequence encoding a light chain variable region such as the light chain variable region encoded in SEQ ID NO:10. Some other polynucleotides of the invention comprise nucleotide sequences that are substantially identical (e.g., at least 50%, 60%, 70%, 80%, 80%, 95%, 96%, 97%, 98% or 99%) to one of the nucleotide sequences shown in SEQ ID NOs:9 and 10. When expressed from appropriate expression vectors, polypeptides encoded by these polynucleotides are capable of exhibiting antigen binding capacity.

Also provided in the invention are polynucleotides which encode at least one CDR region and usually all three CDR regions from the heavy or light chain of antibody #23111. Some other polynucleotides encode all or substantially all of the variable region sequence of the heavy chain and/or the light chain of the antibody #23111. For example, some of these polynucleotides encode the amino acid sequence having at least about 50%, 60%, 70%, 80%, 90%, 93%, 95%, 96%, 97%, 98%, 99% or 100% sequence identity to the heavy chain variable region encoded in SEQ ID NO:9 and/or the amino acid sequence having at least about 50%, 60%, 70%, 80%, 90%, 93%, 95%, 96%, 97%, 98%, 99% or 100% sequence identity to the light chain variable region encoded in SEQ ID NO:10. Because of the degeneracy of the code, a variety of nucleic acid sequences will encode each of the immunoglobulin amino acid sequences.

Also provided in the invention are expression vectors and host cells for producing the anti-pY1235-MET immunological binding reagents (e.g., antibodies) described above. Various expression vectors can be employed to express the polynucleotides encoding the anti-pY1235-MET immunological binding reagents (e.g., antibodies) described above. Both viral-based and nonviral expression vectors can be used to produce the immunological binding reagents in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the immunological binding reagent encoding polynucleotides and polypeptides in mammalian (e.g., human) cells include pThioHis A, B & C, pcDNA3.1/His, pEBVHis A, B & C (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

Although the present invention has been described in some detail by way of illustration and example for purposes of clarity of understanding, it will be obvious that certain changes and modifications may be practiced within the scope of the appended claims. All references described herein, including Genbank accession numbers are incorporated by reference in the entirety for any and all purposes.

EXAMPLES

The following examples are offered to illustrate, but not to limit the claimed invention.

Example 1

Materials and Methods

Reagents. Purchased antibodies were qualified for use, including antigen affinity purified goat polyclonal anti-human MET extracellular domain (catalog number AF276, R&D Systems); mouse monoclonal anti-full-length MET (clone Met4, Van Andel Research Institute); mouse monoclonal anti-C-terminal MET (clone L41G3, Cell Signaling Technologies, Inc.) and rabbit monoclonal anti-pY1234/pY1235-MET (clone D26, Cell Signaling Technologies, Inc.). Two rabbit monoclonal antibodies (mAbs) specific to pY1235-MET (clone 23111) and pY1356-MET (clone 7334) were developed under contract with Epitomics Inc. using phosphorylated peptide antigens corresponding to amino acid sequences surrounding these tyrosine residues (Supplemental Materials). Recombinant MET (rMET) calibrator protein was produced in HEK293 cells (Supplemental Materials). Antibodies were biotinylated using Sulfo-NHS-LC-biotin (Thermo-Fisher Scientific). Details of commercially available key assay reagents are described in SOP341203 and SOP341206, available at detd.caneer.gov/ResearchResources/ResearchResources-biomarkers.htm.

Animal models and drug administration. Athymic nude mice (nu/nu NCr; Animal Production Program, NCI-Frederick) were implanted with the human cancer cell lines U87 (glioblastoma); A549 (lung carcinoma); MDA-MB-231 (breast carcinoma); HT-29 (colon carcinoma); or with GTL-16, MKN45, or SNU5 (all gastric carcinomas, MET-amplified) as described (17). All cell lines were obtained from the Division of Cancer Treatment and Diagnosis Repository, NCI-Frederick and authenticated using AmpFLSTR Identifiler (Applied Biosystems).

MET inhibitors PHA665752 (NSC 748798-T), PF02341.066 (NSC 749769-Y, crizotinib), and tivantinib (NSC 758242); VEGFR inhibitor pazopanib (NSC 737754); and multikinase inhibitor sorafenib (NSC 747971, lot #747971-U/3) were provided by the Developmental Therapeutics Program, National Cancer Institute (NCI). Purity was established by proton-carbon NMR, HPLC, and mass spectrometry. Sorafenib was dissolved in DMSO for in vitro studies. PF02341066 and pazopanib were administered by oral gavage in a saline vehicle and PHA665752 by intraperitoneal (IP) injections in a vehicle composed of 10% DMSO in saline. Tivantinib was administered orally in a PEG 400:20% vitamin E tocopheryl polyethylene glycol succinate solution (60:40) vehicle.

The NCI Animal Production Program, NCI-Frederick, is accredited by the Association for Assessment and Accreditation of Laboratory Animal Care International and follows Public Health Service policy on the humane care and use of laboratory animals. All studies were conducted according to approved NIH Animal Care and Use Committee protocols.

Xenograft biopsy and tumor quarter collection and extract preparation. Specimen collection and handling conditions were adaptations of those achievable in past NCI clinical trials (18, 19). Briefly, 18-gauge Temno Trucut needle biopsies were immediately flash frozen in O-ring-sealed, conical-bottomed, screw-cap, 1.5-mL Sarstedt cryovials. Tubes were sealed, returned to liquid nitrogen, and stored at −80° C. until use. Whole xenograft tumors were collected on the same schedule as tumor biopsies by standard dissection methods and cut into 2 to 4 equal pieces with fine-point scissors before flash-freezing. All preclinical samples were frozen within 2 min of excision.

Tissue samples were processed by adding ice-cold Cell Extraction Buffer (Invitrogen) and supplemented with PhosSTOP (Roche) and protease inhibitor tablets (Roche) to the frozen tissue (0.35 mL buffer/biopsy and 0.75 mL buffer/tumor quarter). Tissue was immediately homogenized with a PRO200 homogenizer with a Multi-Gen adaptor (Pro Scientific) and a 5 mm generator at the maximum setting for 10 sec at 2° C. to 8° C. The extract was vortexed and homogenization was repeated. Extracts were incubated at 2° C. to 8° C. for 60 min with orbital shaking, and clarified by centrifugation at 12,000×g for 5 min at 2° C. to 8° C. Cleared supernatant was aspirated and aliquoted. Total protein was measured by Bradford protein assay procedure (Bio-Rad).

Determination of mouse content of human tumor xenografts. Mice were inoculated bilaterally with human tumor line cells (1×10$^7$) and tumor growth monitored daily. One cohort of mice was grouped when tumors reached 100, 200, 400, 500, 800, 1000, 1500, or 2000 mg; the mean tumor size for each weight-bin was determined, and the tumors removed for analysis. A second cohort was euthanized 10, 14, 18, 22, 26, and 30 days post-implantation, irrespective of tumor size, and retrospectively grouped into 100, 200, 400, and 600 mg weight-bins. DNA from one tumor quarter from each animal was analyzed for mouse and human DNA content (20).

Xenograft ischemia study. SNU5 tumor xenografts were staged to ~2.00 mg (n=5/group). Needle biopsies were collected under anesthesia and immediately flash-frozen as controls. Tumors were excised and quarters transferred to sterile normal saline maintained at 25° C.±3° C. (cold ischemia) or 37° C. (warm ischemia) for 1, 2, 3, 4, 5, 8, 10, 15, 30, or 60 min in temperature-controlled saline before being flash frozen. All flash-frozen samples were stored at −80° C., and lysates were processed within 2 wk of collection.

Fit-for-purpose MET inhibitor studies. Fit-for-purpose studies result in validated PD assays and provide drug mechanism of action information. To demonstrate assay fit-for-purpose in preclinical models, mice bearing GTL-16 and SNU5 xenografts were randomized when tumors reached 200±25 mm$^3$ in size and dosed daily for 8-10 days with vehicle, oral PF02341066 (6.25, 12.5 or 25 mg/kg), or IP PHA665752 (25 or 50 mg/kg). In a separate study, mice with SNU5 xenografts were staged to 200 mm$^3$ and treated for 8 days with vehicle (daily), pazopanib (100 mg/kg daily), tivantinib (200 mg/kg daily), or combinations of pazopanib (daily) with 2 dose levels of tivantinib (200 mg/kg daily or 200 mg/kg twice daily). Extracts of core needle biopsies collected 4 h after tivantinib administration on Day 8 were analyzed for MET, pMET, and hypoxia inducible factor 1, alpha subunit (HIF-1α) (21).

Core needle biopsies of HPRC tumor. Multiple 18-gauge needle biopsies were collected from a surgically-resected tumor from a patient with HPRC (Urologic Oncology Branch, NCI) within 2 min of resection and immediately flash frozen. The patient gave written informed consent for study inclusion and was enrolled in an NCI Institutional Review Board-approved protocol. Study design and conduct complied with all applicable regulations, guidances, and local policies.

MET immunoassay procedure. The full-length MET immunoassay measures the total levels of full-length MET in tumor tissue samples, irrespective of phosphorylation status. An affinity-purified goat polyclonal antibody against human MET extracellular domain (catalog number AF276) was used to coat 8-well NUNC Maxisorp strips overnight at 2° C. to 8° C. with 1 µg/mL buffer (0.1 M sodium carbonate/bicarbonate buffer pH 9.6, 100 µL/well). Wells were blocked for 2 h with 1×PBS, 0.5% mannitol, 0.2% glycine, and 0.2% BSA, and strips were assembled on 96-well plate frames, freeze-dried, and sealed in desiccated pouches (6-month stability). For the immunoassay, 100 µL each of purified rMET calibrator, controls, and tumor lysates (at protein concentrations of 10-50 µg/mL) prepared in assay buffer (1×PBS/Casein [BioFx] containing PhosSTOP, protease inhibitors and 0.1% Triton X-100 [Roche]) were added to the AF276-coated wells. The rMET assay calibrator was prepared for the dynamic range of the assay. Plates were incubated at ambient temperature (25° C.±3° C.) on an orbital shaker (600 rpm) 1 h to capture MET. After three washes with assay buffer, 100 µL/well 200 ng/mL biotin-conjugated mouse monoclonal MET antibody (clone L41G3) was added to the plates and incubated 1 h at 25° C.±3° C., followed by a second wash and the addition of 100 µL/well 200 ng/mL streptavidin poly-HRP conjugate (Pierce). After 30-min incubation with the HRP-conjugate, plates were washed 4 times and 100 µL SuperSignal ELISA Pico Chemiluminescent Substrate (pierce) was added to each well. Plates were read within 10 min using an Infinite 200 Microplate ELISA reader (Tecan, USA). MET immunoassay calibration curves were analyzed on GraphPad Prism and unknown values were calculated using 4-parameter curve fitting.

Three different pMET immunoassays were developed for the PD studies: pY1234/1235-, pY1235-, and pY1356-MET (Supplemental Material). The pMET immunoassay procedures were similar to the full-length MET immunoassay except that rabbit mAbs specific to pY1234/1235-MET (clone D26, Cell Signaling Technologies), pY1235-MET (clone 23111), or pY1356-MET (clone 7334) were conjugated to biotin and used as reporter antibodies for the immunoassay. The pMET assay calibrators were prepared for the dynamic range of each assay. Assay control samples were prepared by combining GTL-16, SNU5, A549, MKN45, or U87 xenograft tumor lysates to achieve low, medium, and high MET concentrations at 10 to 50 µg/mL total protein concentrations.

MET immunofluorescence analysis. HT-29, GTL-16 and A549 cancer cell lines were treated with DMSO vehicle (0.1% w/v), 100 nM PF02341066, or 100 nM sorafenib for 24 h at 37° C. Cells were fixed in 10% neutral-buffered formalin (Sigma-Aldrich) for 24 h, pelleted, and then embedded in paraffin. After 5-µm sectioning, antigen retrieval with Bond Epitope Retrieval Solution 2 (at 100° C. for 10 min) and immunofluorescent staining were performed on the Bond-max Autostainer (Leica Biosystems). For antigen detection, 10 µ/mL primary antibody (anti-pY1235-MET, clone 23111) was followed by 10 µg/mL goat anti-rabbit AF488 (Life Technologies). Immunofluorescence microscopy was performed on core needle biopsies of a resected a human HPRC tumor stained with 5 µg/mL anti-full-length MET (clone Met4) followed by 10 µg/mL anti-mouse AF660 (Life Technologies). Image acquisition and analysis were performed on a wide-field fluorescent, confocal microscope (Nikon 90i, Andor Camera, NIS Elements Software).

Statistical analyses. Regression analysis and descriptive statistics including means, standard deviations, coefficients of variation (CV), 1-way ANOVA analyses, and Student's t-tests were conducted with Microsoft Excel and GraphPad Prism (v3.04). The 95% confidence interval was significant at α=0.05 for a two-sided t-test.

Results:
Design and Development of Sandwich Immunoassays for Measuring Key phosphoMET Species.

Figure 7B:
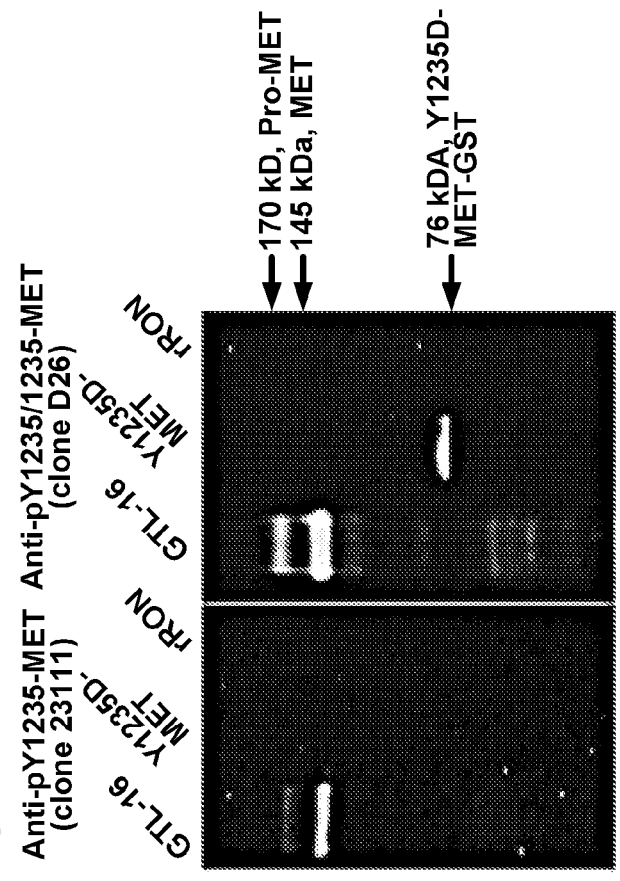
FIG. 7: Specificity of the MET antibodies demonstrated by Western blot analysis. (A) Specificity of pY1235-MET antibody clone 23111 demonstrated by Western blotting lysates from GTL-16 cells treated with increasing amounts of the MET inhibitor PF02341066 (top panel). Similar blots following preincubation of antibody with pY1235-MET peptide ($2^{nd}$ panel), pY1234-MET peptide ($3^{rd}$ panel), and recombinant cytoplasmic RON ($4^{th}$ panel). The bottom panel shows Western blots with C-terminal antibody to demonstrate the presence of full-length MET. (B) Western blots of GTL-16 human gastric tumor cell extract, Y1235D-MET peptide, and recombinant RON probed with anti-pY1235-MET (clone 23111) and anti-pY1234/1235-MET (clone D26). (C) Western blots of extracts of GTL-16 cells treated with increasing amounts of PF02341066 probed with antibody to pY1356-MET (clone 7334) in the absence (top panel) or presence (second panel) of synthetic pY1356 peptide, or the presence of nonphosphorylated Y1356 peptide (third panel). The bottom panel shows total full-length MET staining with C-terminal antibody. (D) Western blot of recombinant full-length MET calibrator probed with antibodies to pY1235-MET (clone 23111), pY1234/12355-MET (clone D26), pY1356-MET (clone 7334), and MET C-terminal antibody (clone L41G3). MW, molecular weight standards.
Figure 7A:
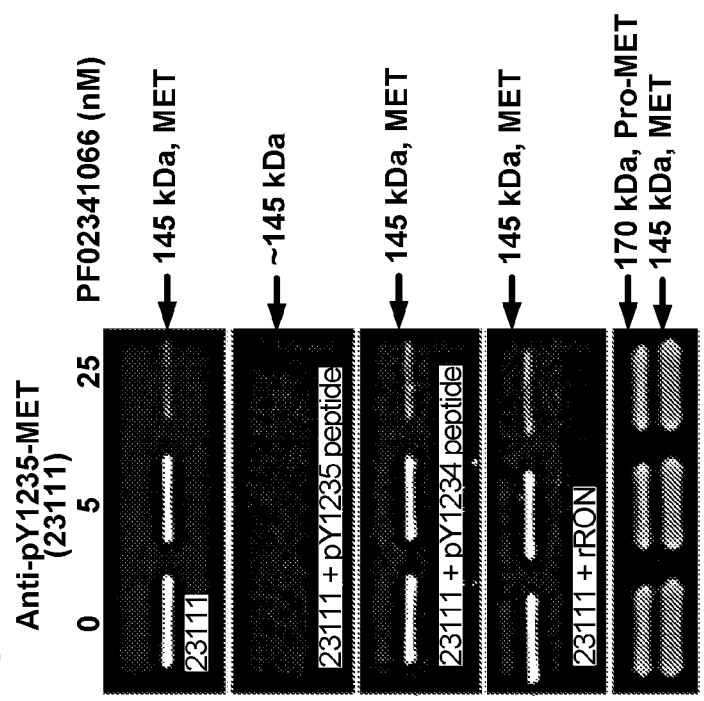
Figure 7D:
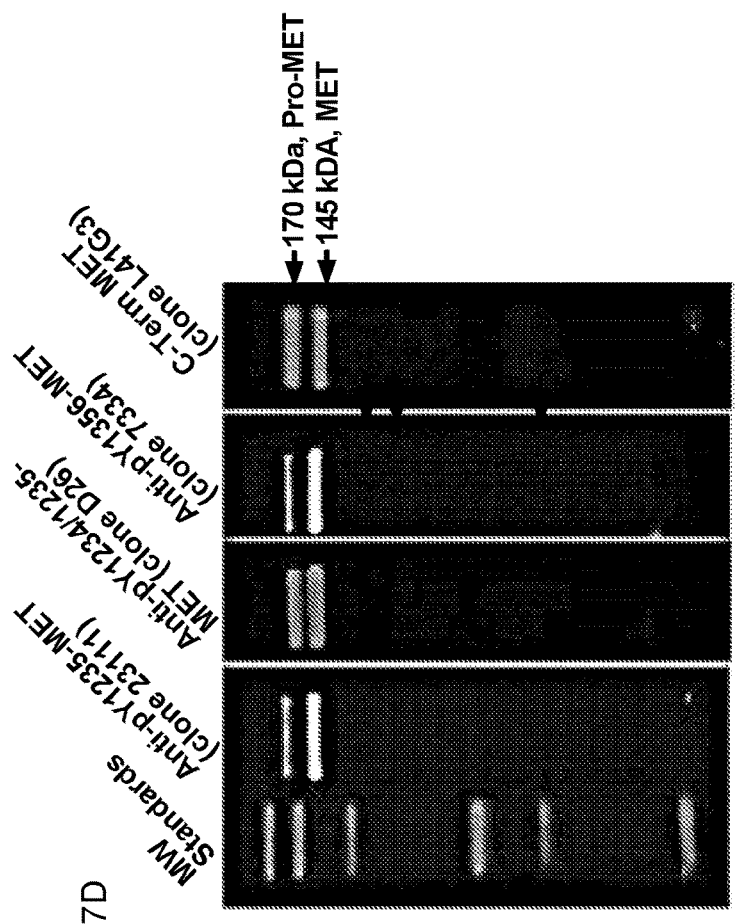
Figure 7C:
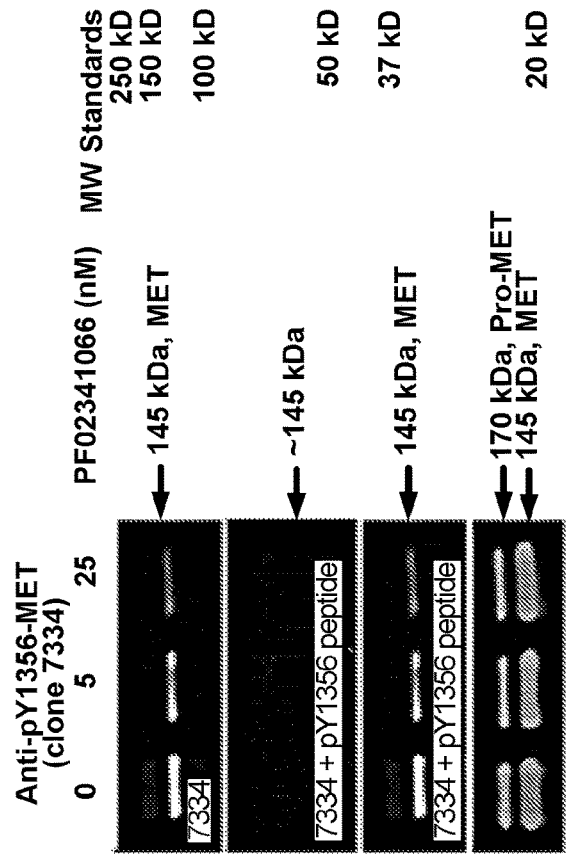

Tyrosines 1234, 1235, and 1356 mediate MET signal transduction via phosphorylation; so many MET-targeted agents are designed to reduce MET phosphorylation at one or more of these sites. To study the pharmacodynamics (PD) of such drugs, a sandwich immunoassay was designed to capture MET via its extracellular domain and then probe the captured MET for a particular phospho-epitope (pY1234/1235, pY1235 or pY1356) using specific monoclonal antibodies (FIG. 1A). The capture antibody essentially did not cross-react with recombinant extracellular domains of the two most likely cross-reactive human tyrosine kinases, RON (macrophage stimulating 1 receptor; MST1R) and EGFR. At 10-fold excess concentration (4 400 pM) over rMET (0.4 40 pM), cross-reactivity with RON was <5% and EGFR cross-reactivity was not detectable (data not shown). The pY1235-MET species was measured using a new rabbit mAb (#23111) that recognizes the pY1235 epitope independent of Y1234 phosphorylation status, and its high specificity was demonstrated by Western blot analysis using synthetic peptides, rMET, cell lysates, and mouse tissues (FIGS. 7A and 7D). Unlike the specificity of D26 antibody for the dual phosphorylated pY1234/pY1235 epitope, the mAb produced by clone 23111 showed no cross-reactivity with the cytoplasmic domain of RON or with this MET epitope when phosphorylated only at Y1234 or when tyrosine 1235 was replaced by aspartic acid (FIGS. 7A and 7B). It stained the plasma membrane of MET-expressing cell lines in an HGF-dependent manner that was sensitive to MET inhibitors, but not sorafenib (FIG. 1B). A new rabbit mAb recognizing the pY1356 epitope of MET (clone 7334) was also generated for use in the immunoassay (FIGS. 7C, 7D).

Analytical Validation of the Sandwich Immunoassays

Using full-length, purified rMET as calibrator, the dynamic ranges of the calibration curves for each assay were established: 0.3-40 pM for full-length and pY1234/1235-MET assays and 3.125-200 pM for the pY1235- and pY1356-MET assays (FIG. 1C). Assay sensitivities were 1.5, 1.5, 7.8, and 15.6 fmol/μg protein, respectively, and the assays did not significantly cross-react with mouse MET species (Supplemental Materials).

The MET immunoassays were subjected to a rigorous validation protocol for analytical performance using clinically relevant tumor sampling procedures (core needle biopsy of tumors in mice) and specimen preparation procedures (Supplemental Materials). Dilution linearity studies showed that tumor extracts could be diluted up to 8-fold without affecting assay performance (Table 1). Spike-recovery experiments of rMET in xenograft extracts established immunoassay accuracy. Recovery ranged from 78%-116% for full-length MET, pY1234/1235-MET, and pY1235-MET assays, and 86%±29% for pY1356-MET (mean±SD; Table 1). Intra-plate (n=20) and inter-day (n=5) variation were evaluated using three xenograft tumor extracts assayed at minimum of five different days by two operators; intra-assay CV was <10% and interassay CV was <14% (Table 1). After reducing the procedures and operating parameters of the validated assay to SOPs, assay robustness was formally demonstrated by SOP-driven assay transfer from the development to the clinical testing laboratory as previously described (18, 22).

The validated assay was capable of quantifying full-length MET in extracts of GTL-16, A549, MDA-MB-231, and U87 xenograft tumors over a wide range of protein loads per well (FIG. 1D). Full-length MET was detected over a range of 0.05-1.79 fmol/μg protein, and as expected the MET-amplified model (GTL-16) contained the highest levels (1.31-1.79 fmol/μg protein). A least significant change (LSC) calculation, which combines both technical variation of the assay and biological variation of the biomarker (determined by analyzing multiple quadrants of xenografted SNU5 tumors), established a 45% change as the minimal effect level required to demonstrate a drug effect (Supplemental Materials).

Biopsy Handling to Control Preanalytical Variables

Figure 2B:
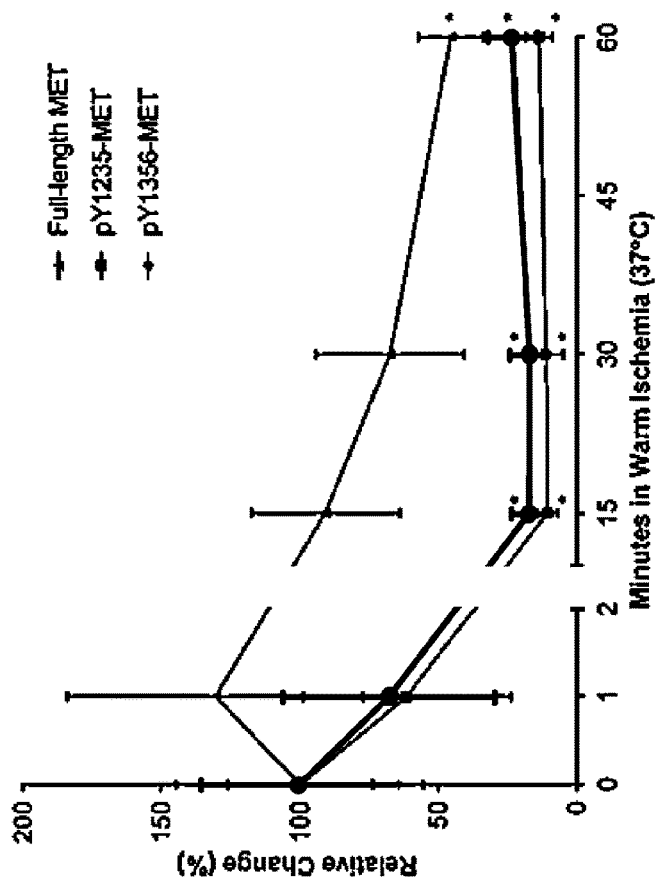

Preanalytical variables (specimen handling, shipping, and storage procedures) can have a significant impact on the reliability of biomarker measurements in the laboratory, and phosphoproteins involved in dynamic responses of signaling pathways are notoriously labile during specimen collection due to ischemia and other factors (23-25). The stability of full-length MET and its phosphospecies was characterized in biopsies of SNU5 xenografts subjected to increasing ischemia time, which was defined as the total time needed for core needle biopsy sampling, specimen handling, and flash freezing. MET levels in core needle biopsy samples frozen immediately after collection from anesthetized animals (defined as the zero time point) were set as baseline (100%). Both pY1235- and pY1356-MET levels decreased by >60% during 15 min of cold ischemia (25° C.±3° C.), and continued decreasing over the next 15 min (P<0.05; FIG. 2A). During 15 min of warm ischemia (37° C.), both pY1235- and pY1356-MET levels decreased by >80% (P<0.05; FIG. 2B). The pY1234/p1235-MET species exhibited similar degradation under these conditions (data not shown). In contrast, full-length MET levels were relatively stable for up to 60 min of cold ischemia, but decreased significantly at 37° C. (FIGS. 2A, 2B).

Figure 2D:
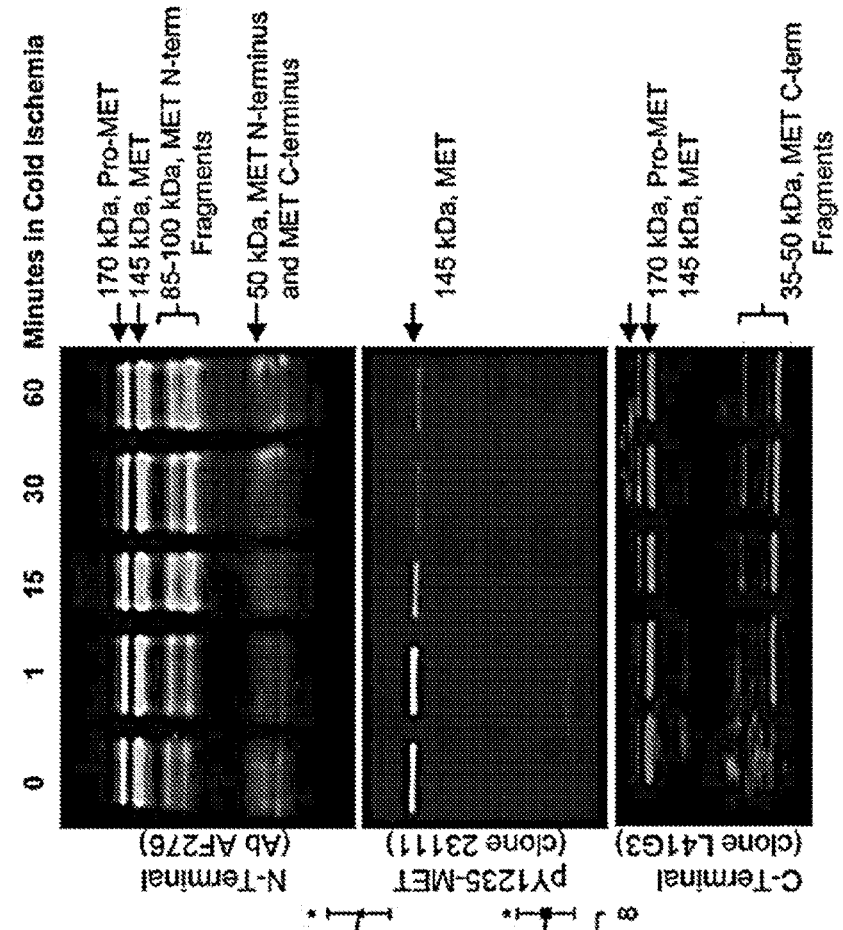
Figure 2C:
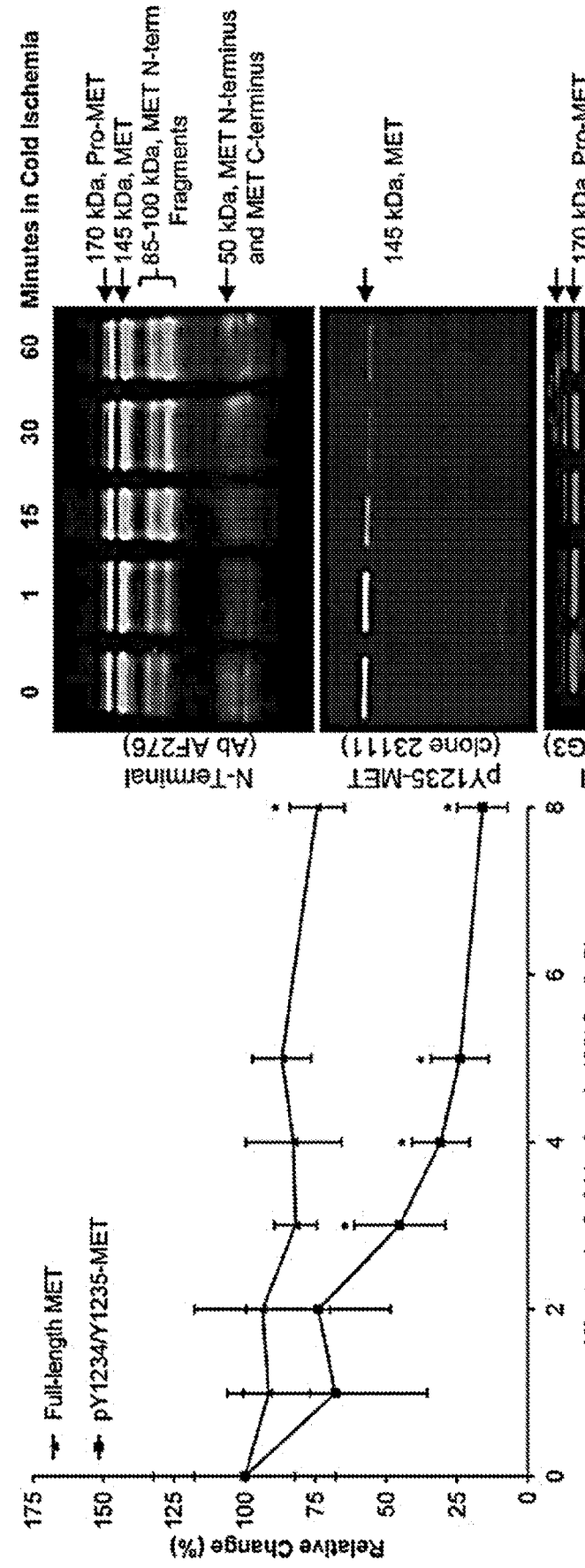

A follow-up study evaluated the stabilities of pMET and full-length MET during 8 min of cold ischemia. After just 3 min of cold ischemia, pY1234/1235-MET levels decreased by >50% (P<0.05; FIG. 2C). Based on Western blot results, loss of full-length pY1235-MET signal during cold ischemia was predominantly due to loss of the pY1235-MET epitope, plus a small amount of degradation of full-length MET (the appearance of N- and C-terminal fragments, FIG. 2D). Stabilities of the pY1234/1235-MET and pY1356-MET analytes were similar (data not shown). Core needle biopsies frozen within 2 min of collection will yield valid pMET assay results. In some cases, a longer duration between collection and freezing can yield valid pMET assay results.

Pharmacodynamics of MET RTK Inhibitors in Gastric Carcinoma Xenograft Models

Figure 9A:
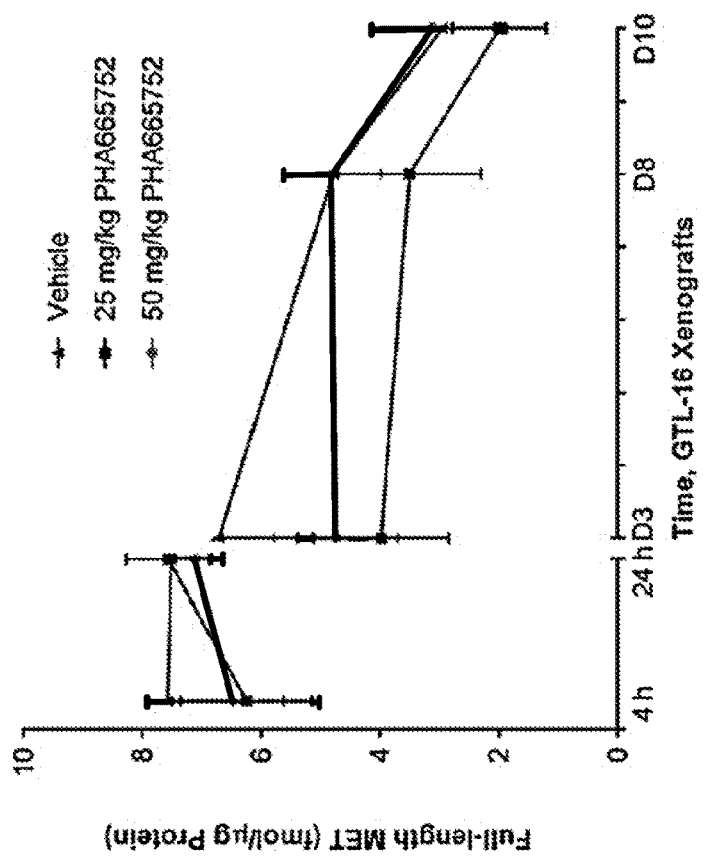
FIG. 9: Inhibition of tumor growth and intratumoral MET phosphorylation by PHA665752 in the GTL-16 human gastric cancer model. (A) Intratumoral inhibition of pY1356-MET levels in GTL-16 xenografts during 10 days of PHA665752 treatment; n=5-6 per dose per time point. All graphs plot mean±SD. The dotted line indicates a 45% decrease in the pY1356-MET to full-length MET ratio from the vehicle-treated group; changes greater than this can be attributed to drug effect. (B) Full-length MET plotted over time following daily doses of 25 and 50 mg/kg PHA665752 or vehicle; data normalized to extracted protein concentration. Tumor samples were analyzed at 4 and 24 hours after dose 1, and 4 hours after dose 3 (D3), 8 (D8), and 10 (D10).
Figure 9B:
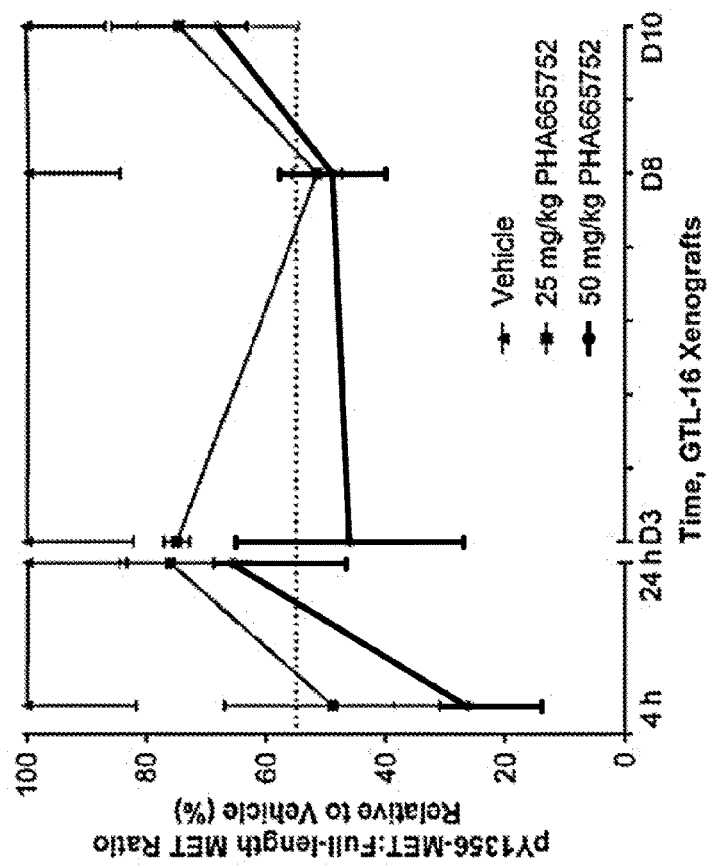

Mice with GTL-16 tumor xenografts, a MET-amplified model, were treated daily with the MET inhibitors, PHA665752 or PF02341066, and sampled at clinically relevant time points (4 or 24 h) after drug administration. The 25 and 50 mg/kg/day dose levels of PHA665752 slowed the growth of GTL-16 xenograft tumors and achieved tumor stasis after 8-10 days of treatment (FIG. 3A, Study Days 17-19). Four h after the first dose there was a dose-dependent reduction in the pY1235-MET:MET ratio of 62% and 80%, respectively (FIG. 3B), effect sizes that exceeded the LSC threshold of 45%. Over the next 20 h, the pY1235-MET:MET ratio partially to fully recovered, depending upon dosage. Additional daily doses of 50 mg/kg PHA665752 significantly decreased the pY1235-MET:MET ratio, while the 25 mg/kg dose produced inconsistent changes (FIG. 3B). The ratio of pY1356-MET:MET also declined after the first dose, although it recovered to normal levels within 20 h (FIG. 9A). Therefore, the tumor stasis observed with this agent and dosage regimen was associated with intervals of modest reductions in the pY1235 and pY1356 targets followed by target recovery. The absolute level of full-length MET also decreased by 40%-50% within 10 days of treatment with either vehicle or drug (FIG. 9B).

Figure 10B:
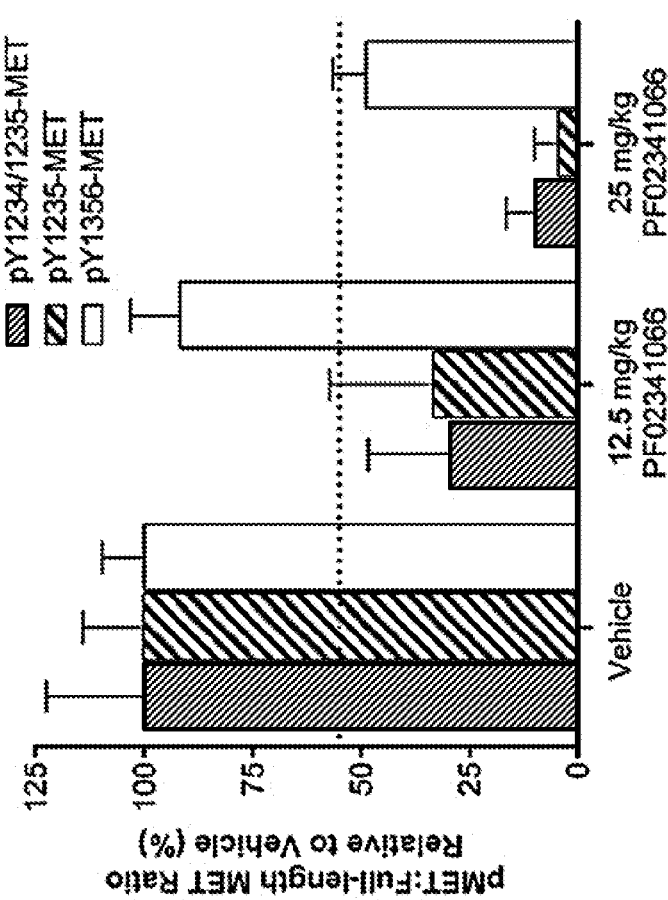
FIG. 10: Comparison of pMET:full-length MET ratios in vehicle- and PF02341066-treated SNU5 xenografts. Full-length MET and pMET were measured at 4 hours after treatment with 12.5 or 25 mg/kg of PF02341066 or vehicle. (A) Levels of pY1234/1235-, pY1235-, and pY1356-MET expressed as ratio of full-length MET, (B) pY1234/1235-, pY1235-, and pY1356-MET to full-length MET ratios normalized to vehicle. All graphs represent mean±SD; n=5/group, except pY1235-MET 25 mg/kg group where n=2. The dotted line indicates a 45% decrease in the ratio of pMET to full-length MET from the vehicle-treated group; changes greater than this can be attributed to drug effect.
Figure 10A:
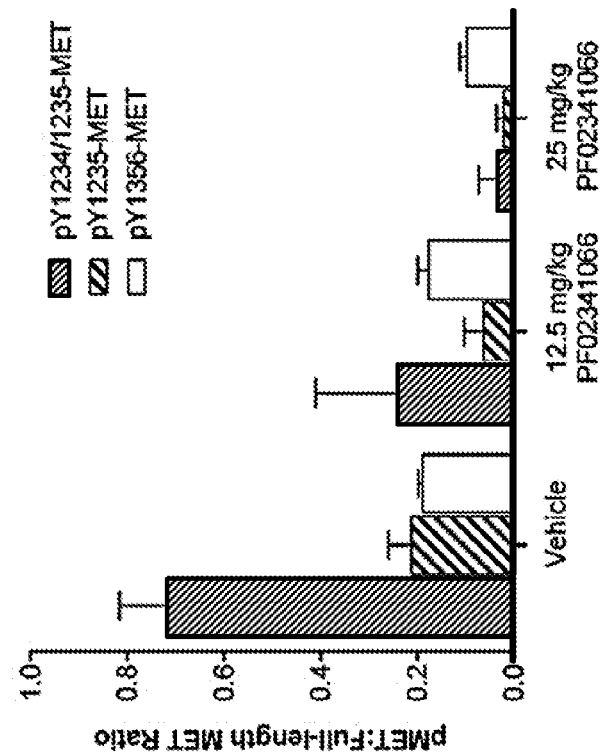

As previously reported (10), treatment of GTL-16 xenografts with daily oral PF02341066 at the 25 mg/kg dose level achieved stasis of GTL-16 xenografts by the seventh day of treatment (FIG. 3C; Study Day 11). Only this dose level reduced the pY1235-MET:MET ratio (by 65%) 4 h after treatment, and this ratio recovered completely during the next 20 h (FIG. 3D). Additional daily doses of PF02341066 further reduced the pY1235-MET:MET ratio, so molecular target control 4 h after each dose was achievable throughout the daily treatment period. The SNU5 model exhibited a similar dose-dependent PD response to PF02341066, and again pointed to greater PD responsiveness of pY1235 than pY1356 following TKI therapy (FIG. 10).

Figure 4A:
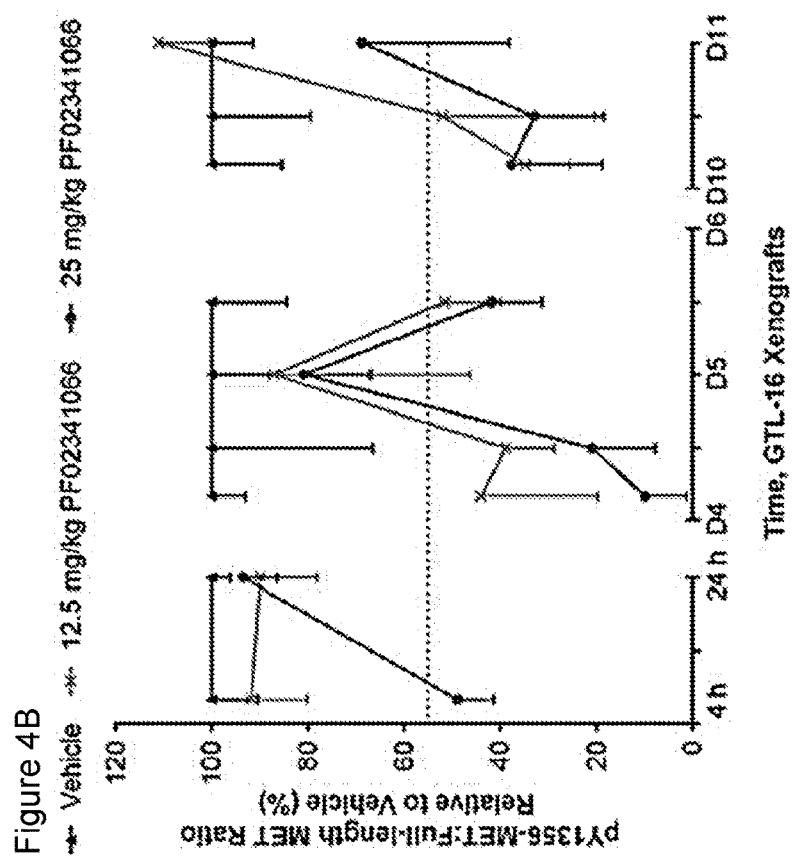
FIG. 4. Reduction of GTL-16 tumor growth and MET phosphorylation by PF02341066. (A) pY1235-MET:MET ratio and (B) pY1356-MET:MET ratio during daily treatment with PF02341066. Tumor samples were analyzed at 4 and 24 h after dose 1, then 4, 12 and 24 h after dose 4 (D4), 12 h after dose 5 (D5), and 4, 12, and 24 h after dose 10 (D10). Mean±SD, all groups n=2-6 per dose per time point. The dotted line indicates the LSC in pMET:MET ratio from the vehicle-treated group of 45%; changes larger than this are attributed to drug effect. (C) Absolute levels of full-length MET plotted over time following daily doses of 12.5 and 25 mg/kg PF02341066 or vehicle; data normalized to extracted protein.
Figure 4B:
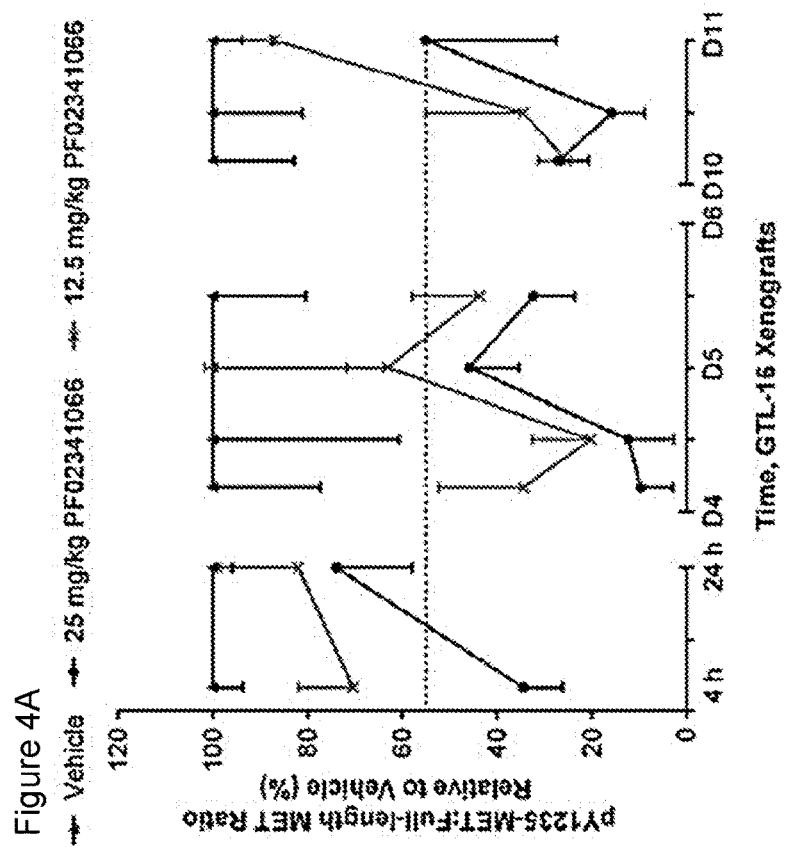

A second study of GTL-16 xenografts treated daily with PF02341066, but with denser tumor sampling to more fully characterize the PD response, confirmed that only the 25 mg/kg/day dose level achieved a molecular target response after the first dose. However, there was a cumulative, dose-dependent PD effect on the pY1235-MET:MET ratio such that by Day 4, both the 25 and 12.5 mg/kg dose levels produced PD responses 4 h and 12 h after drug administration, although only the higher dose maintained this PD response for the entire 24-hour dosing interval (FIG. 4A). The pY1356-MET:MET ratio decreased after 4 and 12 h but fully recovered by 24 h at both dose levels (FIG. 4B). Again, full-length MET levels decreased by 40%-50% by treatment day 10 in both drug- and vehicle-treated groups (FIG. 4C).

This preclinical modeling suggest that greater control of MET signaling than the intermittent 80% reduction in the pMET:MET ratio observed here can improve regressions of MET-amplified tumor models. These data also indicate the utility of using the more consistent pMET:MET ratio instead of absolute levels of particular pMET species as PD endpoints, at least in preclinical models where mouse cell infiltration of human tumor xenografts over time diluted the absolute level of human MET per microgram extracted protein (FIG. 11).

Fit-for-Purpose Modeling of the First-in-Human Application of the Assay

Figure 5B:
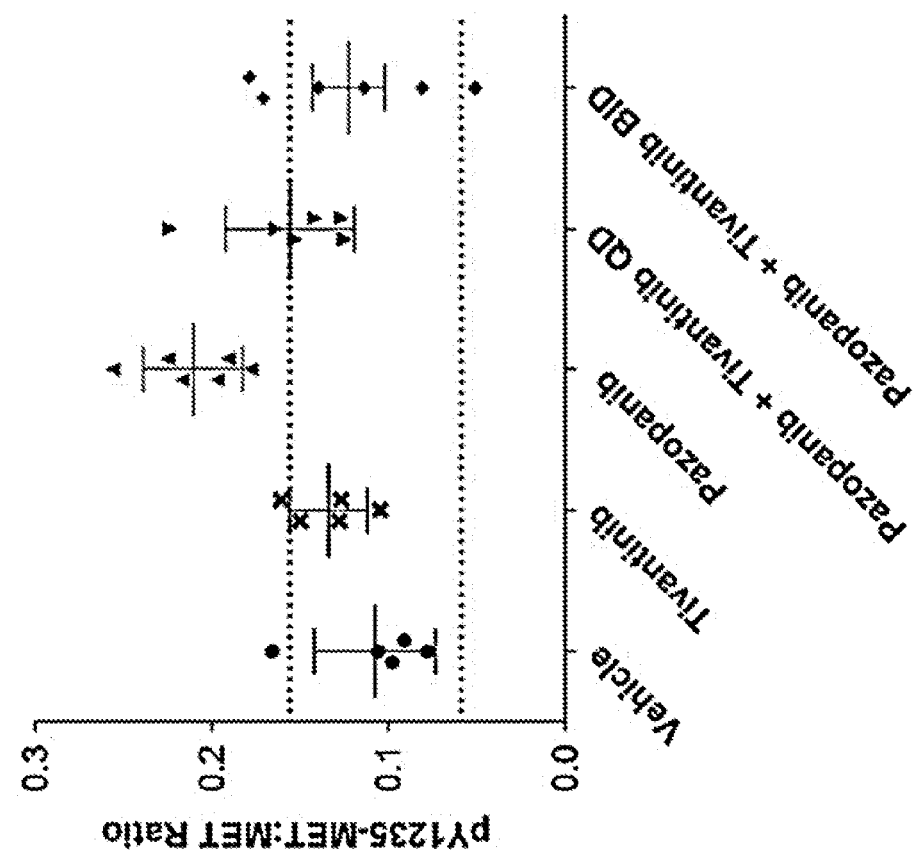
FIG. 5. Treatment of SNU5 gastric cancer xenografts with the VEGFR inhibitor pazopanib activates MET. Full-length MET, pMET:MET ratios, and HIF-1α levels were measured on day 8 of treatment with vehicle, tivantinib or pazopanib alone, or the combination of pazopanib+tivantinib (QD or BID) in combination. (A) Absolute levels of full-length MET, (B) pY1235-MET:MET ratio, and (C) pY1356-MET:MET ratio. The dotted line indicates the LSC in pMET:MET ratio from the vehicle-treated group of 45%; changes larger than this are attributed to drug effect. (D) HIF-1α levels were measured in extracts generated from xenograft tumor quadrants. All graphs plotted mean±SD, all groups n=5-6 per dose per time point. Single asterisk (*)p<0.05 compared to vehicle group.
Figure 5A:
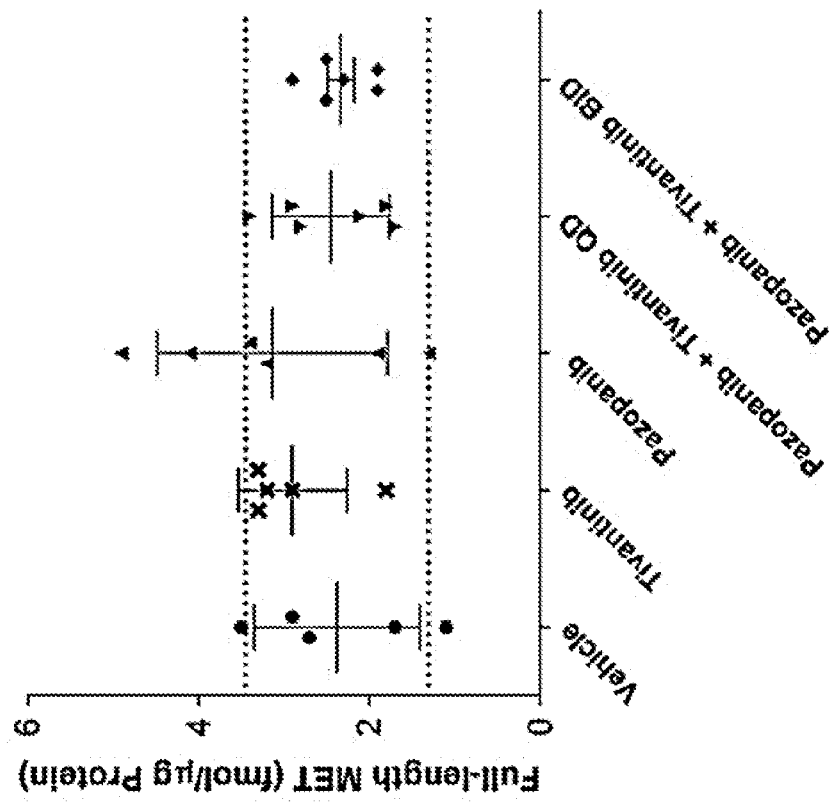
Figure 5C:
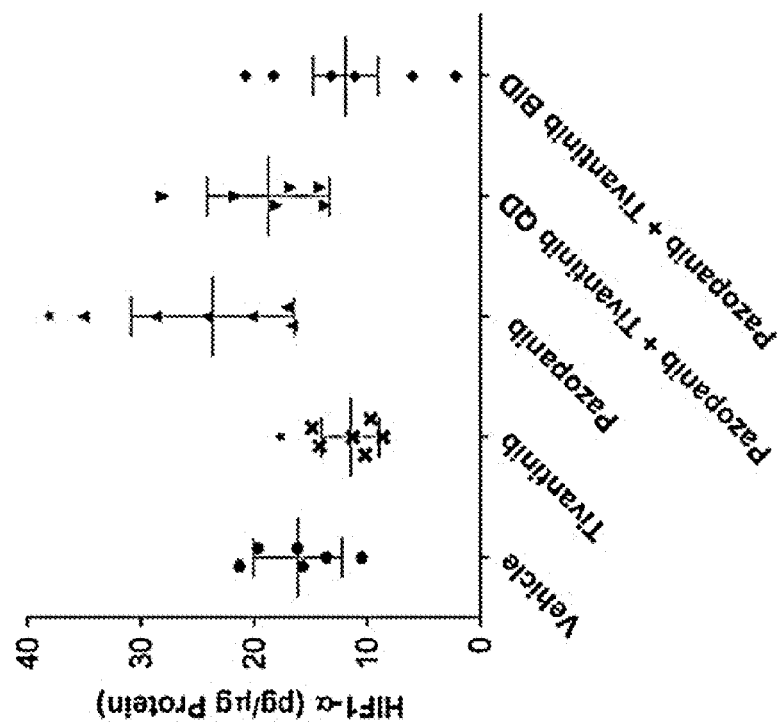
Figure 5D:
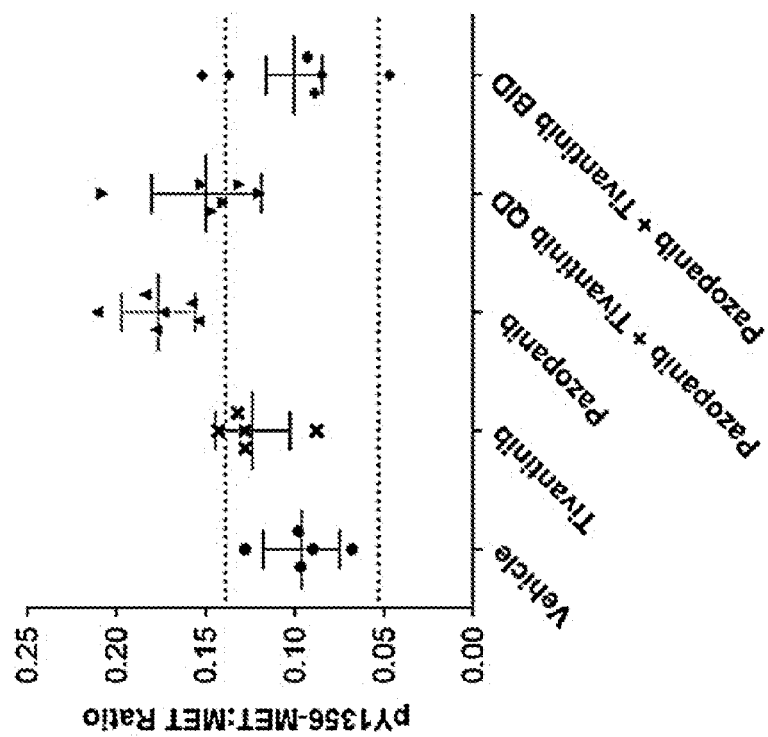

The first clinical application of the validated assay is assessment of tumor PD response during a phase 1 clinical trial of the VEGFR/PDGFR inhibitor pazopanib alone and in combination with the MET inhibitor tivantinib (ClinicalTrials.gov NCT01468922). The trial is testing two hypotheses: (i) MET will be upregulated as part of a compensatory response to VEGFR/PDGFR inhibition by pazopanib, and (ii) tivantinib will blunt that upregulation by inducing degradation of total MET (26). To model this trial, mice bearing SNU5 xenografts were treated with vehicle or the drugs individually or in combination and the tumors were sampled on day 8 using 18-gauge biopsy needles to replicate the sampling planned for the clinical trial. Neither single-agent pazopanib nor tivantinib affected full-length MET levels (FIG. 5A). However, treatment with pazopanib, but not tivantinib, increased both pY1235-MET:MET and pY1356-MET:MET ratios compared to vehicle (FIGS. 5B, C). Twice daily tivantinib (200 mg/kg BID) combined with pazopanib returned the pMET:MET ratios to vehicle-treated levels, whereas daily tivantinib treatment (200 mg/kg QD) caused an intermediate effect (FIGS. 5B, C). To determine whether the underlying changes in MET levels were associated with hypoxia induced by VEGFR/PDGFR inhibition, HIF-1α levels were measured using a validated HIF-1α immunoassay (21). Pazopanib-induced increases in pMET:MET ratios were accompanied by a 46% increase in HIF-1α levels ($p<0.05$), whereas the addition of tivantinib returned HIF-1α to vehicle-treated levels (FIG. 5D).

MET and pMET Levels in Clinical Cancer without MET Amplification: HPRC

The baseline levels of MET and pMET in human tumor models without MET amplification (FIG. 1D) are low, lying near the assay lower limit of quantitation; therefore drug-induced decreases in pMET:MET ratios often cannot be quantified in these models. To address the question whether or not MET and pMET levels in preclinical models and in clinical cancer without substantial MET amplification are similar, core needle biopsies of five regions of a resected HPRC tumor harboring a germ line MET mutation (H1112R) were evaluated. HPRC is characterized by germ-line trisomy of chromosome 7, frequent expression of two copies of mutated MET and one copy of wild-type MET (27, 28), and decreased activation threshold of the kinase activity and enhanced transforming activity (15), so HPRC was a non-amplified disease in which pMET quantitation seemed likely. As expected, full-length MET levels ranged from 0.073 to 0.368 fmol/μg protein (Table 2), similar to nonamplified models. However, pY1234/1235-MET was measurable in only two of five cores (0.037 and 0.041 fmol/μg), and neither pY1235-MET nor pY1356-MET were detectable in any core specimen.

Figure 6A:
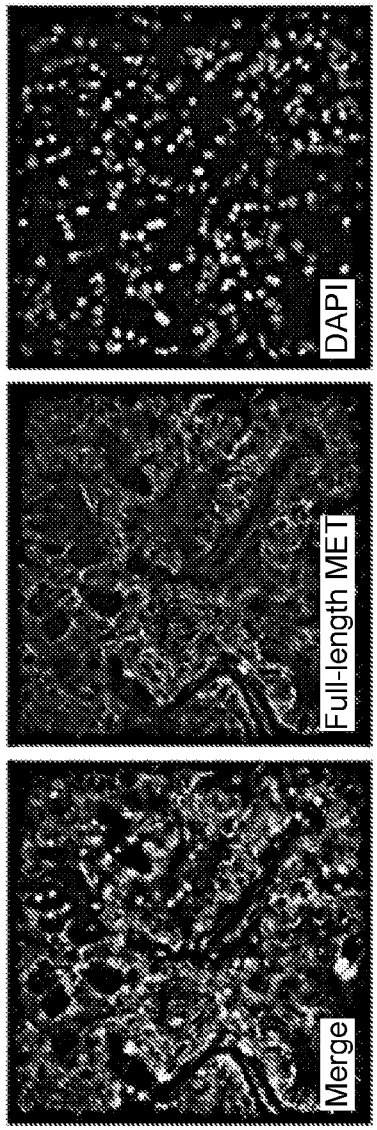
FIG. 6. MET assessment in core biopsies of a surgically resected HPRC tumor. (A) Immunofluorescence staining of a section from a formalin-fixed, paraffin-embedded core needle specimen of a resected HPRC tumor. Merged and individual fluorescent images of N-terminus MET staining with AF276 antibody (pink; primarily membrane) and nuclear staining with DAPI. Magnification, 40+. (B) Tissue extracts of HPRC core biopsies sequentially analyzed by Western blot using antibodies against pY1235-MET (clone 23111), pY1234/1235-MET (clone D26), N-terminal MET (AF276), and C-terminal MET (L41G3). Anti-pY1235-MET primarily recognizes a truncated, C-terminal form of MET, while anti-pY1234/1235-MET recognizes mostly full-length MET. In addition, a minor protein band>170 kDa was detected with the MET N-terminal specific antibody, which is not recognized by the other MET antibodies. The MET N-terminal-specific antibody also recognizes a truncated N-terminal MET fragment. Sample load was 25-50 μg protein per gel lane. The numbers ("2" and "3") indicate the specimen numbers described in Table 2.
Figure 6B:
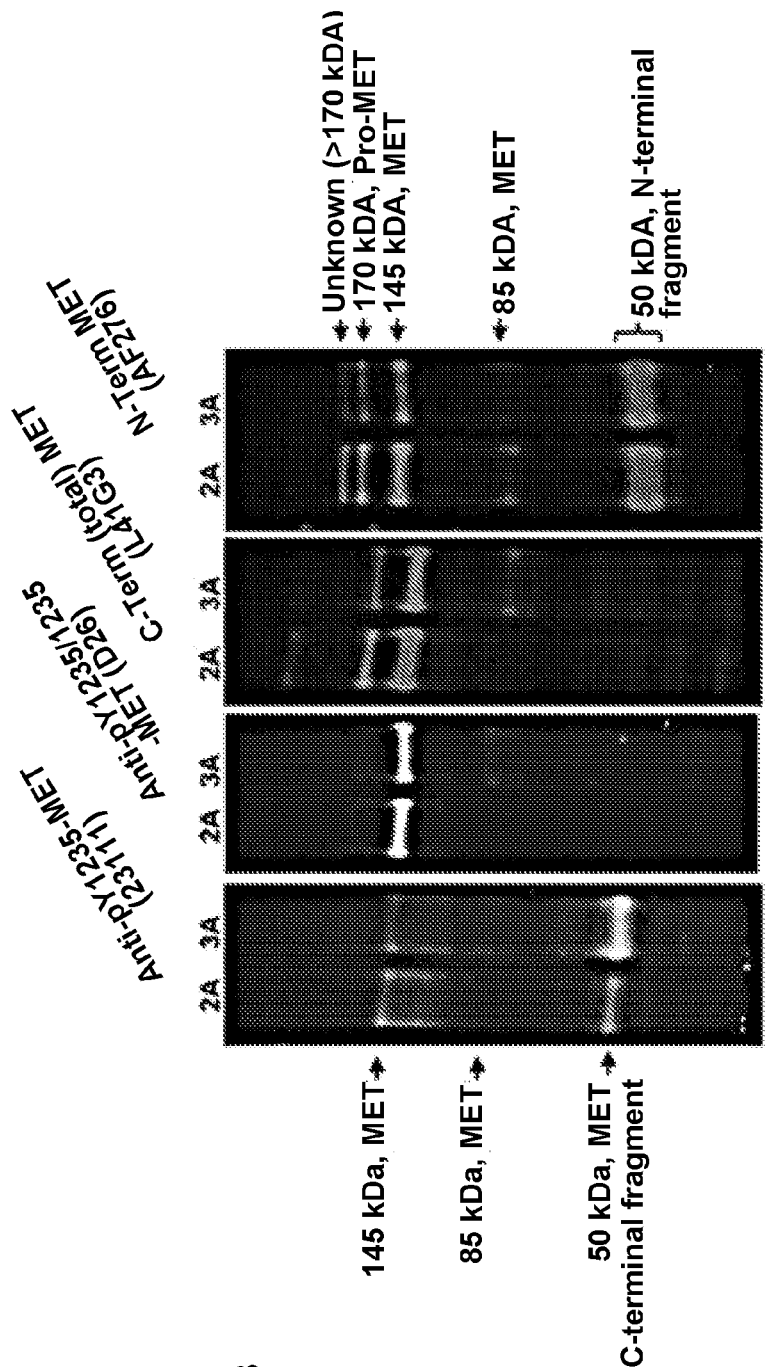

Immunofluorescence staining of sections of the HPRC cores with the capture antibody from the immunoassay (AF276, anti-MET extracellular domain) confirmed the presence of MET in the HPRC cells and localized it primarily to the plasma membrane (FIG. 6A). Western blotting revealed that the undetectable level of pY1235-MET in the immunoassay was due in large part to the association of the epitope with a truncated C-terminal 50 kDa MET fragment (FIG. 6B), which is too small to contain the N-terminal domain required for capturing full-length MET in the validated sandwich immunoassay. A small amount of full-length MET containing the pY1235 epitope was detectable by Western blotting, but detection required loading the gel lane with 25-50 μg total protein, which exceeds the amount of protein that can be used in the immunoassay while maintaining assay linearity (FIG. 1D). Interestingly, the antibody against pY1234/1235-MET (clone D26) recognized mainly full-length MET (FIG. 6B), which is why it was detectable in the immunoassay.

Discussion

Biochemical signaling from activated MET drives both proliferation and migration of malignant cells (1, 2), and MET can be activated not only by conventional ligand binding of paracrine and autocrine HGF but also by several ligand-independent mechanisms. Transphosphorylation of Y1235 in the kinase domain initiates signaling, and subsequent phosphorylation of Y1349 and Y1356 in the SH2 binding motif transduces signaling, with phosphorylation of Y1356 critical for growth factor receptor bound protein 2 docking that may link MET to the RAS pathway (29, 30), analogous to EGFR signaling. Several pharmacological classes of MET inhibitors target these key phosphorylation events, so the extent of phosphorylation of the critical tyrosine residues should be a highly informative PD biomarker of molecular drug action. The results described herein demonstrate that the phosphorylation status of the key tyrosine residues in full-length ligand-responsive MET is quantifiable using a dual-epitope sandwich-immunoassay platform with newly generated monoclonal antibodies specific for pY1356 and for pY1235 (independent of phosphorylation status of the adjacent Y1234 residue). Also in some embodiments, to obtain valid assay results, cold ischemia time can be limited to 2 min to preserve the phosphorylated analytes. For preclinical PD studies in xenograft models, a human pMET:MET ratio normalizes pMET to total MET and mitigates the confounding effect of mouse cell infiltration as tumors grow (20).

Daily dosage regimens of two MET TKIs achieved tumor control and PD responses in GTL-16 and SNU5 human tumor xenograft models of poorly differentiated gastric carcinoma driven by MET-amplification (31, 32). Tumor control of GTL-16 with PHA665752, a highly selective, ATP-competitive inhibitor of MET RTK activity (33), was associated with a 60-80% reduction in the pY1235-MET:MET ratio 4 h after the first dose, but the ratio fully recovered by 24 h and was less responsive to subsequent days of therapy. Treating GTL-16 with PF02341066, a potent, orally bioavailable, ATP-competitive inhibitor of MET catalytic activity (34), achieved tumor control at the only dose level that elicited a PD response (a consistent 65-90% reduction in the pY1235-MET:MET ratio throughout the 24-hour dosing interval). The pY1356-MET:MET ratio was consistently less responsive to drug therapy than the pY1235-MET:MET ratio in both tumor models and with both MET TKIs, suggesting GRB2 signaling is more difficult to inhibit than MET kinase activity.

60-90% reductions in the pY1235-MET:MET ratio were associated only with tumor stasis, but not regression. Therefore, a greater than commonly seen MET PD response, i.e., the magnitude and/or duration of pY1235-MET inhibition, or the addition of pY1356-MET inhibition (also linked to tumor regression) (35) may in some cases be needed to induce tumor regression in MET-amplified models. Clinical benefit from MET-directed therapy has been limited to patients with high baseline MET expression (36-39), but these assessments were made without a validated PD biomarker for activated MET or knowledge of the effect of warm ischemia on full-length MET degradation. Therefore, the trials to date unfortunately represent missed opportunities to understand clinical PD responses elicited by current MET inhibitors that could guide their future clinical development (40). The newly developed and validated assays described herein are suitable for defining the PD response associated with tumor regression both in preclinical models and human patients with MET amplified cancers. The analytical performance of the assays is sufficient for conducting small, fast phase 0 clinical trials of various dosage regimens of investigational MET inhibitors to discover how to maintain over 90% target suppression during dosing intervals (41, 42). From our error modeling, considering both biological variability and assay precision, clinical PD study designs based on longitudinal patient sampling should require decreases in pMET:MET ratios of at least 45% (the LSC value) to attribute them to drug effect.

In addition to MET amplification with its relatively high baseline pMET:MET ratios, assay fitness-for-purpose was also demonstrated in a MET-induction setting during compensatory responses to tumor hypoxia. Induction of MET signaling converts a tumor from low to measurably high MET and pMET levels, which become targets of MET TKI therapy. We found that pharmacological targeting of tumor vasculature in SNU5 xenografts with pazopanib, a multi-kinase inhibitor, induced the hypoxia biomarker Hif-1α and increased pY1235-MET:MET and pY1356-MET:MET ratios. Although twice daily treatment with tivantinib, an allosteric inhibitor of MET (6, 7, 26) with some effects on microtubules (43-45), did not reduce baseline MET or pMET levels, it nevertheless blocked pazopanib-induced HIF-1α MET signaling. Several molecular mechanisms could explain why tivantinib blocked pMET increases induced by pazopanib, including blocking the microtubule dependent co-clustering of MET and VEGFR2 or prolonging PTP1B (protein tyrosine phosphatase, non-receptor type 1) inhibition of MET (43, 44, 46). Clinical trials of MET/VEGF inhibitor combinations [pazopanib/tivantinib (NCT01468922) and bevacizumab/tivantinib (NCT01749384)] provide an opportunity for correlative PD studies to determine if this compensatory mechanism operates in clinical cancers, and the preclinical modeling of one of these trials demonstrated that the validated pMET immunoassay is a suitable tool for these studies.

This newly developed and validated immunoassay for PD biomarkers of MET molecular response is a robust tool for understanding and optimizing pharmacological control of both amplified and induced MET signaling, and it is ready for training-based transfer to the research community by the NCI (http://dctd.cancer.gov/ResearchResources/ResearchResources-biomarkers.htm). Phosphorylation of Y1235 is the proposed first step of MET signaling upon ligand binding, and the specificity of the new mAb for phosphorylated Y1235 independent of the phosphorylation status of the adjacent Y1234 residue will be useful for teasing apart the role of these neighboring tyrosines during initiation of MET signaling and molecular response to MET TKIs. Importantly, the anti-pY1235 mAb we generated (clone 23111) exhibited much greater specificity than the anti-pY1234/1235 mAb (clone D26), which even recognized a recombinant GST-MET protein harboring a Y1235D substitution. Our studies found that PD responses of the pY1235 and pY1234/1235 biomarkers did not always correspond. Furthermore, both pY1235 and pY1234/1235 epitopes were identified in full-length MET extracted from an HPRC tissue sample, while the pY1235 epitope was mostly present in a 50 kDa MET fragment. Similarly complex phosphorylation profiles have been found in non-small cell lung cancer in which only 25% of MET+ cases were also positive for pY1234/1235-MET (47). The pY1235-specific antibody, or an immunological binding reagent derived therefrom, could be a key reagent in a new diagnostic test for selecting the right patients to receive MET-targeted therapies because it substitutes the phosphorylated MET kinase domain (48) in place of elevated MET, mRNA, gene copy number, co-localized proteins, or multiply phosphorylated epitopes (49, 50). In contrast, unlike the validated immunoassay described herein, cross-reactivity to MET fragments with undefined biological significance may confound previously reported immunohistochemical tests of MET signaling (26, 37, 51-53).

REFERENCES

1. Engelman J A, Zejnullahu K, Mitsudomi T, Song Y, Hyland C, Park J O, et al. MET amplification leads to gefitinib resistance in lung cancer by activating ERBB3 signaling. Science 2007; 316:1039-43.

2. Guo A, Villen J, Kornhauser J, Lee K A, Stokes M P, Rikova K, et al. Signaling networks assembled by oncogenic EGFR and c-Met. Proc Natl Acad Sci USA 2008; 105:692-7.

3. Brooks A N, Choi P S, de Waal L, Sharifnia T, Imielinski M, Saksena G, et al. A pan-cancer analysis of transcriptome changes associated with somatic mutations in U2AF1 reveals commonly altered splicing events. PLoS One 2014; 9:e87361.

4. Eder J P, Shapiro G I, Appleman L J, Zhu A X, Miles D, Keer H, et al. A phase I study of foretinib, a multi-targeted inhibitor of c-Met and vascular endothelial growth factor receptor 2. Clin Cancer Res 2010; 16:3507-16.

5. Trusolino L, Bertotti A, Comoglio P M. MET signalling: principles and functions in development, organ regeneration and cancer. Nat Rev Mol Cell Biol 2010; 11:834-48.

6. Eathiraj S, Palma R, Hirschi M, Volckova E, Nakuci E, Castro J, et al. A novel mode of protein kinase inhibition exploiting hydrophobic motifs of autoinhibited kinases: discovery of ATP-independent inhibitors of fibroblast growth factor receptor. J Biol Chem 2011; 286:20677-87.

7. Eathiraj S, Palma R, Volckova E, Hirschi M, France D S, Ashwell M A, et al. Discovery of a novel mode of protein kinase inhibition characterized by the mechanism of inhibition of human mesenchymal-epithelial transition factor (c-Met) protein autophosphorylation by ARQ 197. J Biol Chem 2011; 286:20666-76.

8. Eder J P, Vande Woude G F, Boerner S A, LoRusso P M. Novel therapeutic inhibitors of the c-Met signaling pathway in cancer. Clin Cancer Res 2009; 15:2207-14.

9. Kurzrock R, Sherman S I, Ball D W, Forastiere A A, Cohen R B, Mehra R, et al. Activity of XL184 (Cabozantinib), an oral tyrosine kinase inhibitor, in patients with medullary thyroid cancer. J Clin Oncol 2011; 29:2660-6.

10. Rodig S J, Shapiro G I, Crizotinib, a small-molecule dual inhibitor of the c-Met and ALK receptor tyrosine kinases. Curr Opin Investig Drugs 2010; 11:1477-90.

11. Santoro A, Rimassa L, Borbath I, Daniele B, Salvagni S, Van Laethem J L, et al. Tivantinib for second-line treatment of advanced hepatocellular carcinoma: a randomised, placebo-controlled phase 2 study. Lancet Oncol 2013; 14:55-63.

12. Surati M, Patel P, Peterson A, Salgia R. Role of MetMAb (OA-5D5) in c-MET active lung malignancies. Expert Opin Biol Ther 2011; 11:1655-62.

13. Lefebvre J. Ancot F, Leroy C, Muharram G, Lemiere A, Tulasne D. Met degradation: more than one stone to shoot a receptor down. FASEB J 2012; 26:1387-99.

14. Zhu H, Naujokas M A, Fixman E D, Torossian K, Park M. Tyrosine 1356 in the carboxyl-terminal tail of the HGF/SF receptor is essential for the transduction of signals for cell motility and morphogenesis. J Biol Chem 1994; 269:29943-8.

15. Chiara F, Michieli P, Pugliese L, Comoglio P M. Mutations in the met oncogene unveil a "dual switch" mechanism controlling tyrosine kinase activity. J Biol Chem 2003; 278:29352-8.

16. Voortman J, Harada T, Chang R P, Killian J K, Suuriniemi M, Smith W I, et al. Detection and therapeutic implications of c-Met mutations in small cell lung cancer and neuroendocrine tumors. Curr Pharm Des 2013; 19:833-40.

17. Plowman J, Dykes D, Hollingshead M, Simpson-Herren L, Alley M. Human tumor xenograft models in NCI drug development. In: Teicher B, editor. Anticancer drug development guide Preclinical screening, clinical trials, and approvaled. Totowa, N.J.: Humana Press Inc.; 1997. p. 101-25.

18. Pfister T D, Hollingshead M, Kinders R J, Zhang Y, Evrard Y A, Ji J, et al. Development and validation of an immunoassay for quantification of topoisomerase I in solid tumor tissues. PLoS One 2012; 7:e50494.

19. Kinders R J, Hollingshead M, Khin S, Rubinstein L, Tomaszewski J E, Doroshow J H, et al. Preclinical modeling of a phase 0 clinical trial: qualification of a pharmacodynamic assay of poly (ADP-ribose) polymerase in tumor biopsies of mouse xenografts. Clin Cancer Res 2008; 14:6877-85.

20. Alcoser S Y, Kimmel D J, Borgel S D, Carter J P, Dougherty K M, Hollingshead M G. Real-time PCR-based assay to quantify the relative amount of human and mouse tissue present in tumor xenografts. BMC Biotechnol 2011; 11:124.

21. Park S R, Kinders R J, Khin S, Hollingshead M, Parchment R E, Tomaszewski J E, et al. Validation and fitness testing of a quantitative immunoassay for HIF-1 alpha in biopsy specimens. Cancer Res 2012; Cancer Res 2012; 72(8 Suppl):Abstract nr 3616:8.

22. Kinders R J, Hollingshead M, Lawrence S, Ji J, Tabb B, Bonner W M, et al. Development of a validated immunofluorescence assay for gammaH2AX as a pharmacodynamic marker of topoisomerase I inhibitor activity. Clin Cancer Res 2010; 16:5447-57.

23. Baker A F, Dragovich T, Ihle N T, Williams R, Fenoglio-Preiser C, Powis G. Stability of phosphoprotein as a biological marker of tumor signaling. Clin Cancer Res 2005; 11:4338-40.

24. Neumeister V M, Parisi F, England A M, Siddiqui S, Anagnostou V, Zarrella E, et al. A tissue quality index: an intrinsic control for measurement of effects of preanalytical variables on FFPE tissue. Lab Invest 2014; 94:467-74.

25. Wolf C, Jarutat T, Vega Harring S, Haupt K, Babitzki G, Bader S, et al. Determination of phosphorylated proteins in tissue specimens requires high-quality samples collected under stringent conditions. Histopathology 2014; 64:431-44.

26. Yap T A, Ohmos D, Brunetto A T, Tunariu N, Barriuso J, Riisnaes R, et al. Phase trial of a selective c-MET inhibitor ARQ 197 incorporating proof of mechanism pharmacodynamic studies. J Clin Oncol 2011; 29:1271-9.

27. Zhuang Z, Park W S, Pack S, Schmidt L. Vortmeyer A O, Pak E, et al. Trisomy 7-harbouring non-random duplication of the mutant MET allele in hereditary papillary renal carcinomas. Nat Genet 1998; 20:66-9.

28. Schmidt L, Junker K, Weirich G, Glenn G, Choyke P, Lubensky I, et al. Two North American families with hereditary papillary renal carcinoma and identical novel mutations in the MET proto-oncogene. Cancer Res 1998; 58:1719-22.

29. Hartmann G, Weidner K M, Schwarz H, Birchmeier W. The motility signal of scatter factor/hepatocyte growth factor mediated through the receptor tyrosine kinase met requires intracellular action of Ras. J Biol Chem 1994; 269:21936-9.

30. Cepero V, Sierra J R, Corso S, Ghiso E, Casorzo L, Perera T, et al. MET and KRAS gene amplification mediates acquired resistance to MET tyrosine kinase inhibitors. Cancer Res 2010; 70:7580-90.

31. Rege-Cambrin G, Scaravaglio P, Carozzi F, Giordano S, Ponzetto C, Comoglio P M, et al. Karyotypic analysis of gastric carcinoma cell lines carrying an amplified c-met oncogene. Cancer Genet Cytogenet 1992; 64:170-3.

32. Park J G, Frucht H, LaRocca R V, Bliss D P, Jr., Kurita Y, Chen T R, et al. Characteristics of cell lines established from human gastric carcinoma. Cancer Res 1990; 50:2773-80.

33. Christensen J G, Schreck R, Burrows J, Kuruganti P, Chan E, Le P, et al. A selective small molecule inhibitor of c-Met kinase inhibits c-Met-dependent phenotypes in vitro and exhibits cytoreductive antitumor activity in vivo. Cancer Res 2003; 63:7345-55.

34. Zou H Y, Li Q, Lee J H, Arango M E, McDonnell S R, Yamazaki S, et al. An orally available small-molecule inhibitor of c-Met, PF-2341066, exhibits cytoreductive antitumor efficacy through antiproliferative and antiangiogenic mechanisms. Cancer Res 2007; 67:4408-17.

35. Rikova K, Guo A, Zeng Q. Possemato A, Yu J, Haack H, et al. Global survey of phosphotyrosine signaling identifies oncogenic kinases in lung cancer. Cell 2007; 131:1190-203.

36. Blumenschein G R, Jr., Mills G B, Gonzalez-Angulo A M. Targeting the hepatocyte growth factor-cMET axis in cancer therapy. J Clin Oncol 2012; 30:3287-96.

37. Knudsen B S, Zhao P, Resau J, Cottingham S. Gherardi E, Xu E, et al. A novel multipurpose monoclonal antibody for evaluating human c-Met expression in preclinical and clinical settings. Appl Immunohistochem Mol Morphol 2009; 17:57-67.

38. Miyamoto M, Ojima H, Iwasaki M, Shimizu H, Kokubu A, Hiraoka N, et al. Prognostic significance of overexpression of c-Met oncoprotein in cholangiocarcinoma. Br J Cancer 2011; 105:131-8.

39. Sattler M, Reddy M M, Hasina R, Gangadhar T, Salgia R. The role of the c-Met pathway in lung cancer and the potential for targeted therapy. Ther Adv Med Oncol 2011; 3:171-84.

40. Garber K. MET inhibitors start on road to recovery. Nat Rev Drug Discov 2014; 13:563-5.

41. Kummar S, Kinders R, Gutierrez M E, Rubinstein L, Parchment R E, Phillips L R, et al. Phase 0 clinical trial of the poly (ADP-ribose) polymerase inhibitor ABT-888 in patients with advanced malignancies. J Clin Oncol 2009; 27:2705-11.

42. Kummar S, Anderson L, Hill K, Majerova E, Allen D, Horneffer Y, et al. First-in-human phase 0 trial of oral 5-iodo-2-pyrimidinione-2'-deoxyribose in patients with advanced malignancies. Clin Cancer Res 2013; 19:1852-7.

43. Basilico C, Pennacchietti S, Vigna E, Chiriaco C, Arena S, Bardelli A, et al. Tivantinib (ARQ197) displays cytotoxic activity that is independent of its ability to bind MET. Clin Cancer Res 2013; 19:2381-92.

44. Katayama R, Aoyama A, Yamori T, Qi J, Oh-hara T, Song Y, et al. Cytotoxic activity of tivantinib (ARQ 197) is not due solely to c-MET inhibition. Cancer Res 2013; 73:3087-96.

45. Aoyama A, Katayama R, Oh-Nara T, Sato S, Okuno Y, Fujita N. Tivantinib (ARQ 197) exhibits antitumor activity by directly interacting with tubulin and overcomes ABC transporter-mediated drug resistance. Mol Cancer Ther 2014; 13:2978-90.

46. Lu K V, Chang J P, Parachoniak C A, Pandika M M, Aghi M K, Meyronet D, et al. VEGF inhibits tumor cell invasion and mesenchymal transition through a MET/VEGFR2 complex. Cancer Cell 2012; 22:21-35.

47. Tsuta K, Kozu Y, Mimae T, Yoshida A, Kohno T, Sekine I, et al. c-MET/phospho-MET protein expression and MET gene copy number in non-small cell lung carcinomas. J Thorac Oncol 2012; 7:331-9.

48. Furlan A, Kherrouche Z, Montagne R, Copin M C, Tulasne D. Thirty years of research on met receptor to move a biomarker from bench to bedside. Cancer Res 2014; 74:6737-44.

49. Scagliotti G V, Novello S, Schiller J H, Hirsh V, Sequist L V, Soria J C, et al. Rationale and design of MARQUEE: a phase III, randomized, double-blind study of tivantinib plus erlotinib versus placebo plus erlotinib in previously treated patients with locally advanced or metastatic, nonsquamous, non-small-cell lung cancer. Clin Lung Cancer 2012; 13:391-5.

50. Spigel D R, Edelman M J, Mok T, O'Byrne K, Paz-Ares L, Yu W, et al. Treatment Rationale Study Design for the MetLung Trial: A Randomized, Double-Blind Phase III Study of Onartuzumab (MetMAb) in Combination With Erlotinib Versus Erlotinib Alone in Patients Who Have Received Standard Chemotherapy for Stage IIIB or IV Met-Positive Non-Small-Cell Lung Cancer. Clin Lung Cancer 2012; 13:500-4.

51. Iveson T, Donehower R C, Davidenko I, Tjulandin S, Deptala A, Harrison M et al. Rilotumumab in combination with epirubicin, cisplatin, and capecitabine as first-line treatment for gastric or oesophagogastric junction adenocarcinoma: an open-label, dose de-escalation phase 1b study and a double-blind, randomised phase 2 study. Lancet Oncol 2014; 15:1007-18.

52. Spigel D R, Ervin T J, Ramlau R A, Daniel D B, Goldschmidt J H, Jr., Blumenschein G R, Jr., et al. Randomized phase II trial of Onartuzumab in combination with erlotinib in patients with advanced non-small-cell lung cancer. J Clin Oncol 2013; 31:4105-14.

53. Gruver A M, Liu L, Vaillancourt P, Yan S C, Cook J D, Roseberry Baker J A, et al. Inimunohistochemical application of a highly sensitive and specific murine monoclonal antibody recognising the extracellular domain of the human hepatocyte growth factor receptor (MET). Histopathology 2014; 65:879-96.

Supplementary Materials:

Development of Rabbit Monoclonal Antibodies Specific for pY1235-MET and pY1356-MET The rationale for developing a monoclonal antibody against pY1235-MET was evidence that MET is phosphorylated sequentially, starting with Y1235, and that phosphorylation of just Y1235 in MET is sufficient to suppress the auto-inhibiting conformation of the enzyme and elicit activation of the kinase domain (1-4). It has also been suggested that some oncogenic forms of MET may overcome the need for phosphorylation of Y1234, the other key tyrosine in the kinase domain (3). Development of the second monoclonal antibody to measure the status of the multifunctional docking site of MET, which has two phospho-tyrosines near each other at Y1349-VHVNAT-Y1356-VNV, focused on the Y1356 site (5). Phosphorylation of MET at both Y1349 and Y1356 are required for the transforming function of the receptor (6); however, mutation of Y1356 completely abrogates the transforming ability of the MET receptor to mediate cell motility, invasion, and morphogenesis (2). In contrast, evidence suggests that under certain conditions, phosphorylation of the Y1349 site is dispensable for these purposes (7). Thus, specifically assessing the phosphorylation status of the Y1234/1235 and Y1356 sites could potentially discriminate MET tyrosine kinase inhibitor (TKI) mechanisms of action and MET receptor transforming activity.

Rabbit monoclonal antibodies specific to pY1235-MET (with undetectable reactivity to pY1234-MET) and pY1356-MET were developed by Epitomics, Inc: (San Francisco, Calif.) using 10-12 amino acid-long synthetic peptide antigens corresponding to the MET sequences surrounding Y1235 and Y1356. Rabbits were selected for splenectomy and B-cells were subsequently fused with the rabbit cell line 240E-W2 to produce hybridomas based on high antiserum binding to phosphorylated synthetic peptide and lower or undetectable binding to the nonphosphorylated synthetic peptide of identical sequence. Specificity of the pY1235-MET antibody (clone 23111) was tested by preincubating the antibody with synthetic MET peptides phosphorylated at Y1235 (99% phosphorylated at Y1235, nonphosphorylated at Y1234, 1% other impurities) or at Y1234, or preincubating with recombinant RON (cytoplasmic domain, Millipore) (FIG. 7A). Only preincubation with the pY1235 peptide blocked binding of the antibody to the MET protein band. Specificity of clone 23111 was further confirmed by Western blotting of a GST-fusion with MET amino acids 912-1390 harboring a Y1235D-specific mutation (N-terminal GST-Y1235D-MET peptide, 76 kDa; CarnaBio USA, Inc) and of a recombinant cytoplasmic domain of RON (FIG. 7B). The pY1235-MET antibody (clone 23111) had undetectable cross-reactivity to the recombinant Y1235D-MET peptide, which is presumably phosphorylated at Y1234-MET (3, 4). Probing with the commercially available anti-pY1234/1235-MET (clone D26, Cell Signaling Technology) antibody identified a band corresponding to the recombinant Y1235D-MET peptide (FIG. 7B). According to the manufacturer's specifications, anti-pY1234/1235-MET (clone D26) can also bind to tyrosine phosphorylated SRC proteins by Western blot.

Specificity of the pY1356-MET antibody (clone 7334) was established by its ability to bind MET in cell lysates and its recognition of phosphorylated but not nonphosphorylated synthetic peptides containing Y1356 and its surrounding amino acid sequence (FIG. 7C). Reactivity of all four antibodies used in this study against recombinant MET was confirmed by Western blotting (FIG. 7D).

To facilitate bulk production, rabbit monoclonal antibodies (clones 23111 and 7334) were converted into recombinant proteins through transient expression in HEK293 cells (8). The cDNA from rabbit hybridomas was used to clone IgG heavy and light chains in a 7.7 kB ampicillin-resistant mammalian expression vector co-expressing EB oriP, zeocin selection, and CMV promoter for transient expression in HEK293 cells. For mammalian expression plasmids, DNA was prepared using the GenElute XP Maxiprep kit (Sigma-Aldrich) and verified by agarose gel electrophoresis. Recombinant protein production provided typical yields of 100-300 mg/L in suspension cultures. Specificity of antibodies, determined by Western blot using xenograft lysate and rMET protein, was unaffected by this process. To further characterize these MET antibodies, their binding affinities were measured over a range of protein concentrations using interaction analysis performed with a BIAlite-Biosensor (Pharmacia) as previously described (9). The pY1235- and pY1356-MET antibodies exhibited nanomolar affinities for their targets, with $IC_{50}$ values of 1.2 nM and 5.6 nM, respectively (details not shown).

Production of Recombinant MET Calibrator Protein

Figure 12B:
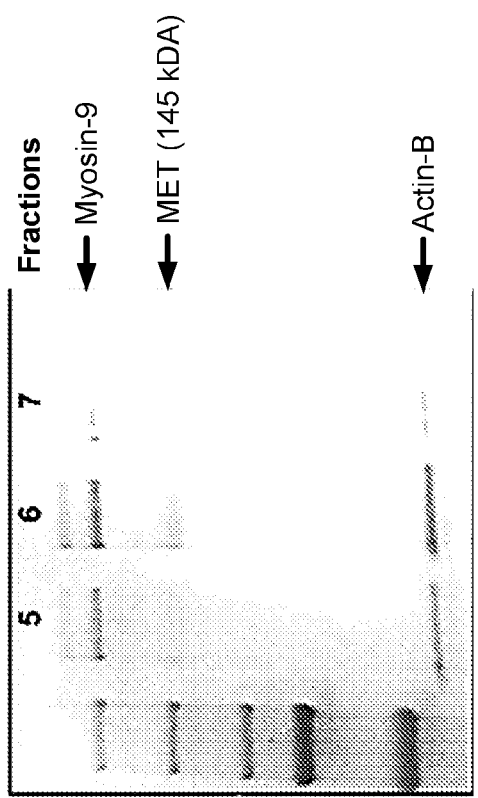
FIG. 12: Purification of rMET protein for use as an assay calibrator. (A) ELISA analysis of affinity-purified fractions from a membrane preparation of HEK293 cells over-expressing wild type rMET (Swiss Prot P08581). (B) Electrophoresis (SDS-PAGE) of peak fractions 5, 6, and 7 from affinity purification stained by Coomassie blue. (C) MALDI-TOF analysis of the 145 kDa protein extracted from gel slices of the SDS-PAGE gel. MALDI-TOF mass was assigned to three different peptides (MET signature) verified by Mascot database (Matrix Science). (D) MET protein sequence (SEQ ID NO: 13) with MET signature peptides highlighted: peak M1 (aa1220-1227, VADFGLAR (SEQ ID NO: 14)); peak M2 (aa418-426, TEFTTALQR (SEQ ID NO: 15)); peak M3 (aa568-580, VFPNSAPLEGGTR (SEQ ID NO: 16)).
Figure 12A:
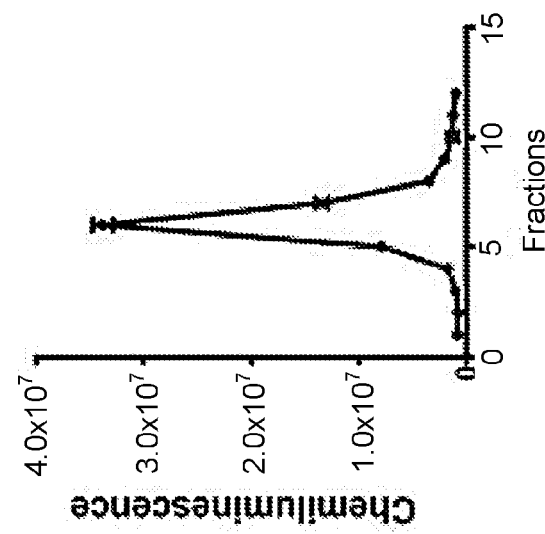
Figure 12C:
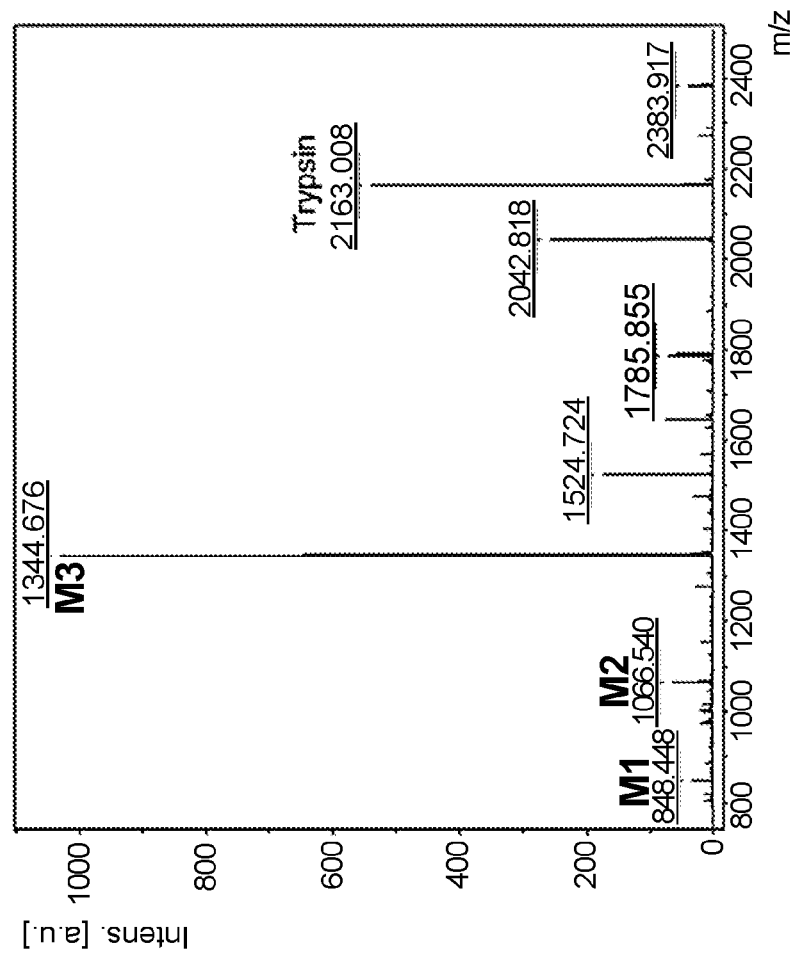

Recombinant MET (rMET, Swiss-Prot P08581, amino acids 1-1390) was cloned in a mammalian vector with a CMV promoter and a zeocin resistance marker and expressed transiently in HEK293 cells grown in suspension. Approximately 48-56 hours after transfection, membrane extracts were purified using an antibody (AF276; R&D Systems) affinity column. The transfected cells were lysed in CEB (Invitrogen) supplemented with 1% Triton X-100, PhosSTOP and protease inhibitor tablets (Roche), and the soluble fraction isolated by ultracentrifugation at 90,000×g, diluted with 1×PBS (pH 7.4) containing 1% Triton X-100, and incubated with an affinity column (circulated at 2° C. to 8° C. overnight). After washing the column with 0.5 M NaCl, rMET was eluted with pH 3.0 buffer and immediately neutralized by 0.5 M Tris buffer (pH 8.5) and stabilized by PhosSTOP and protease inhibitors. Fractions containing rMET were selected based on analysis using the full-length MET immunoassay (FIG. 12A). Purified rMET was characterized by SDS-PAGE analysis, MALDI-TOF, and Western blotting using antibodies specific for pY1235-MET (clone 23111), dual phosphorylated pY1234/1235-MET (clone D26), pY1356-MET (clone 7334), and C-terminal MET (clone L41G3) (FIG. 7D). Affinity-purified rMET eluted as minor fraction with two major proteins actin-B and myosin-9 (FIG. 12B); it was not clear if these proteins were bound to rMET or bound to the affinity column in a nonspecific manner. A band corresponding to 145 kDa was extracted from SDS-PAGE and verified as MET protein by MALDI-TOF signature (FIGS. 12C, D). The concentration of purified full-length rMET was assigned independently (details not shown) using a separate MET ELISA developed with a capture antibody that binds to cytoplasmic MET (Cell Signaling Technology, clone 25H2), a reporter antibody specific for C-terminal MET (clone L41G3), and cytoplasmic MET protein (956-1390 aa, Calbiochem) as a calibrator (protein concentrations provided by manufacturer).

Validation of MET Immunoassays

The dynamic range of the full-length MET and pY1234/1235-MET assays was 0.3 to 40 pM while the dynamic range of the pY1235-MET and pY1356-MET assays was 3.125 to 200 pM (FIG. 7C). With a protein load of 20 µg/mL (the amount most often used in our studies), the LLQs of the assays were 0.015 fmol/µg protein for full-length and pY1234/1235-MET, 0.0625 fmol/µg protein for pY1235-MET, and 0.16 fmol/µg protein for pY1356-MET; where other protein loads were used, the LLQ for that protein load is specified. The MET immunoassays were subjected to a rigorous validation protocol for analytical performance using clinically relevant specimen collection and preparation procedures. In addition, all assays were transferred from the development laboratory (Pharmacodynamic Assay Development & Implementation Section, Laboratory of Human Toxicology and Pharmacology, Leidos Biomedical Research, Inc., Frederick, Md.) to the clinical testing laboratory (National Clinical Target Validation Laboratory, NCI, Bethesda, Md.) using SOP-driven transfers as previously described (10, 11). This interlaboratory transfer demonstrated the robustness of assay procedures. Before implementing the assays in preclinical and clinical studies for routine analysis of biopsy samples, daily quality control monitoring and batch-to-batch quality control testing criteria were introduced.

Inter-laboratory performance was determined using 8 matched samples originating from different xenograft extracts, with 3 extracts prepared by each laboratory. Extract dilutions were prepared independently at each site and adjusted to a final concentration of 10 to 50 µg/mL for MET analysis. Dilution recovery experiments were performed using A549, U87, SNU5, and GTL-16 xenograft samples. MET and pMET levels determined in the undiluted xenograft lysates were used to calculate the expected MET and pMET values in the samples diluted from one- to eight-fold with the assay buffer. Recovery was calculated as the pMET value from the diluted samples divided by the expected concentrations and expressed as a percentage. Three different mouse xenograft (pooled) samples were spiked with different known amounts of rMET (calibrator solution between 5 to 25 pM), and the matrix was minimally diluted by keeping the spiked solution at 10% of total volume. The MET and pMET values of unspiked xenograft samples mixed with an equivalent volume of assay buffer were used to evaluate spiked recovery. Recovery of added MET was calculated as ([final concentration−initial concentration]/added concentration) and expressed as percentage.

Western Blot Analysis

Protein concentrations were determined by bicinchoninic acid assay (BCA assay), and cell lysate loads between 25 and 50 µg per well were run on 4% to 20% precast polyacrylamide gradient gels (Bio-Rad Laboratories) for SDS-PAGE at 100 V for up to 2 hours. Proteins separated by gel electrophoresis were transferred to a nitrocellulose membrane using the Mini-PROTEAN Tetra electrophoresis system (Bio-Rad) at 90 V for 4 hours at 2° C. to 8° C. Membranes were blocked in Odyssey blocking buffer (LI-COR) for 1 hour at 25° C.±3° C. Blots were probed first with 1 µg/mL mouse, rabbit, or goat anti-MET monoclonal antibody in Odyssey blocking buffer overnight at 2° C. to 8° C. with slow orbital shaking and then with an IR dye-labeled secondary antibody against mouse, rabbit, or goat antibody (1:5000 in Odyssey blocking buffer; LI-COR) for 1 hour at 25° C.±3° C. with orbital shaking. Blots were visualized using the Odyssey Infrared imager (LI-COR). Blot photographs were cropped to improve presentation in figures.

Specificity of MET Immunoassays

The specificity of the capture antibody (AF276) was tested against the two most likely cross-reacting receptor tyrosine kinases, EGFR and RON, using recombinant extracellular-domain peptides as surrogates of full-length proteins to test cross-reactivity. Recombinant EGFR and RON proteins (extracellular domains, R&D Systems) were incubated at 10-fold higher (4 to 400 pM) concentration than rMET (0.4-40 pM) in the full-length MET immunoassay. In immunoassay format, the cross-reactivity of the AF276 antibody with the receptor tyrosine kinase RON was <5%, and no detectable cross-reactivity was observed with EGFR (data not shown).

Stability of pMET and Full-Length MET in Tissue Extracts

Samples of two xenograft tumor lysates were analyzed for freeze/thaw and storage stability at 25° C.±3° C. (cold ischemic stability) and 37° C. (warm ischemic stability) using the full-length and pY1235-MET assays. Up to five freeze/thaw cycles had minimal effect on MET and pY1235-

Figure 8A:
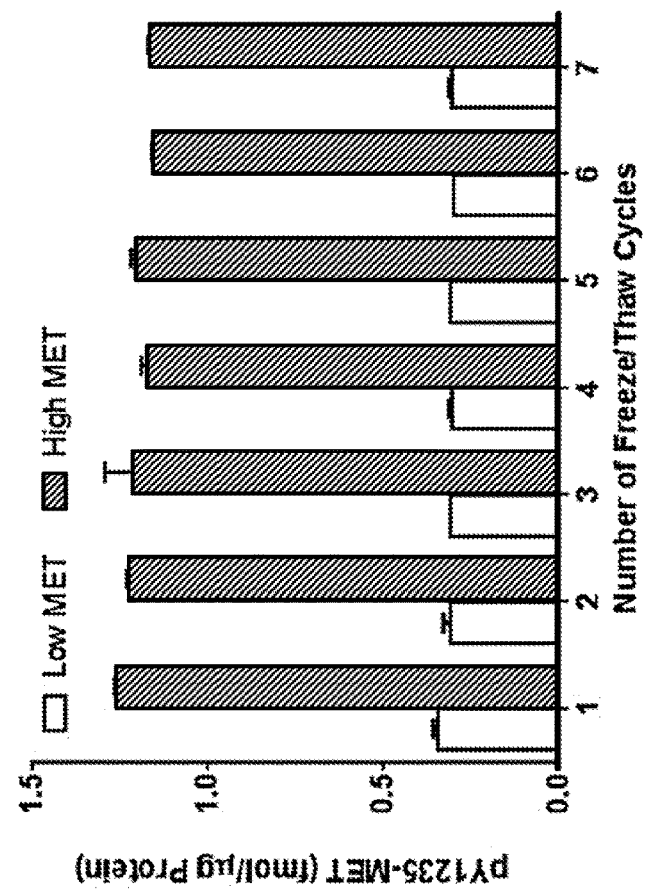
FIG. 8: Effect of freeze-thaw cycles and warm vs cold ischemia time on full-length and pMET levels. Ex vivo freeze-thaw stability of (A) MET and (B) pY1235-MET protein in tissue lysates with low and high levels of full-length MET. Temperature effect on stability of full-length MET and pY1235-MET in lysates with low (C) and high (D) MET levels; pY1235-MET is plotted as a ratio of full-length MET. Dashed lines (±10%) represent normal, within-assay variance for measurements; values exceeding 10% constitute deviation from normal.
Figure 8B:
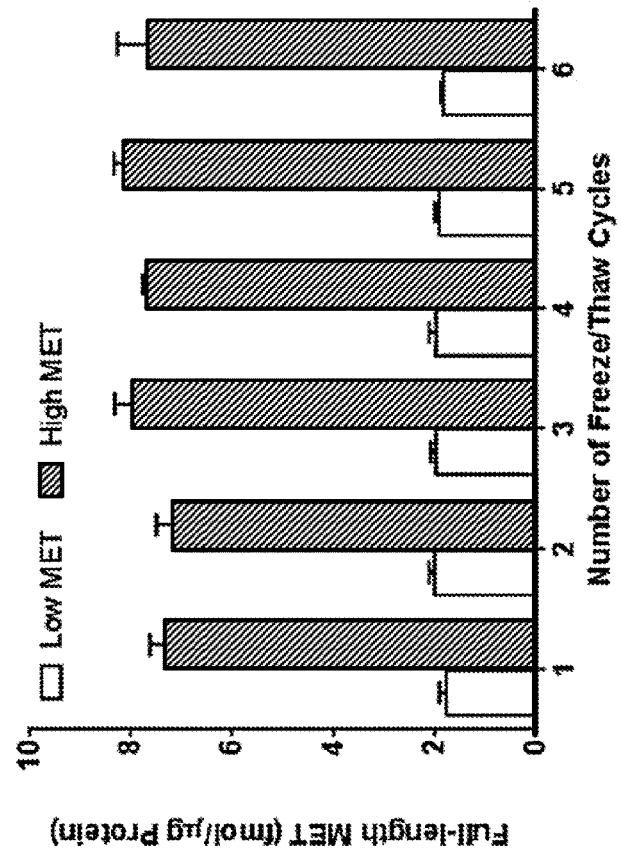
Figure 8D:
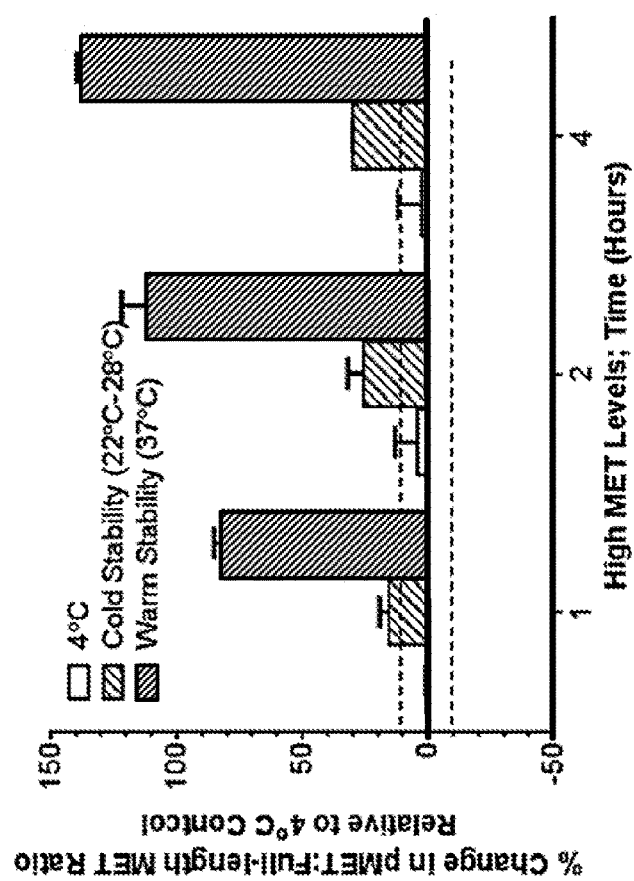
Figure 8C:
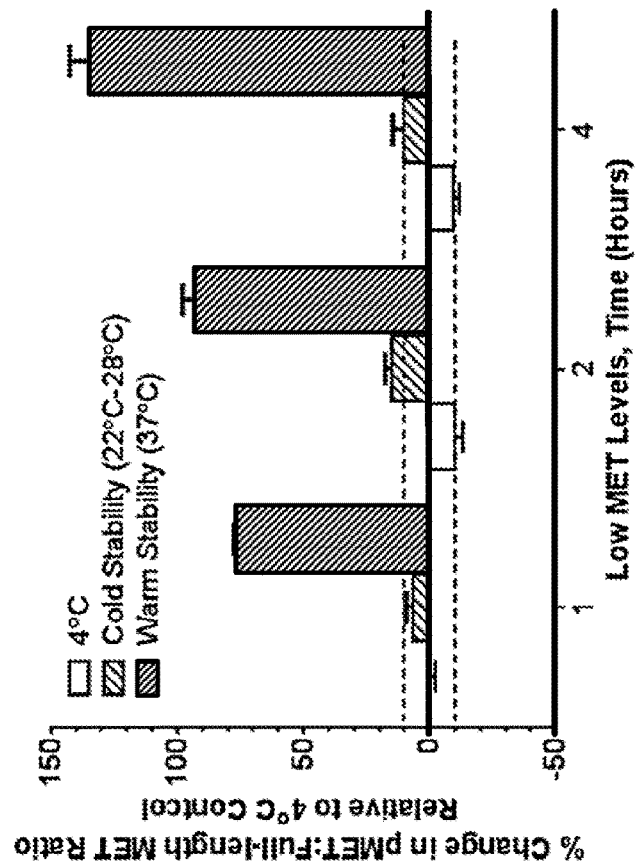

MET levels (FIGS. 8A, B). In addition, MET and pY1235-MET levels in lysates were stable for 4 hours at 2° C. to 8° C. and 2 hours at 25° C., indicating minimal impact on assay results (FIGS. 8C, D). However, there was a significant increase in the pY1235-MET:full-length MET ratio during storage at 37° C. but not at 2° C. to 8° C. or 25° C.±3° C., which could indicate phosphorylation of MET by kinases in the extracts that contained only phosphatase and protease inhibitors.

Figure 11A:
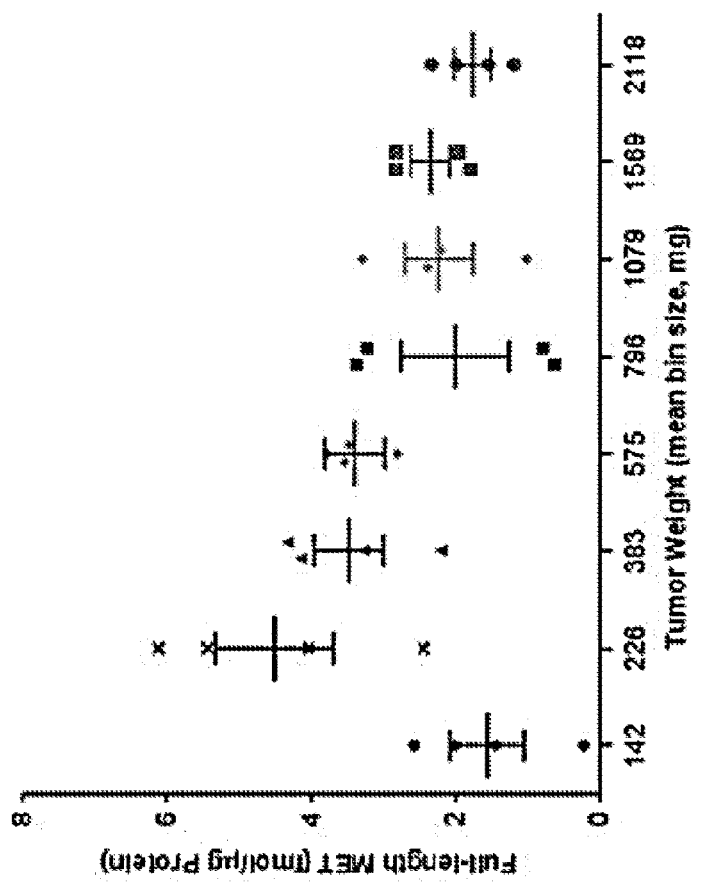
FIG. 11: Absolute MET levels decrease during SNU5 tumor growth due to mouse cell infiltration. (A) Tumor growth monitored over a 30-day period beginning 10-days after implantation. (B) Full-length MET and (C) human genome contribution, as a percentage of total human DNA, were analyzed in quadrants of xenografted tumors binned by size (x-axis represents mean tumor bin-size ranging from 142 mm$^3$ to 2118 mm$^3$). Error bars are mean±SD. (D) Correlation of tumor volume to levels of full-length MET (fmol/μg) in total protein lysates. (E) Correlation of tumor volume to levels of full-length MET normalized to human DNA (hDNA) content. (F) Variability (% CV) in the ratio of pY1234/1235-MET:MET in tumor quadrants and needle biopsies based on tumor size (n=4 tumors/group, except n=3 for 142 mm$^3$ group).
Figure 11B:
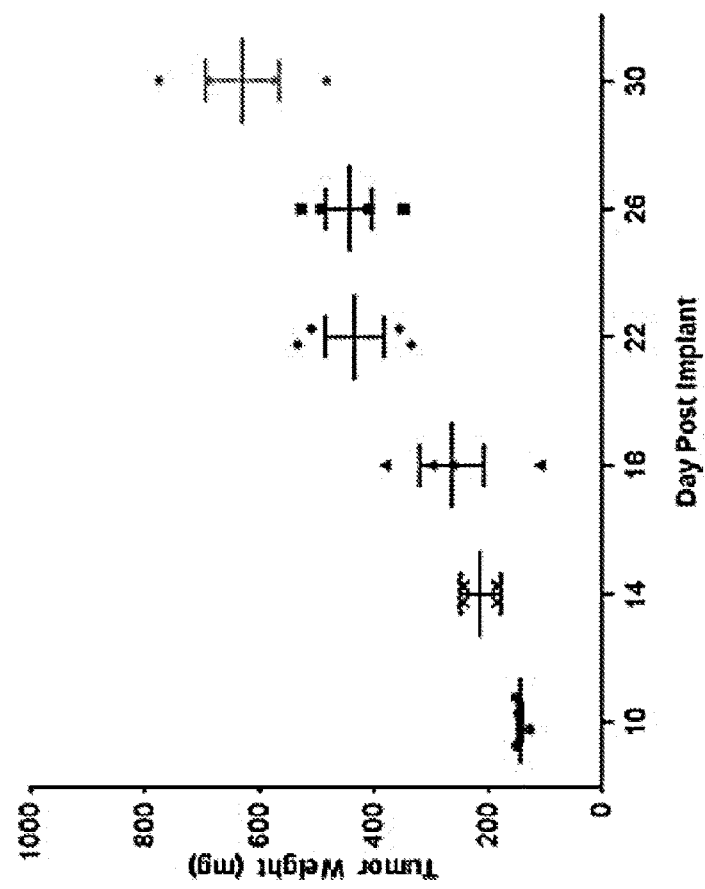
Figure 11C:
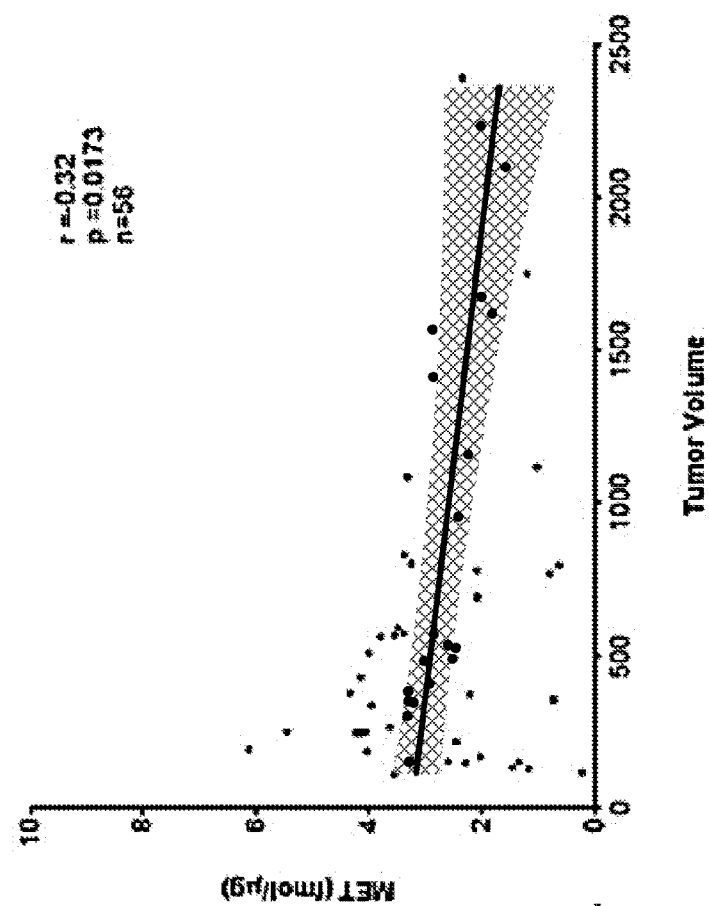
Figure 11D:
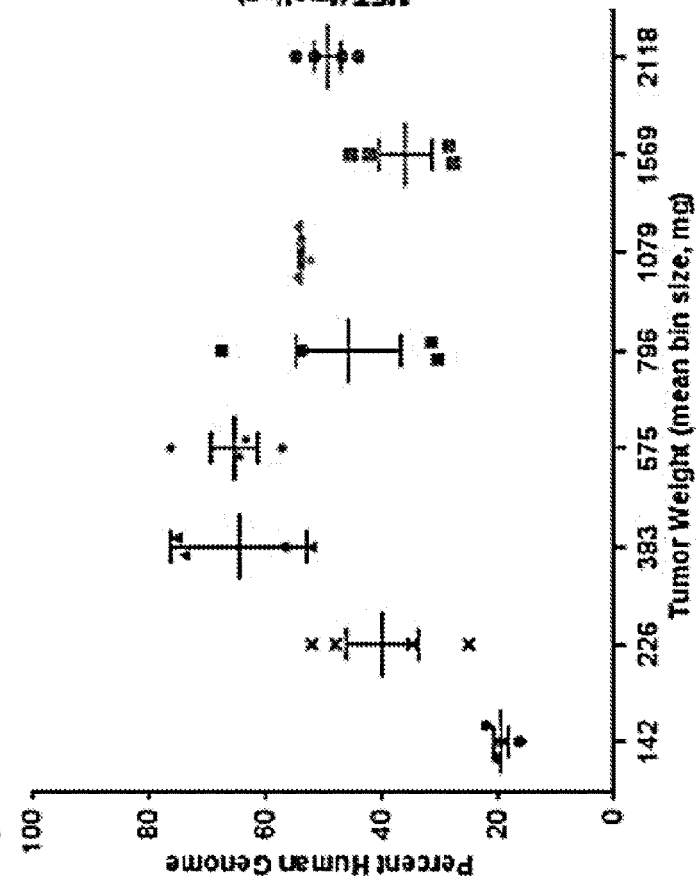
Figure 11F:
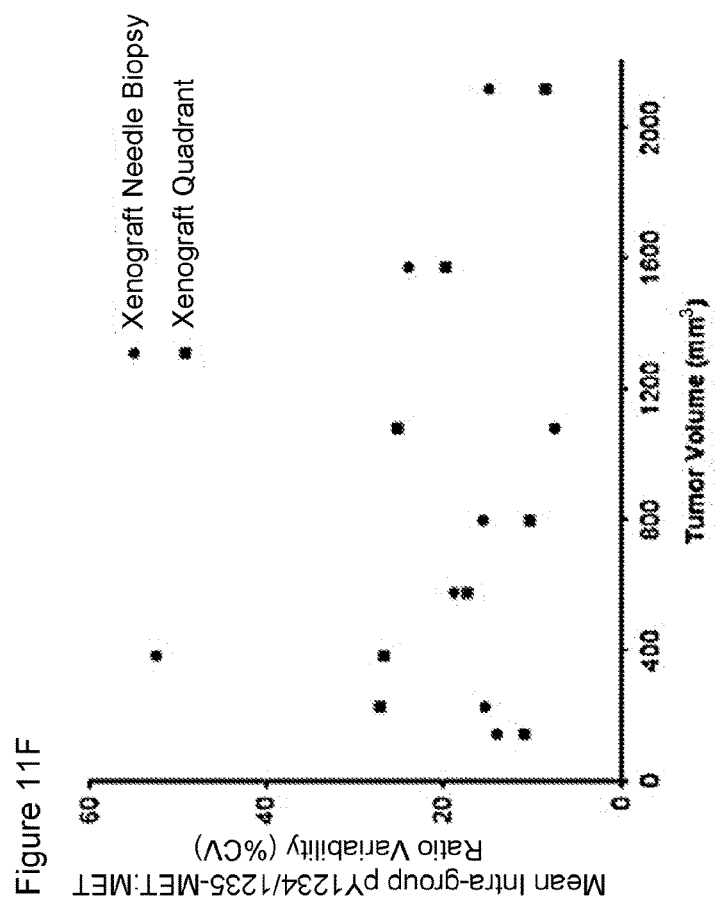
Figure 11E:
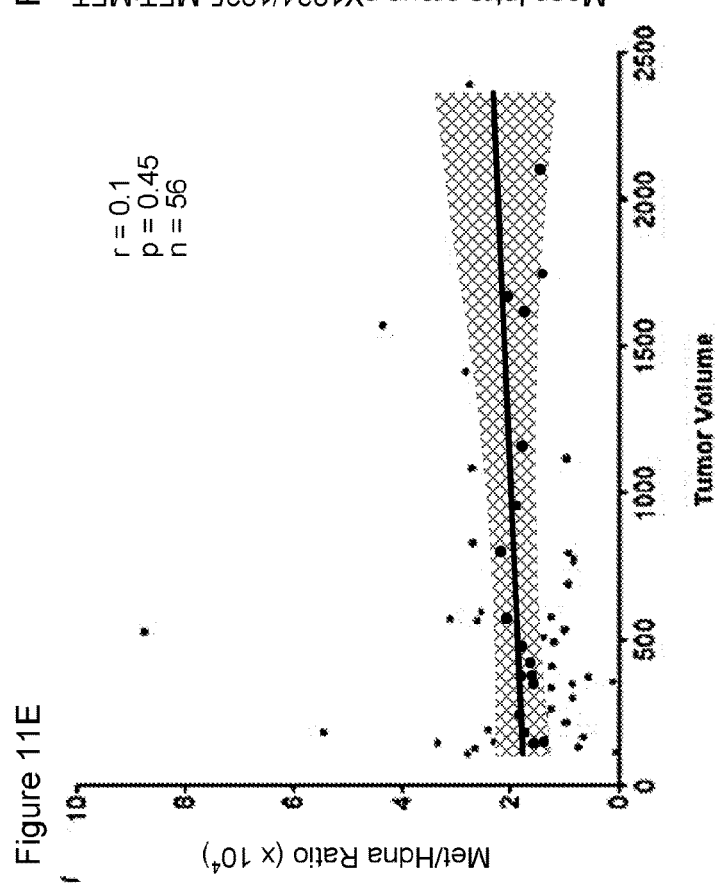
Figure 13A:
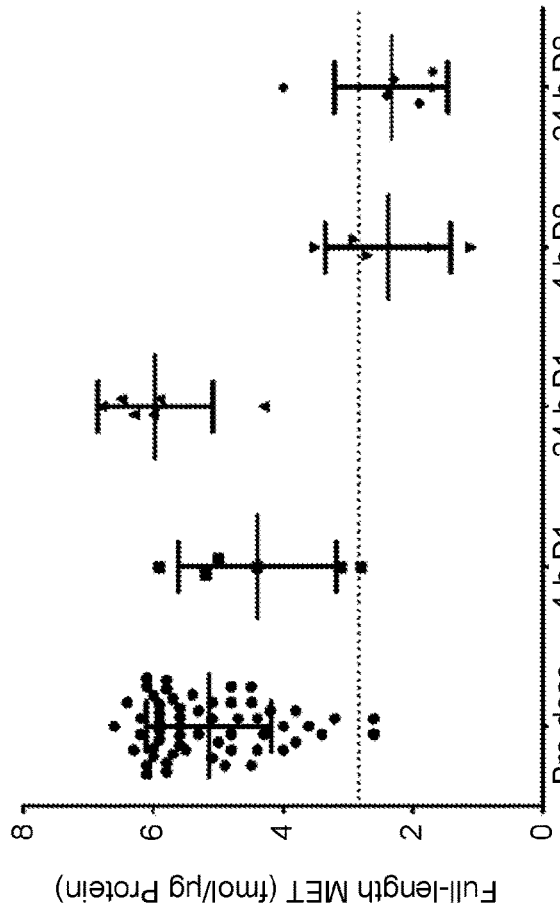
FIG. 13: Longitudinal values of MET and the pY1235-MET:MET ratio during growth of vehicle treated GTL-16 tumors. Mice bearing 200±25 mm$^3$ tumor xenografts were dosed daily for 8 days with PEG 400:20% vitamin E TPGS solution, 60:40 (the tivantinib vehicle). Needle biopsies of tumors in vehicle-treated mice were collected predose, 4 and 24 hours after dose 1 (D1), and 4 and 24 hours after dose 8 (D8). Lysates were analyzed for (A) full-length MET measured as fmol/μg extracted protein and (B) pY1235-MET expressed as a ratio of full-length MET. Each data point represents an individual xenograft biopsy. The dotted line indicates a 45% decrease in the full-length MET or pY1235-MET:MET ratio from the predose measurement; changes greater than this can be attributed to drug effect.

Determining Biological Variability and Defining Drug-Induced Changes in MET Levels Because clinical PD studies usually compare the PD biomarker in paired biopsies obtained at baseline and after drug administration, it was important to first define the natural longitudinal variability of the molecular targets in the absence of drug treatment to identify what level of change in PD biomarker levels would be required to distinguish drug effect from random sampling variability (the sum total of biological plus technical variability) (12, 13). We attempted to estimate longitudinal variability in growing SNU5 xenografts (FIG. 11A), and we observed a decrease in full-length MET levels/µg extracted protein as tumor size increased from 226 to 2118 mm$^3$ (P<0.05; FIG. 11B) despite relatively constant yield of extracted protein/mg tumor wet weight (data not shown). The fluctuation in full-length MET levels closely tracked with fluctuations in the ratio of human to mouse DNA content (FIG. 11C), suggesting that murine cell infiltration and a resulting increase in murine protein content were contributing to the apparent decline in absolute MET levels as tumors grew larger (14). Normalization of MET levels to human DNA content was partially effective in countering this variability (FIGS. 11D, E). Note also that the variability in the pMET:MET ratios measured from needle biopsies and resected tumor quadrants was similar (FIG. 11F). The variability of full-length MET levels did not affect phosphorylation in SNU5 xenografts, as full-length MET and pY1234/1235-MET levels correlated well (r=0.76, P<0.001, n=64; data not shown). Similar results were observed in vehicle-treated mice bearing GTL-16 xenografts, in which the pMET:MET ratio was stable while the absolute level of full-length MET declined during tumor growth (FIG. 13).

Instead of using longitudinal comparisons of baseline versus on-treatment biopsies, these findings pointed to the need to use intergroup comparisons in preclinical PD studies of the MET receptor (for example, comparison of pMET:MET ratios between drug- and vehicle-treated groups). We applied a calculation of least significant change (LSC) to define the magnitude of change that needed to be reached in order to attribute the change to drug treatment, taking into account total variation (biological and analytical) in the biomarker. The LSC (or critical difference) was calculated using the formula described by Sebastian-Gambaro et al. (15), [$LSC = Z \times \sqrt{CV_i^2 + CV_a^2}$, where $CV_i$ is the variance in vehicle treated group and $CV_a$ is inter-day analytical variation]. The formula was calculated using a one-sided approach as only decreases in pMET were expected after treatment with MET inhibitors (the 1-sided Z values in the above formula are 0.52 [probability, 70%], 1.64 [probability, 95%], and 2.33 [probability, 99%]).

Using validated specimen-handling procedures that preserve pMET species during cold ischemic, we calculated the inter-tumoral variation (equivalent to cross-sectional variation) in vehicle-treated tumors of similar sizes (FIG. 11F) and used it as surrogate for biological variation. The mean inter-tumoral variability of the pY1234/1235-MET:full-length MET ratio was estimated by its within-group coefficient of variance (CV), ranging from 7% to 53% with a mean CV of 20.3% in needle biopsy samples and 18.2% in xenograft quadrants, and biological variability was not dependent on tissue size (FIG. 11F and data not shown).

Therefore the within-tumor variability of MET and pMET levels was determined in four different quadrants of SNU5 tumors (approximately 300 mm$^3$) collected from 4 different vehicle-treated mice (n=16). For full-length MET, the within-tumor variability ranged from 7% to 18% with an average CV of 12%. Adopting a probability of 5% (P<0.05) for a one-sided 95% confidence interval and an analytical variability of 11%, the LSC calculation estimates that changes≥32% in full-length MET are due to treatment rather than biological variability. Average intra-tumoral CV values were 14% for pY1234/1235-MET (range 12% to 19%), 19% for pY1235-MET (range 15% to 25%), and 17% for pY1356-MET (range 8% to 23%). The LSC values based on these pMET intra-tumoral measurements and the corresponding analytical variation of the assays were 43%, 40%, and 44%, respectively (Table 1); therefore, we set a conservative cutoff of 45% when assessing MET or pMET changes to ensure that modulation exceeded the biological and analytical variation in order to conclude that it was due to drug treatment. Note that all measures of sampling variability discussed here are larger than the technical variability indicated by the intra- and inter-assay CVs (Table 1), suggesting that natural biological variation in the tumor content of these analytes is a major contributor to the observed variation.

Relative Levels of pY1234/1235-MET, pY1235-MET, and pY1356-MET in SNU5 Tumors

Figure 13B:
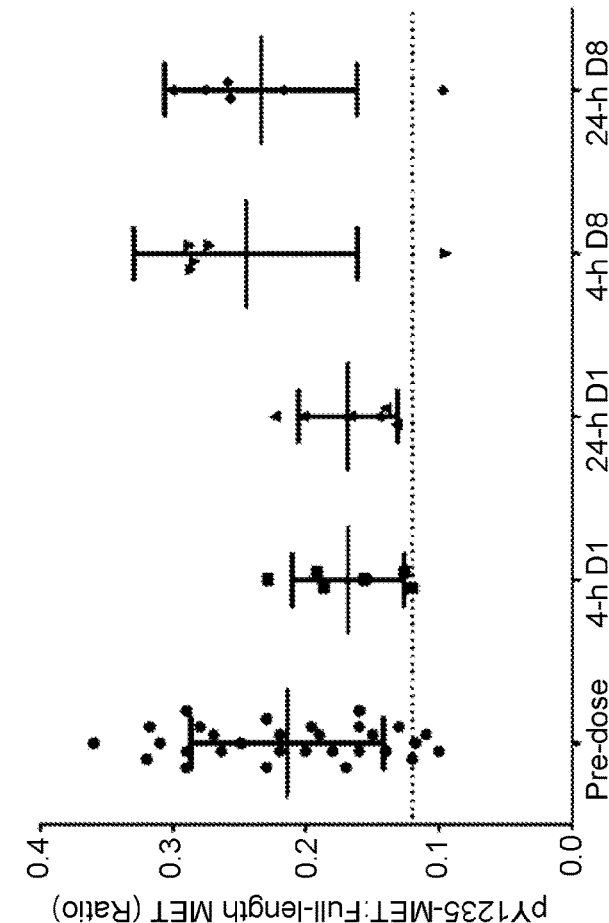

Although several studies have suggested a relationship between phosphorylation of Y1234/1235-MET with A-loop activation and phosphorylation of Y1349/1356-MET with downstream signaling (16), the exact magnitude of phosphorylation at these tyrosines is unknown. We calculated the absolute levels of phosphorylated Y1234/1235-, Y1235-, and Y1356-MET using representative data from SNU5 xenografts treated with PF02341066. In the vehicle-treated group, the ratio of pMET to full-length MET was stable over time: 0.72 for pY1234/1235-MET, 0.21 for pY1235-MET, and 0.19 for pY1356-MET (FIG. 13B). At both doses of PF02341066 (12.5 and 25 mg/kg), both pY1234/1235- and pY1235-MET ratios were decreased. Despite similar baseline phosphorylation of pY1235- and pY1356-MET, suppression of pY1356-MET was significantly less than that of pY1235-MET at 4 hours after treatment with 12.5 or 25 mg/kg PF02341066 (51% versus 95%, respectively; P<0.001) (FIG. 10).

Species Specificity of MET and pMET Antibodies

Figure 14B:
FIG. 14: MET expression determined by immunoblot in fresh flash-frozen mouse liver and muscle tissues. (A) The mouse-specific MET polyclonal antibody AF527 demonstrates the presence of MET in mouse liver and muscle tissues. (B) The polyclonal antibody AF2480 detects both human and mouse pY1234/1235-MET, demonstrating the presence of activated Met protein in mouse liver tissues, while (C) the monoclonal pY1234/p1235-MET antibody (clone D26) used in the MET immunoassay showed minimal cross-reactivity to mouse pY1234/pY1235-MET in Western blots. Cross-reactivity was only observed when mouse MET was loaded at 5-fold the human value, and only very faintly. Immunoblots from A-C were stripped and reanalyzed with Cox-IV antibody (Clone 4D11-B3-E8, Cell Signaling Technologies) for loading control information (details not shown). Mouse tissues are numbered as in Table 3, Residues Y1234, Y1235, and Y1356 are indicated in red. (D) Partial amino acid sequence alignment to demonstrate sequence identity around amino acids surrounding pY1234/1235-MET and pY1356-MET between mouse Met (Swiss Prot P16056) (SEQ ID NO: 17) and human MET (Swiss Prot P08581) (SEQ ID NO: 18), along with a consensus sequence (SEQ ID NO: 19). The underlined amino acid sequences indicate approximate regions used for generating antibodies. Asterisks (*) denote Y residues of interest.
Figure 14A:
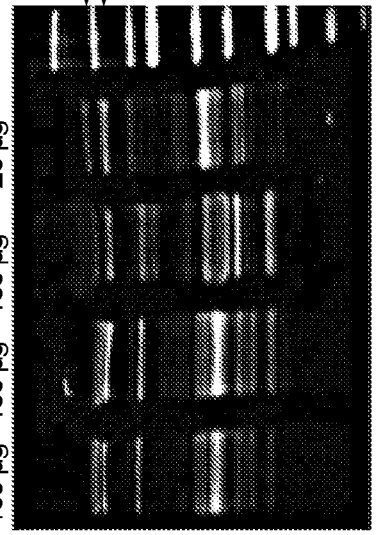
Figure 14C:
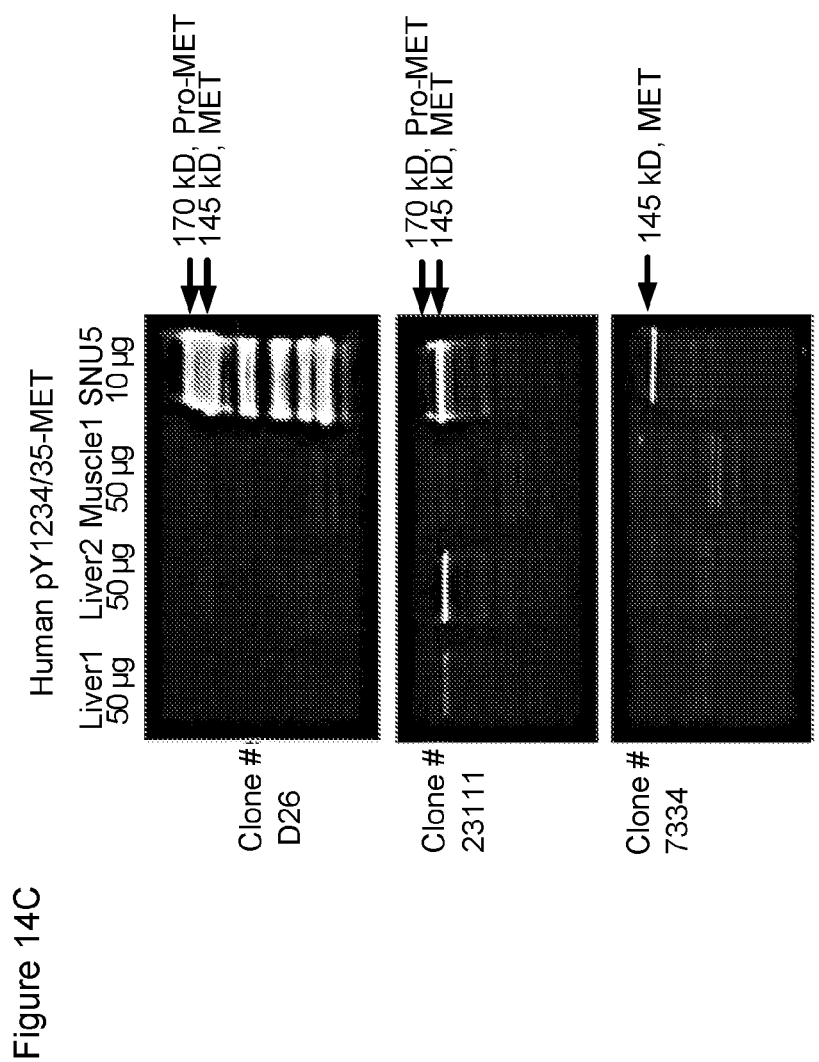

Mouse liver and muscle tissues were probed via Western blot to establish the presence of total mouse MET (N-terminal antibody AF527; R&D Systems) in both tissues, while activated mouse MET (pY1234/pY1235-MET antibody AF2480; R&D Systems) was only observed in liver tissue (FIGS. 14A and B). The human pY1234/pY1235-MET antibody used in the MET immunoassay (clone D26) faintly detected mouse pY1234/pY1235-MET via immunoblot only when 5-fold excess murine protein was used (FIG. 14C). Despite the verified presence of activated murine Met in mouse liver lysates and the high similarity between mouse and human MET sequences surrounding these phosphorylation sites (FIG. 14D), the MET immunoassays described here reported levels of pMET in these mouse samples that were below the assay detection limit for all molecular species except pY1356-MET when applied to the analysis of mouse tissue lysates (Table 3). The pY1356-MET signal was measurable when excess protein was loaded but did not show linear dilution, suggesting matrix interference rather than species cross-reactivity was responsible for the observation. The dominant signal measured in the xenograft studies by the validated immunoassay is entirely due to the human MET analytes.

TABLE 1

Summary of analytical characteristics of full-length MET and pMET assays; data collected from assays run with A549, U87, SNU5 and GTL-16 xenograft tumor extracts.

| Characteristic | Full-length MET | pY1234/1235-MET | pY1235-MET | pY1356-MET |
|---|---|---|---|---|
| Calibrator Curve Range | 0.3-40 pM | 0.3-40 pM | 3.125-200 pM | 3.125-200 pM |
| Inter-assay CV (n) | <11% (5) | <13% (5) | <7% (5) | <14% (6) |
| Intra-assay CV (n) | <7% (22) | <5% (20) | <10% (21) | <10% (12) |
| Dilution Recovery (mean ± SD) | 99% ± 12% | 105% ± 5% | 103% ± 12% | 99% ± 11% |
| Spike Recovery (mean ± SD) | 98% ± 18% | 84% ± 6% | 88% ± 5% | 86% ± 29% |
| Intra-tumor Biological Variability (LSC, mean ± SD)[a] | 32% ± 8.1% | 43% ± 5.3% | 40% ± 7.5% | 44% ± 9.6% |

[a]LSC calculated from four tumor quarters to describe biological variability within the tumor.
$LSC = Z \times \sqrt{CV_i^2 + CV_a^2}$, where $CV_i$ is the variance in vehicle-treated group and $CV_a$ is inter-day analytical variation
CV = coefficient of variation

TABLE 2

Measurement of MET and pMET levels in core needle specimens (#1-5) of a resected human HPRC tumor harboring a germ line mutation in MET (H1112R)

| Specimen | Time Before Freezing | Full-length MET | pY1235-MET | pY1234/1235-MET | Percent pMET |
|---|---|---|---|---|---|
| 1 | <2 min | 0.097 | <LLQ | <LLQ | NA |
| 2 | <2 min | 0.368 | <LLQ | 0.041 | 11.1% |
| 3 | 1 mm | 0.267 | <LLQ | 0.037 | 13.9% |
| 4[a] | <1 min | 0.073 | <LLQ | <LLQ | NA |
| 5 | 1 min | 0.109 | <LLQ | <LLQ | NA |

[a]Tumor tissue was necrotic.
LLQ = lower limit of quantification (0.625 fmol/μg protein for pY1235-MET and 0.08 fmol/μg protein for pY1234/1235-MET)
NA = not applicable

TABLE 3

Measurement of mouse MET and pMET species by the MET immunoassays

| Tissue | Protein Load (μg/mL) | Intact MET (fmol/μg protein) | pY1234/1235-MET (fmol/μg protein) | pY1235-MET (fmol/μg protein) | pY1356-MET (fmol/μg protein) |
|---|---|---|---|---|---|
| SNU5 Xenograft (positive control) | 4 | 5.7 | 5.0 | 3.8 | 4.3 |
| Mouse Liver-1 | 100 | <DL | <DL | <DL | 0.0672 |
|  | 200 | <DL | <DL | <DL | 0.0159 |
| Mouse Liver-2 | 100 | <DL | <DL | <DL | 0.0503 |
|  | 200 | <DL | <DL | <DL | <DL |
| Mouse Muscle-1 | 100 | <DL | <DL | <DL | <DL |
|  | 200 | <DL | <DL | <DL | <DL |
| Mouse Muscle-2 | 100 | <DL | <DL | <DL | <DL |
|  | 200 | <DL | <DL | <DL | <DL |

DL = assay detection limit (lower bound)

SUPPLEMENTARY REFERENCES

1. Ferracini R, Longati P, Naldini L, Vigna E, Comoglio P M. Identification of the major autophosphorylation site of the Met/hepatocyte growth factor receptor tyrosine kinase. J Biol Chem 1991; 266:19558-64.
2. Longati P, Bardelli A, Ponzetto C, Naldini L, Comoglio P M. Tyrosines 1234-1235 are critical for activation of the tyrosine kinase encoded by the MET proto-oncogene (HGF receptor). Oncogene 1994; 9:49-57.
3. Chiara F, Michieli P, Pugliese L, Comoglio P M. Mutations in the met oncogene unveil a "dual switch" mechanism controlling tyrosine kinase activity. J Biol Chem 2003; 278:29352-8.
4. Cristiani C, Rusconi L, Perego R, Schiering N, Kalisz H M, Knapp S, et al. Regulation of the wild-type and Y1235D mutant Met kinase activation. Biochemistry 2005; 44:14110-9.
5. Ponzetto C, Bardelli A, Zhen Z, Maina F, dalla Zonca P, Giordano S, et al. A multifunctional docking site mediates signaling and transformation by the hepatocyte growth factor/scatter factor receptor family. Cell 1994; 77:261-71.
6. Ponzetto C, Zhen Z, Audero E, Maina F, Bardelli A, Basile M L, et al. Specific uncoupling of GRB2 from the Met receptor. Differential effects on transformation and motility. J Biol Chem 1996; 271:14119-23.
7. Zhu H, Naujokas M A, Fixman E D, Torossian K, Park M. Tyrosine 1356 in the carboxyl-terminal tail of the HGF/SF receptor is essential for the transduction of signals for cell motility and morphogenesis. J Biol Chem 1994; 269:29943-8.
8. Nettleship J E, Flanagan A, Rahman-Huq N, Hamer R, Owens R J. Converting monoclonal antibodies into Fab fragments for transient expression in mammalian cells. Methods Mol Biol 2012; 801:137-59.
9. Panayotou G. Surface plasmon resonance. Measuring protein interactions in real time. Methods Mol Biol 1998; 88:1-10.
10. Pfister T D, Hollingshead M, Kinders R J, Zhang Y, Evrard Y A, Ji J, et al. Development and validation of an immunoassay for quantification of topoisomerase I in solid tumor tissues. PLoS One 2012; 7:e50494.
11. Kinders R J, Hollingshead M, Lawrence S, Ji J, Tabb B, Bonner W M, et al. Development of a validated immunofluorescence assay for gammaH2AX as a pharmacodynamic marker of topoisomerase I inhibitor activity. Clin Cancer Res 2010; 16:5447-57.
12. Smellie W S. What is a significant difference between sequential laboratory results? J Clin Pathol 2008; 61:419-25.
13. Christensen J G, Burrows J, Salgia R. c-Met as a target for human cancer and characterization of inhibitors for therapeutic intervention. Cancer Letters 2005; 225:1-26.
14. Alcoser S Y, Kimmel D J, Borgel S D, Carter J P, Dougherty K M, Hollingshead M G. Real-time PCR-based assay to quantify the relative amount of human and mouse tissue present in tumor xenografts. BMC Biotechnol 2011; 11:124.
15. Sebastian-Gambaro M A, Liron-Hernandez F J, Fuentes-Arderiu X. Intra- and inter-individual biological variability data bank. Eur J Clin Chem Clin Biochem 1997; 35:845-52.
16. Trusolino L, Bertotti A, Comoglio P M. MET signalling: principles and functions in development, organ regeneration and cancer. Nat Rev Mol Cell Biol 2010; 11:834-48.

It is understood that the examples and embodiments described herein are for illustrative purposes only and that various modifications or changes in light thereof will be suggested to persons skilled in the art and are to be included within the spirit and purview of this application and scope of the appended claims.

```
SEQUENCES
antibody #23111 Heavy chain variable region:
CDR1, CDR2, CDR3 underlined
                                        SEQ ID NO: 1
         10         20         30         40
QSVEESGGRL VTPGTPLTLT CTVSGFSLSN YAMGWFRQAP 50         60         70         80
GKGLEWIGII SRSGALWYAN WANGRFTISK TSTTVDLKIT 90        100        110        120
SPTPEDTATY FCARTNYYDG YGGVDAVLTR FDFWGQGTLV

130
TVSSG antibody #23111 Light chain variable region:
CDR1, CDR2, CDR3 underlined
                                        SEQ ID NO: 2
         10         20         30         40
ADVVMTQTPS SVEAAVGGTV TIKCQASQSI GGGLSWYQQK 50         60         70         80
AGQPPKLLIY GASTLESGVP SRFKGSGSGT EFTLTISDLE 90        100        110        120
CADAATYYCQ SNYGSDIRDY GHTFGGGTEV VVKGDPVAPT

130
VLIFPP antibody #23111 CDRH1
                                        SEQ ID NO: 3
GFSLSN YAMG antibody #23111 CDRH2
                                        SEQ ID NO: 4
II SRSGALWYAN WANG antibody #23111 CDRH3
                                        SEQ ID NO: 5
FCARTNYYDG YGGVDAVLTR FDF antibody #23111 CDRL1
                                        SEQ ID NO: 6
QASQSI GGGLS antibody #23111 CDRL2
                                        SEQ ID NO: 7
GASTLES antibody #23111 CDRL3
                                        SEQ ID NO: 8
Q SNYGSDIRDY GHT a nucleic acid sequence encoding antibody
23111 heavy chain variable region
                                        SEQ ID NO: 9
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCACGCCTGGGA

CACCCCTGACACTCACCTGCACAGTCTCTGGATTCTCCCTCAGTAACTAT

GCAATGGGCTGGTTCCGCCAGGCTCCAGGGAAGGGGCTGGAATGGATCGG

CATCATTAGTCGTAGTGGTGCGCTCTGGTACGCGAACTGGGCGAATGGTC

GATTCACCATCTCCAAAACCTCGACCACGGTGGATCTGAAAATCACCAGT

CCGACACCCGAGGACACGGCCACCTATTTCTGTGCCAGAACAAACTATTA

TGATGGTTATGGTGGTGTTGATGCGGTGTTAACTCGGTTCGATTTCTGGG

GCCAGGGCACCCTGGTCACCGTCTCCTCAGGGCAACCTAAGGCTCCATCA
```

```
GTCTTCCCACTGGCCCCCTGCTGCGGGACACACCCAGCTCCACGGTGAC

CCTGGGCTGCCTGGTCAAAGGGTACCTCCCGGAGCCAGTGACCGTGACCT

GGAACTCGGGCACCCTCACCAATGGGGTACGCACCTTCCCGTCCGTCCGG

CAGTCCTCAGGCCTCTACTCGCTGAGCAGCGTGGTGAGCGTGACCTCAAG

CAGCCAGCCCGTCACCTGCAACGTGGCCCACCCAGCCACCAACACCAAAG

TGGACAAGACCGTTGCGCCCTCGACATGCAGCAAGCCCACGTGCCCACCC

CCTGAACTCCTGGGGGGACCGTCTGTCTTCATCTTCCCCCCAAAACCCAA

GGACACCCTCATGATCTCACGCACCCCCGAGGTCACATGCGTGGTGGTGG

ACGTGAGCCAGGATGACCCCGAGGTGCAGTTCACATGGTACATAAACAAC

GAGCAGGTGCGCACCGCCCGGCCGCCGCTACGGGAGCAGCAGTTCAACAG

CACGATCCGCGTGGTCAGCACCCTCCCCATCGCGCACCAGGACTGGCTGA

GGGGCAAGGAGTTCAAGTGCAAAGTCCACAACAAGGCACTCCCGGCCCCC

ATCGAGAAAACCATCTCCAAAGCCAGAGGGCAGCCCCTGGAGCCGAAGGT

CTACACCATGGGCCCTCCCCGGGAGGAGCTGAGCAGCAGGTCGGTCAGCC

TGACCTGCATGATCAACGGCTTCTACCCTTCCGACATCTCGGTGGAGTGG

GAGAAGAACGGGAAGGCAGAGGACAACTACAAGACCACGCCGGCCGTGCT

GGACAGCGACGGCTCCTACTTCCTCTACAGCAAGCTCTCAGTGCCCACGA

GTGAGTGGCAGCGGGGCGACGTCTTCACCTGCTCCGTGATGCACGAGGCC

TTGCACAACCACTACACGCAGAAGTCCATCTCCCGCTCTCCGGGTAAATA
A a nucleic acid sequence encoding antibody
23111 light chain variable region
                                    SEQ ID NO: 10
ATGGACACGAGGGCCCCCACTCAGCTGCTGGGGCTCCTGCTGCTCTGGCT

CCCAGGTGCCAGATGTGCCGACGTCGTGATGACCCAGACTCCATCCTCCG

TGGAGGCAGCTGTGGGAGGCACAGTCACCATCAAATGCCAGGCCAGTCAG

AGCATTGGTGGTGGCTTATCCTGGTATCAGCAGAAAGCAGGGCAGCCTCC

CAAGCTCCTGATCTATGGTGCATCCACTCTGGAATCTGGGGTCCCATCGC

GGTTTAAGGGCAGTGGATCTGGGACAGAATTCACTCTCACCATCAGCGAC

CTGGAGTGTGCCGATGCTGCCACTTATTATTGTCAAAGTAATTATGGTAG

TGATATTCGTGATTATGGGCATACTTTCGGCGGAGGGACCGAGGTGGTGG

TCAAAGGTGATCCAGTTGCACCTACTGTCCTCATCTTCCCACCAGCTGCT

GATCAGGTGGCAACTGGAACAGTCACCATCGTGTGTGTGGCAATAAATA

CTTTCCCGATGTCACCGTCACCTGGGAGGTGGATGGCACCACCCAAACAA

CTGGCATCGAGAACAGTAAAACACCGCAGAATTCTGCAGATTGTACCTAC

AACCTCAGTAGCACTCTGACACTGACCAGCACACAGTACAACAGCCACAA

AGAGTACACCTGCAAGGTGACCCAGGGCACGACCTCAGTCGTCCAGAGCT

TCAATAGGGGTGACTGTTAA antibody #23111 Heavy chain
                                    SEQ ID NO: 11
QSVEESGGRLVTPGTPLTLTCTVSGFSLSNYAMGWFRQAPGKGLEWIGII

SRSGALWYANWANGRFTISKTSTTVDLKITSPTPEDTATYFCARTNYYDG

YGGVDAVLTRFDFWGQGTLVTVSSGQPKAPSVFPLAPCCGDTPSSTVTLG

CLVKGYLPEPVTVTWNSGTLTNGVRTFPSVRQSSGLYSLSSVVSVTSSSQ

PVTCNVAHPATNTKVDKTVAPSTCSKPTCPPPELLGGPSVFIFPPKPKDT

LMISRTPEVTCVVVDVSQDDPEVQFTWYINNEQVRTARPPLREQQFNSTI

RVVSTLPIAHQDWLRGKEFKCKVHNKALPAPIEKTISKARGQPLEPKVYT

MGPPREELSSRSVSLTCMINGFYPSDISVEWEKNGKAEDNYKTTPAVLDS

DGSYFLYSKLSVPTSEWQRGDVFTCSVMHEALHNHYTQKSISRSPGK antibody #23111 Light chain
                                    SEQ ID NO: 12
ADVVMTQTPSSVEAAVGGTVTIKCQASQSIGGGLSWYQQKAGQPPKLLIY

GASTLESGVPSRFKGSGSGTEFTLTISDLECADAATYYCQSNYGSDIRDY

GHTFGGGTEVVVKGDPVAPTVLIFPPAADQVATGTVTIVCVANKYFPDVT

VTWEVDGTTQTTGIENSKTPQNSADCTYNLSSTLTLTSTQYNSHKEYTCK

VTQGTTSVVQSFNRGDC
```

What is claimed is:

1. An antibody that specifically binds to pY1235-MET, or a fragment thereof that contains pY1235, wherein the antibody comprises a heavy chain variable region and a light chain variable region, wherein the heavy chain variable region and the light chain variable region each comprise the following three complementary determining regions (CDRs): CDR1, CDR2 and CDR3; wherein:
i) the CDR1 of the heavy chain variable region comprises the amino acid sequence of SEQ ID NO:3;
ii) the CDR2 of the heavy chain variable region comprises the amino acid sequence of SEQ ID NO:4;
iii) the CDR3 of the heavy chain variable region comprises an amino acid sequence of SEQ ID NO:5;
iv) the CDR1 of the light chain variable region comprises the amino acid sequence of SEQ ID NO:6;
v) the CDR2 of the light chain variable region comprises the amino acid sequence of SEQ ID NO:7;
vi) the CDR3 of the light chain variable region comprises the amino acid sequence of SEQ ID NO:8.

2. The antibody of claim 1, wherein the antibody comprises a heavy chain variable segment having at least 95% sequence identity to SEQ ID NO:1.

3. The antibody of claim 1, wherein the antibody comprises a light chain variable segment having at least 95% sequence identity to SEQ ID NO:2.

4. A polynucleotide encoding the antibody of claim 1.

5. An expression cassette comprising the polynucleotide of claim 4 operably linked to a promoter.

6. The expression cassette of claim 5, wherein the promoter is heterologous to the polynucleotide.

7. A host cell comprising the expression cassette of claim 5.

8. A method of making an antibody that specifically binds to pY1235-MET, or a fragment thereof that contains pY1235, comprising culturing the host cell of claim 7 and purifying the antibody from spent culture media or cultured host cell lysate.

9. A method of specifically detecting a target antigen, wherein the target antigen comprises pY1235-MET, or a fragment thereof that contains pY1235, in a sample comprising:

contacting the sample with an antibody of claim 1, thereby forming an antibody:target antigen immunoconjugate, if present; and detecting the presence or absence of the immunoconjugate.

10. A method for identifying a test compound as an inhibitor of MET, the method comprising:

contacting a cell or extract thereof with the test compound;

specifically detecting pY1235-MET, or a fragment thereof containing pY1235, in the cell or extract using the method of claim 9; and identifying the test compound as an inhibitor of MET if:
pY1235-MET, or the fragment thereof containing pY1235, or
a ratio of pY1235-MET, or the fragment thereof, to total MET, is reduced relative to a control cell or extract that has not been contacted with the test compound.

11. The method of claim 10, wherein the method further comprises identifying the test compound as an inhibitor of MET if full length MET or a ratio of full length MET to total MET is reduced relative to a control cell or extract that has not been contacted with the test compound.

12. A method of monitoring a MET inhibitor treatment of a subject in need thereof, the method comprising:

administering a first dose of the MET inhibitor treatment to the subject providing a first sample from the subject;

specifically detecting pY1235-MET, or fragments thereof containing pY1235, in the first sample or a portion thereof using the method of claim 9;

administering a second dose of the MET inhibitor treatment to the subject;

providing a second sample from the subject; and specifically detecting pY1235-MET, or fragments thereof containing pY1235, in the second sample or a portion thereof using the method of claim 9.

* * * * *

SEQUENCE LISTING

<160> NUMBER OF SEQ ID NOS: 19

<210> SEQ ID NO 1
<211> LENGTH: 125
<212> TYPE: PRT
<213> ORGANISM: Artificial sequence
<220> FEATURE:
<223> OTHER INFORMATION: Synthetic construct

<400> SEQUENCE: 1

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Ala
            20                  25                  30

Met Gly Trp Phe Arg Gln Ala Pro Gly Lys Gly Leu Glu Trp Ile Gly
        35                  40                  45

Ile Ile Ser Arg Ser Gly Ala Leu Trp Tyr Ala Asn Trp Ala Asn Gly
    50                  55                  60

Arg Phe Thr Ile Ser Lys Thr Ser Thr Thr Val Asp Leu Lys Ile Thr
65                  70                  75                  80

Ser Pro Thr Pro Glu Asp Thr Ala Thr Tyr Phe Cys Ala Arg Thr Asn
            85                  90                  95

Tyr Tyr Asp Gly Tyr Gly Gly Val Asp Ala Val Leu Thr Arg Phe Asp
            100                 105                 110

Phe Trp Gly Gln Gly Thr Leu Val Thr Val Ser Ser Gly
        115                 120                 125

<210> SEQ ID NO 2
<211> LENGTH: 126
<212> TYPE: PRT
<213> ORGANISM: Artificial sequence
<220> FEATURE:
<223> OTHER INFORMATION: Synthetic construct

<400> SEQUENCE: 2

Ala Asp Val Val Met Thr Gln Thr Pro Ser Ser Val Glu Ala Ala Val
1               5                   10                  15

Gly Gly Thr Val Thr Ile Lys Cys Gln Ala Ser Gln Ser Ile Gly Gly
            20                  25                  30

Gly Leu Ser Trp Tyr Gln Gln Lys Ala Gly Gln Pro Pro Lys Leu Leu
        35                  40                  45

Ile Tyr Gly Ala Ser Thr Leu Glu Ser Gly Val Pro Ser Arg Phe Lys
50                  55                  60

Gly Ser Gly Ser Gly Thr Glu Phe Thr Leu Thr Ile Ser Asp Leu Glu
65                  70                  75                  80

Cys Ala Asp Ala Ala Thr Tyr Tyr Cys Gln Ser Asn Tyr Gly Ser Asp
            85                  90                  95

Ile Arg Asp Tyr Gly His Thr Phe Gly Gly Gly Thr Glu Val Val Val
            100                 105                 110

Lys Gly Asp Pro Val Ala Pro Thr Val Leu Ile Phe Pro Pro
        115                 120                 125

<210> SEQ ID NO 3
<211> LENGTH: 10
<212> TYPE: PRT
<213> ORGANISM: Artificial sequence
<220> FEATURE:
<223> OTHER INFORMATION: Synthetic construct

<400> SEQUENCE: 3

Gly Phe Ser Leu Ser Asn Tyr Ala Met Gly
1               5                   10

<210> SEQ ID NO 4
<211> LENGTH: 16
<212> TYPE: PRT
<213> ORGANISM: Artificial sequence
<220> FEATURE:
<223> OTHER INFORMATION: Synthetic construct

<400> SEQUENCE: 4

Ile Ile Ser Arg Ser Gly Ala Leu Trp Tyr Ala Asn Trp Ala Asn Gly
1               5                   10                  15

<210> SEQ ID NO 5
<211> LENGTH: 23
<212> TYPE: PRT
<213> ORGANISM: Artificial sequence
<220> FEATURE:

<223> OTHER INFORMATION: Synthetic construct

<400> SEQUENCE: 5

Phe Cys Ala Arg Thr Asn Tyr Tyr Asp Gly Tyr Gly Gly Val Asp Ala
1               5                   10                  15
Val Leu Thr Arg Phe Asp Phe
            20

<210> SEQ ID NO 6
<211> LENGTH: 11
<212> TYPE: PRT
<213> ORGANISM: Artificial sequence
<220> FEATURE:
<223> OTHER INFORMATION: Synthetic construct

<400> SEQUENCE: 6

Gln Ala Ser Gln Ser Ile Gly Gly Gly Leu Ser
1               5                   10

<210> SEQ ID NO 7
<211> LENGTH: 7
<212> TYPE: PRT
<213> ORGANISM: Artificial sequence
<220> FEATURE:
<223> OTHER INFORMATION: Synthetic construct

<400> SEQUENCE: 7

Gly Ala Ser Thr Leu Glu Ser
1               5

<210> SEQ ID NO 8
<211> LENGTH: 14
<212> TYPE: PRT
<213> ORGANISM: Artificial sequence
<220> FEATURE:
<223> OTHER INFORMATION: Synthetic construct

<400> SEQUENCE: 8

Gln Ser Asn Tyr Gly Ser Asp Ile Arg Asp Tyr Gly His Thr
1               5                   10

<210> SEQ ID NO 9
<211> LENGTH: 1401
<212> TYPE: DNA
<213> ORGANISM: Artificial sequence
<220> FEATURE:
<223> OTHER INFORMATION: Synthetic construct

<400> SEQUENCE: 9

```
atggagactg ggctgcgctg gcttctcctg gtcgctgtgc tcaaaggtgt ccagtgtcag     60
tcggtggagg agtccggggg tcgcctggtc acgcctggga caccctgac actcacctgc    120 acagtctctg gattctccct cagtaactat gcaatgggct ggttccgcca ggctccaggg    180
aaggggctgg aatggatcgg catcattagt cgtagtggtg cgctctggta cgcgaactgg    240
gcgaatggtc gattcaccat ctccaaaacc tcgaccacgg tggatctgaa aatcaccagt    300
ccgacacccg aggacacggc cacctatttc tgtgccagaa caaactatta tgatggttat    360
ggtggtgttg atgcggtgtt aactcggttc gatttctggg gccagggcac cctggtcacc    420
gtctcctcag gcaacctaa ggctccatca gtcttccac tggcccctg ctgcggggac    480 acacccagct ccacggtgac cctgggctgc ctggtcaaag gtacctccc ggagccagtg    540 accgtgacct ggaactcggg caccctcacc aatggggtac gcaccttccc gtccgtccgg    600
```

```
cagtcctcag gcctctactc gctgagcagc gtggtgagcg tgacctcaag cagccagccc      660
gtcacctgca acgtggccca cccagccacc aacaccaaag tggacaagac cgttgcgccc      720
tcgacatgca gcaagcccac gtgccacccc cctgaactcc tgggggggacc gtctgtcttc     780 atcttccccc caaacccaag gacacccctc atgatctcac gcaccccgca ggtcacatgc      840
gtggtggtgg acgtgagcca ggatgacccc gaggtgcagt tcacatggta cataaacaac      900
gagcaggtgc gcaccgcccg ccgccgccta cgggagcagc agttcaacag cacgatccgc      960
gtggtcagca ccctccccat cgcgcaccag gactggctga ggggcaagga gttcaagtgc     1020
aaagtccaca acaaggcact cccggccccc atcgagaaaa ccatctccaa agccagaggg     1080
cagcccctgg agccgaaggt ctacaccatg ggccctcccc gggaggagct gagcagcagg     1140
tcggtcagcc tgacctgcat gatcaacggc ttctaccctt ccgacatctc ggtggagtgg     1200
gagaagaacg ggaaggcaga ggacaactac aagaccacgc cggccgtgct ggacagcgac     1260
ggctcctact cctctacag caagctctca gtgcccacga gtgagtggca gcggggcgac      1320
gtcttcacct gctccgtgat gcacgaggcc ttgcacaacc actacacgca gaagtccatc     1380
tcccgctctc cgggtaaata a                                               1401
```

<210> SEQ ID NO 10
<211> LENGTH: 720
<212> TYPE: DNA
<213> ORGANISM: Artificial sequence
<220> FEATURE:
<223> OTHER INFORMATION: Synthetic construct

<400> SEQUENCE: 10

```
atggacacga gggcccccac tcagctgctg ggctcctgc tgctctggct cccaggtgcc       60
agatgtgccg acgtcgtgat gacccagact ccatcctccg tggaggcagc tgtgggaggc     120
acagtcacca tcaaatgcca ggccagtcag agcattggtg gtggcttatc ctggtatcag     180
cagaaagcag ggcagcctcc caagctcctg atctatggtg catccactct ggaatctggg     240
gtcccatcgc ggtttaaggg cagtggatct gggacagaat tcactctcac catcagcgac     300
ctggagtgtg ccgatgctgc cacttattat tgtcaaagta attatggtag tgatattcgt     360
gattatgggc atactttcgg cggagggacc gaggtggtgg tcaaaggtga tccagttgca     420
cctactgtcc tcatcttccc accagctgct gatcaggtgg caactggaac agtcaccatc     480
gtgtgtgtgg cgaataaata cttcccgat gtcaccgtca cctgggaggt ggatggcacc      540
acccaaacaa ctggcatcga gaacagtaaa acaccgcaga attctgcaga ttgtacctac     600
aacctcagta gcactctgac actgaccagc acacagtaca cagccacaa agagtacacc      660 tgcaaggtga cccagggcac gacctcagtc gtccagagct tcaataggg tgactgttaa      720
```

<210> SEQ ID NO 11
<211> LENGTH: 447
<212> TYPE: PRT
<213> ORGANISM: Artificial sequence
<220> FEATURE:
<223> OTHER INFORMATION: Synthetic construct

<400> SEQUENCE: 11

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Ala
            20                  25                  30

Met Gly Trp Phe Arg Gln Ala Pro Gly Lys Gly Leu Glu Trp Ile Gly
```

```
                35                  40                  45
Ile Ile Ser Arg Ser Gly Ala Leu Trp Tyr Ala Asn Trp Ala Asn Gly
 50                  55                  60

Arg Phe Thr Ile Ser Lys Thr Ser Thr Thr Val Asp Leu Lys Ile Thr
 65                  70                  75                  80

Ser Pro Thr Pro Glu Asp Thr Ala Thr Tyr Phe Cys Ala Arg Thr Asn
                 85                  90                  95

Tyr Tyr Asp Gly Tyr Gly Gly Val Asp Ala Val Leu Thr Arg Phe Asp
                100                 105                 110

Phe Trp Gly Gln Gly Thr Leu Val Thr Val Ser Ser Gly Gln Pro Lys
            115                 120                 125

Ala Pro Ser Val Phe Pro Leu Ala Pro Cys Cys Gly Asp Thr Pro Ser
130                 135                 140

Ser Thr Val Thr Leu Gly Cys Leu Val Lys Gly Tyr Leu Pro Glu Pro
145                 150                 155                 160

Val Thr Val Thr Trp Asn Ser Gly Thr Leu Thr Asn Gly Val Arg Thr
                165                 170                 175

Phe Pro Ser Val Arg Gln Ser Ser Gly Leu Tyr Ser Leu Ser Ser Val
                180                 185                 190

Val Ser Val Thr Ser Ser Ser Gln Pro Val Thr Cys Asn Val Ala His
            195                 200                 205

Pro Ala Thr Asn Thr Lys Val Asp Lys Thr Val Ala Pro Ser Thr Cys
210                 215                 220

Ser Lys Pro Thr Cys Pro Pro Glu Leu Leu Gly Gly Pro Ser Val
225                 230                 235                 240

Phe Ile Phe Pro Pro Lys Pro Lys Asp Thr Leu Met Ile Ser Arg Thr
                245                 250                 255

Pro Glu Val Thr Cys Val Val Val Asp Val Ser Gln Asp Asp Pro Glu
                260                 265                 270

Val Gln Phe Thr Trp Tyr Ile Asn Asn Glu Gln Val Arg Thr Ala Arg
            275                 280                 285

Pro Pro Leu Arg Glu Gln Gln Phe Asn Ser Thr Ile Arg Val Val Ser
290                 295                 300

Thr Leu Pro Ile Ala His Gln Asp Trp Leu Arg Gly Lys Glu Phe Lys
305                 310                 315                 320

Cys Lys Val His Asn Lys Ala Leu Pro Ala Pro Ile Glu Lys Thr Ile
                325                 330                 335

Ser Lys Ala Arg Gly Gln Pro Leu Glu Pro Lys Val Tyr Thr Met Gly
            340                 345                 350

Pro Pro Arg Glu Glu Leu Ser Ser Arg Ser Val Ser Leu Thr Cys Met
            355                 360                 365

Ile Asn Gly Phe Tyr Pro Ser Asp Ile Ser Val Glu Trp Glu Lys Asn
370                 375                 380

Gly Lys Ala Glu Asp Asn Tyr Lys Thr Thr Pro Ala Val Leu Asp Ser
385                 390                 395                 400

Asp Gly Ser Tyr Phe Leu Tyr Ser Lys Leu Ser Val Pro Thr Ser Glu
                405                 410                 415

Trp Gln Arg Gly Asp Val Phe Thr Cys Ser Val Met His Glu Ala Leu
            420                 425                 430

His Asn His Tyr Thr Gln Lys Ser Ile Ser Arg Ser Pro Gly Lys
            435                 440                 445

<210> SEQ ID NO 12
```

<211> LENGTH: 217
<212> TYPE: PRT
<213> ORGANISM: Artificial sequence
<220> FEATURE:
<223> OTHER INFORMATION: Synthetic construct

<400> SEQUENCE: 12

Ala Asp Val Val Met Thr Gln Thr Pro Ser Ser Val Glu Ala Ala Val
1               5                   10                  15
Gly Gly Thr Val Thr Ile Lys Cys Gln Ala Ser Gln Ser Ile Gly Gly
            20                  25                  30
Gly Leu Ser Trp Tyr Gln Gln Lys Ala Gly Gln Pro Pro Lys Leu Leu
        35                  40                  45
Ile Tyr Gly Ala Ser Thr Leu Glu Ser Gly Val Pro Ser Arg Phe Lys
    50                  55                  60
Gly Ser Gly Ser Gly Thr Glu Phe Thr Leu Thr Ile Ser Asp Leu Glu
65                  70                  75                  80
Cys Ala Asp Ala Ala Thr Tyr Tyr Cys Gln Ser Asn Tyr Gly Ser Asp
                85                  90                  95
Ile Arg Asp Tyr Gly His Thr Phe Gly Gly Gly Thr Glu Val Val Val
            100                 105                 110
Lys Gly Asp Pro Val Ala Pro Thr Val Leu Ile Phe Pro Pro Ala Ala
        115                 120                 125
Asp Gln Val Ala Thr Gly Thr Val Thr Ile Val Cys Val Ala Asn Lys
    130                 135                 140
Tyr Phe Pro Asp Val Thr Val Thr Trp Glu Val Asp Gly Thr Thr Gln
145                 150                 155                 160
Thr Thr Gly Ile Glu Asn Ser Lys Thr Pro Gln Asn Ser Ala Asp Cys
                165                 170                 175
Thr Tyr Asn Leu Ser Ser Thr Leu Thr Leu Thr Ser Thr Gln Tyr Asn
            180                 185                 190
Ser His Lys Glu Tyr Thr Cys Lys Val Thr Gln Gly Thr Thr Ser Val
        195                 200                 205
Val Gln Ser Phe Asn Arg Gly Asp Cys
    210                 215

<210> SEQ ID NO 13
<211> LENGTH: 1390
<212> TYPE: PRT
<213> ORGANISM: Artificial sequence
<220> FEATURE:
<223> OTHER INFORMATION: Synthetic construct

<400> SEQUENCE: 13

Met Lys Ala Pro Ala Val Leu Ala Pro Gly Ile Leu Val Leu Leu Phe
1               5                   10                  15
Thr Leu Val Gln Arg Ser Asn Gly Glu Cys Lys Glu Ala Leu Ala Lys
            20                  25                  30
Ser Glu Met Asn Val Asn Met Lys Tyr Gln Leu Pro Asn Phe Thr Ala
        35                  40                  45
Glu Thr Pro Ile Gln Asn Val Ile Leu His Glu His His Ile Phe Leu
    50                  55                  60
Gly Ala Thr Asn Tyr Ile Tyr Val Leu Asn Glu Glu Asp Leu Gln Lys
65                  70                  75                  80
Val Ala Glu Tyr Lys Thr Gly Pro Val Leu Glu His Pro Asp Cys Phe
                85                  90                  95
Pro Cys Gln Asp Cys Ser Ser Lys Ala Asn Leu Ser Gly Gly Val Trp

-continued

```
            100                 105                 110
Lys Asp Asn Ile Asn Met Ala Leu Val Val Asp Thr Tyr Tyr Asp Asp
            115                 120                 125

Gln Leu Ile Ser Cys Gly Ser Val Asn Arg Gly Thr Cys Gln Arg His
            130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
                180                 185                 190

Ile Asn Phe Phe Val Gly Asn Thr Ile Asn Ser Ser Tyr Phe Pro Asp
                195                 200                 205

His Pro Leu His Ser Ile Ser Val Arg Arg Leu Lys Glu Thr Lys Asp
                210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
                260                 265                 270

Thr Phe His Thr Arg Ile Ile Arg Phe Cys Ser Ile Asn Ser Gly Leu
                275                 280                 285

His Ser Tyr Met Glu Met Pro Leu Glu Cys Ile Leu Thr Glu Lys Arg
                290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
                340                 345                 350

Ser Ala Glu Pro Met Asp Arg Ser Ala Met Cys Ala Phe Pro Ile Lys
                355                 360                 365

Tyr Val Asn Asp Phe Phe Asn Lys Ile Val Asn Lys Asn Asn Val Arg
                370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
                420                 425                 430

Gln Phe Ser Glu Val Leu Leu Thr Ser Ile Ser Thr Phe Ile Lys Gly
                435                 440                 445

Asp Leu Thr Ile Ala Asn Leu Gly Thr Ser Glu Gly Arg Phe Met Gln
                450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
                500                 505                 510

Ile Pro Leu Asn Gly Leu Gly Cys Arg His Phe Gln Ser Cys Ser Gln
                515                 520                 525
```

```
Cys Leu Ser Ala Pro Pro Phe Val Gln Cys Gly Trp Cys His Asp Lys
    530                 535                 540
Cys Val Arg Ser Glu Glu Cys Leu Ser Gly Thr Trp Thr Gln Gln Ile
545                 550                 555                 560
Cys Leu Pro Ala Ile Tyr Lys Val Phe Pro Asn Ser Ala Pro Leu Glu
                565                 570                 575
Gly Gly Thr Arg Leu Thr Ile Cys Gly Trp Asp Phe Gly Phe Arg Arg
                580                 585                 590
Asn Asn Lys Phe Asp Leu Lys Lys Thr Arg Val Leu Leu Gly Asn Glu
                595                 600                 605
Ser Cys Thr Leu Thr Leu Ser Glu Ser Thr Met Asn Thr Leu Lys Cys
    610                 615                 620
Thr Val Gly Pro Ala Met Asn Lys His Phe Asn Met Ser Ile Ile Ile
625                 630                 635                 640
Ser Asn Gly His Gly Thr Thr Gln Tyr Ser Thr Phe Ser Tyr Val Asp
                645                 650                 655
Pro Val Ile Thr Ser Ile Ser Pro Lys Tyr Gly Pro Met Ala Gly Gly
                660                 665                 670
Thr Leu Leu Thr Leu Thr Gly Asn Tyr Leu Asn Ser Gly Asn Ser Arg
                675                 680                 685
His Ile Ser Ile Gly Gly Lys Thr Cys Thr Leu Lys Ser Val Ser Asn
    690                 695                 700
Ser Ile Leu Glu Cys Tyr Thr Pro Ala Gln Thr Ile Ser Thr Glu Phe
705                 710                 715                 720
Ala Val Lys Leu Lys Ile Asp Leu Ala Asn Arg Glu Thr Ser Ile Phe
                725                 730                 735
Ser Tyr Arg Glu Asp Pro Ile Val Tyr Glu Ile His Pro Thr Lys Ser
                740                 745                 750
Phe Ile Ser Gly Gly Ser Thr Ile Thr Gly Val Gly Lys Asn Leu Asn
                755                 760                 765
Ser Val Ser Val Pro Arg Met Val Ile Asn Val His Glu Ala Gly Arg
    770                 775                 780
Asn Phe Thr Val Ala Cys Gln His Arg Ser Asn Ser Glu Ile Ile Cys
785                 790                 795                 800
Cys Thr Thr Pro Ser Leu Gln Gln Leu Asn Leu Gln Leu Pro Leu Lys
                805                 810                 815
Thr Lys Ala Phe Phe Met Leu Asp Gly Ile Leu Ser Lys Tyr Phe Asp
                820                 825                 830
Leu Ile Tyr Val His Asn Pro Val Phe Lys Pro Phe Glu Lys Pro Val
                835                 840                 845
Met Ile Ser Met Gly Asn Glu Asn Val Leu Glu Ile Lys Gly Asn Asp
    850                 855                 860
Ile Asp Pro Glu Ala Val Lys Gly Glu Val Leu Lys Val Gly Asn Lys
865                 870                 875                 880
Ser Cys Glu Asn Ile His Leu His Ser Glu Ala Val Leu Cys Thr Val
                885                 890                 895
Pro Asn Asp Leu Leu Lys Leu Asn Ser Glu Leu Asn Ile Glu Trp Lys
                900                 905                 910
Gln Ala Ile Ser Ser Thr Val Leu Gly Lys Val Ile Val Gln Pro Asp
                915                 920                 925
Gln Asn Phe Thr Gly Leu Ile Ala Gly Val Val Ser Ile Ser Thr Ala
    930                 935                 940
```

-continued

Leu Leu Leu Leu Leu Gly Phe Phe Leu Trp Leu Lys Arg Lys Gln
945                 950                 955                 960

Ile Lys Asp Leu Gly Ser Glu Leu Val Arg Tyr Asp Ala Arg Val His
            965                 970                 975

Thr Pro His Leu Asp Arg Leu Val Ser Ala Arg Ser Val Ser Pro Thr
            980                 985                 990

Thr Glu Met Val Ser Asn Glu Ser Val Asp Tyr Arg Ala Thr Phe Pro
        995                 1000                1005

Glu Asp Gln Phe Pro Asn Ser Ser Gln Asn Gly Ser Cys Arg Gln
    1010                1015                1020

Val Gln Tyr Pro Leu Thr Asp Met Ser Pro Ile Leu Thr Ser Gly
    1025                1030                1035

Asp Ser Asp Ile Ser Ser Pro Leu Leu Gln Asn Thr Val His Ile
    1040                1045                1050

Asp Leu Ser Ala Leu Asn Pro Glu Leu Val Gln Ala Val Gln His
    1055                1060                1065

Val Val Ile Gly Pro Ser Ser Leu Ile Val His Phe Asn Glu Val
    1070                1075                1080

Ile Gly Arg Gly His Phe Gly Cys Val Tyr His Gly Thr Leu Leu
    1085                1090                1095

Asp Asn Asp Gly Lys Lys Ile His Cys Ala Val Lys Ser Leu Asn
    1100                1105                1110

Arg Ile Thr Asp Ile Gly Glu Val Ser Gln Phe Leu Thr Glu Gly
    1115                1120                1125

Ile Ile Met Lys Asp Phe Ser His Pro Asn Val Leu Ser Leu Leu
    1130                1135                1140

Gly Ile Cys Leu Arg Ser Glu Gly Ser Pro Leu Val Val Leu Pro
    1145                1150                1155

Tyr Met Lys His Gly Asp Leu Arg Asn Phe Ile Arg Asn Glu Thr
    1160                1165                1170

His Asn Pro Thr Val Lys Asp Leu Ile Gly Phe Gly Leu Gln Val
    1175                1180                1185

Ala Lys Gly Met Lys Tyr Leu Ala Ser Lys Lys Phe Val His Arg
    1190                1195                1200

Asp Leu Ala Ala Arg Asn Cys Met Leu Asp Glu Lys Phe Thr Val
    1205                1210                1215

Lys Val Ala Asp Phe Gly Leu Ala Arg Asp Met Tyr Asp Lys Glu
    1220                1225                1230

Tyr Tyr Ser Val His Asn Lys Thr Gly Ala Lys Leu Pro Val Lys
    1235                1240                1245

Trp Met Ala Leu Glu Ser Leu Gln Thr Gln Lys Phe Thr Thr Lys
    1250                1255                1260

Ser Asp Val Trp Ser Phe Gly Val Leu Leu Trp Glu Leu Met Thr
    1265                1270                1275

Arg Gly Ala Pro Pro Tyr Pro Asp Val Asn Thr Phe Asp Ile Thr
    1280                1285                1290

Val Tyr Leu Leu Gln Gly Arg Arg Leu Leu Gln Pro Glu Tyr Cys
    1295                1300                1305

Pro Asp Pro Leu Tyr Glu Val Met Leu Lys Cys Trp His Pro Lys
    1310                1315                1320

Ala Glu Met Arg Pro Ser Phe Ser Glu Leu Val Ser Arg Ile Ser
    1325                1330                1335

Ala Ile Phe Ser Thr Phe Ile Gly Glu His Tyr Val His Val Asn

```
            1340                1345                1350

Ala Thr Tyr Val Asn Val Lys Cys Val Ala Pro Tyr Pro Ser Leu
    1355                1360                1365

Leu Ser Ser Glu Asp Asn Ala Asp Asp Glu Val Asp Thr Arg Pro
    1370                1375                1380

Ala Ser Phe Trp Glu Thr Ser
    1385                1390

<210> SEQ ID NO 14
<211> LENGTH: 8
<212> TYPE: PRT
<213> ORGANISM: Artificial sequence
<220> FEATURE:
<223> OTHER INFORMATION: Synthetic construct

<400> SEQUENCE: 14

Val Ala Asp Phe Gly Leu Ala Arg
1               5

<210> SEQ ID NO 15
<211> LENGTH: 9
<212> TYPE: PRT
<213> ORGANISM: Artificial sequence
<220> FEATURE:
<223> OTHER INFORMATION: Synthetic construct

<400> SEQUENCE: 15

Thr Glu Phe Thr Thr Ala Leu Gln Arg
1               5

<210> SEQ ID NO 16
<211> LENGTH: 13
<212> TYPE: PRT
<213> ORGANISM: Artificial sequence
<220> FEATURE:
<223> OTHER INFORMATION: Synthetic construct

<400> SEQUENCE: 16

Val Phe Pro Asn Ser Ala Pro Leu Glu Gly Gly Thr Arg
1               5                   10

<210> SEQ ID NO 17
<211> LENGTH: 240
<212> TYPE: PRT
<213> ORGANISM: Mus musculus

<400> SEQUENCE: 17

Ser Leu Leu Gly Ile Cys Leu Arg Ser Glu Gly Ser Pro Leu Val Val
1               5                   10                  15

Leu Pro Tyr Met Lys His Gly Asp Leu Arg Asn Phe Ile Arg Asn Glu
            20                  25                  30

Thr His Asn Pro Thr Val Lys Asp Leu Ile Gly Phe Gly Leu Gln Val
        35                  40                  45

Ala Lys Gly Met Lys Tyr Leu Ala Ser Lys Lys Phe Val His Arg Asp
    50                  55                  60

Leu Ala Ala Arg Asn Cys Met Leu Asp Glu Lys Phe Thr Val Lys Val
65                  70                  75                  80

Ala Asp Phe Gly Leu Ala Arg Asp Met Tyr Asp Lys Glu Tyr Tyr Ser
                85                  90                  95

Val His Asn Lys Thr Gly Ala Lys Leu Pro Val Lys Trp Met Ala Leu
            100                 105                 110
```

```
Glu Ser Leu Gln Thr Gln Lys Phe Thr Thr Lys Ser Asp Val Trp Ser
            115                 120                 125

Phe Gly Val Leu Leu Trp Glu Leu Met Thr Arg Gly Ala Pro Pro Tyr
130                 135                 140

Pro Asp Val Asn Thr Phe Asp Ile Thr Ile Tyr Leu Leu Gln Gly Arg
145                 150                 155                 160

Arg Leu Leu Gln Pro Glu Tyr Cys Pro Asp Ala Leu Tyr Glu Val Met
                165                 170                 175

Leu Lys Cys Trp His Pro Lys Ala Glu Met Arg Pro Ser Phe Ser Glu
            180                 185                 190

Leu Val Ser Arg Ile Ser Ser Ile Phe Ser Thr Phe Ile Gly Glu His
            195                 200                 205

Tyr Val His Val Asn Ala Thr Tyr Val Asn Val Lys Cys Val Ala Pro
210                 215                 220

Tyr Pro Ser Leu Leu Pro Ser Gln Asp Asn Ile Asp Gly Glu Gly Asn
225                 230                 235                 240
```

<210> SEQ ID NO 18
<211> LENGTH: 240
<212> TYPE: PRT
<213> ORGANISM: Homo sapiens

<400> SEQUENCE: 18

```
Ser Leu Leu Gly Ile Cys Leu Arg Ser Glu Gly Ser Pro Leu Val Val
1               5                   10                  15

Leu Pro Tyr Met Lys His Gly Asp Leu Arg Asn Phe Ile Arg Asn Glu
                20                  25                  30

Thr His Asn Pro Thr Val Lys Asp Leu Ile Gly Phe Gly Leu Gln Val
            35                  40                  45

Ala Lys Gly Met Lys Tyr Leu Ala Ser Lys Lys Phe Val His Arg Asp
50                  55                  60

Leu Ala Ala Arg Asn Cys Met Leu Asp Glu Lys Phe Thr Val Lys Val
65                  70                  75                  80

Ala Asp Phe Gly Leu Ala Arg Asp Met Tyr Asp Lys Glu Tyr Tyr Ser
                85                  90                  95

Val His Asn Lys Thr Gly Ala Lys Leu Pro Val Lys Trp Met Ala Leu
            100                 105                 110

Glu Ser Leu Gln Thr Gln Lys Phe Thr Thr Lys Ser Asp Val Trp Ser
            115                 120                 125

Phe Gly Val Leu Leu Trp Glu Leu Met Thr Arg Gly Ala Pro Pro Tyr
130                 135                 140

Pro Asp Val Asn Thr Phe Asp Ile Thr Val Tyr Leu Leu Gln Gly Arg
145                 150                 155                 160

Arg Leu Leu Gln Pro Glu Tyr Cys Pro Asp Pro Leu Tyr Glu Val Met
                165                 170                 175

Leu Lys Cys Trp His Pro Lys Ala Glu Met Arg Pro Ser Phe Ser Glu
            180                 185                 190

Leu Val Ser Arg Ile Ser Ala Ile Phe Ser Thr Phe Ile Gly Glu His
            195                 200                 205

Tyr Val His Val Asn Ala Thr Tyr Val Asn Val Lys Cys Val Ala Pro
210                 215                 220

Tyr Pro Ser Leu Leu Ser Ser Glu Asp Asn Ala Asp Asp Glu Val Asp
225                 230                 235                 240
```

<210> SEQ ID NO 19

```
<211> LENGTH: 232
<212> TYPE: PRT
<213> ORGANISM: Artificial sequence
<220> FEATURE:
<223> OTHER INFORMATION: Synthetic construct

<400> SEQUENCE: 19

Ser Leu Leu Gly Ile Cys Leu Arg Ser Glu Gly Ser Pro Leu Val Val
1               5                   10                  15

Leu Pro Tyr Met Lys His Gly Asp Leu Arg Asn Phe Ile Arg Asn Glu
            20                  25                  30

Thr His Asn Pro Thr Val Lys Asp Leu Ile Gly Phe Gly Leu Gln Val
        35                  40                  45

Ala Lys Gly Met Lys Tyr Leu Ala Ser Lys Lys Phe Val His Arg Asp
    50                  55                  60

Leu Ala Ala Arg Asn Cys Met Leu Asp Glu Lys Phe Thr Val Lys Val
65                  70                  75                  80

Ala Asp Phe Gly Leu Ala Arg Asp Met Tyr Asp Lys Glu Tyr Tyr Ser
                85                  90                  95

Val His Asn Lys Thr Gly Ala Lys Leu Pro Val Lys Trp Met Ala Leu
            100                 105                 110

Glu Ser Leu Gln Thr Gln Lys Phe Thr Thr Lys Ser Asp Val Trp Ser
        115                 120                 125

Phe Gly Val Leu Leu Trp Glu Leu Met Thr Arg Gly Ala Pro Pro Tyr
    130                 135                 140

Pro Asp Val Asn Thr Phe Asp Ile Thr Tyr Leu Leu Gln Gly Arg Arg
145                 150                 155                 160

Leu Leu Gln Pro Glu Tyr Cys Pro Asp Leu Tyr Glu Val Met Leu Lys
                165                 170                 175

Cys Trp His Pro Lys Ala Glu Met Arg Pro Ser Phe Ser Glu Leu Val
            180                 185                 190

Ser Arg Ile Ser Ala Ile Phe Ser Thr Phe Ile Gly Glu His Tyr Val
        195                 200                 205

His Val Asn Ala Thr Tyr Val Asn Val Lys Cys Val Ala Pro Tyr Pro
    210                 215                 220

Ser Leu Leu Ser Asp Asn Asp Glu
225                 230
```